United States Patent
Zhang et al.

(10) Patent No.: US 6,248,904 B1
(45) Date of Patent: Jun. 19, 2001

(54) FLUORESCENCE DYES AND THEIR APPLICATIONS FOR WHOLE-CELL FLUORESCENCE SCREENING ASSAYS FOR CASPASES, PEPTIDASES, PROTEASES AND OTHER ENZYMES AND THE USE THEREOF

(75) Inventors: Han-Zhong Zhang; Sui Xiong Cai, both of San Diego, CA (US)

(73) Assignee: Cytovia, Inc., San Diego, CA (US)

( * ) Notice: Subject to any disclaimer, the term of this patent is extended or adjusted under 35 U.S.C. 154(b) by 0 days.

(21) Appl. No.: 09/357,952

(22) Filed: Jul. 21, 1999

Related U.S. Application Data
(60) Provisional application No. 60/093,642, filed on Jul. 21, 1998.

(51) Int. Cl.[7] .................. C07D 311/88; G01N 33/15; C12Q 1/48; C12Q 1/37

(52) U.S. Cl. .............. 549/227; 435/15; 435/23; 435/24; 436/93

(58) Field of Search ............................... 549/227

(56) References Cited

U.S. PATENT DOCUMENTS

| | | | |
|---|---|---|---|
| 4,336,186 | 6/1982 | Gargiulo et al. | 260/112.5 R |
| 4,500,471 | 2/1985 | Cotter et al. | 560/856 |
| 4,557,862 | 12/1985 | Mangel et al. | 260/112 R |
| 4,640,893 | 2/1987 | Mangel et al. | 435/23 |
| 5,208,148 | 5/1993 | Haugland et al. | 435/14 |
| 5,227,487 | 7/1993 | Haugland et al. | 546/15 |
| 5,362,628 | 11/1994 | Haugland et al. | 435/18 |
| 5,443,986 | 8/1995 | Haugland et al. | 435/4 |
| 5,550,165 | 8/1996 | Ellis et al. | 514/676 |

(List continued on next page.)

FOREIGN PATENT DOCUMENTS

| | | |
|---|---|---|
| 0 285 179 B1 | 10/1988 | (EP) . |
| WO 93/04192 | 3/1993 | (WO) . |
| WO 93/10461 | 5/1993 | (WO) . |
| WO 96/20721 | 7/1996 | (WO) . |
| WO 96/36729 | 11/1996 | (WO) . |
| WO 98/55863 | 12/1998 | (WO) . |
| WO 98/57664 | 12/1998 | (WO) . |

OTHER PUBLICATIONS

Bader, A. et al., *Catalog Handbook of Fine Chemicals 1996–1997*, Aldrich Chemical Company, Inc., Milwaukee, WI, pp. 1133, 1382, 1448, 1463, 1467, 1474.

Assfalg–Machleidt, I. et al., "Membrane Permeable Fluorogenic Rhodamine Substrates for Selective Determination of Cathespin L," *Biol. Chem.* Hoppe–Seyler 373:433–440 (1992).

Ganesh, S. et al., "Flow Cytometric Determination of Aminopeptidase Activities in Viable Cells Using Fluorogenic Rhodamine 110 Substrates," *Cytometry* 20:334–340 (1995).

(List continued on next page.)

*Primary Examiner*—Alan L. Rotman
(74) *Attorney, Agent, or Firm*—Sterne, Kessler, Goldstein & Fox P.L.L.C.

(57) ABSTRACT

The present invention relates to novel fluorescent dyes, novel fluorogenic and fluorescent reporter molecules and new enzyme assay processes that can be used to detect the activity of caspases and other enzymes involved in apoptosis in whole cells, cell lines and tissue samples derived from any living organism or organ. The reporter molecules and assay processes can be used in drug screening procedures to identify compounds which act as inhibitors or inducers of the caspase cascade in whole cells or tissues. The reagents and assays described herein are also useful for determining the chemosensitivity of human cancer cells to treatment with chemotherapeutic drugs. The present invention also relates to novel fluorogenic and fluorescent reporter molecules and new enzyme assay processes that can be used to detect the activity of type 2 methionine aminopeptidase, HIV protease, adenovirus protease, HSV-1 protease, HCMV protease and HCV protease.

10 Claims, 9 Drawing Sheets

U.S. PATENT DOCUMENTS

| | | | |
|---|---|---|---|
| 5,556,992 | 9/1996 | Gaboury et al. | 549/227 |
| 5,576,424 | 11/1996 | Mao et al. | 536/17.9 |
| 5,587,490 | 12/1996 | Goodrich, Jr. et al. | 549/282 |
| 5,605,809 | 2/1997 | Komoriya et al. | 435/23 |
| 5,696,001 | 12/1997 | Habenstein | 436/518 |
| 5,698,411 | 12/1997 | Lucas et al. | 435/29 |
| 5,714,342 | 2/1998 | Komoriya et al. | 435/23 |
| 5,733,719 | 3/1998 | Jaffe et al. | 435/4 |
| 5,773,236 * | 6/1998 | Diwu et al. | 435/15 |
| 5,776,720 | 7/1998 | Jaffe et al. | 435/29 |
| 5,843,635 | 12/1998 | Schlossman et al. | 435/5 |
| 5,849,513 | 12/1998 | Jaffe et al. | 435/29 |
| 5,871,946 | 2/1999 | Lucas et al. | 435/18 |
| 5,897,992 | 4/1999 | Fearnhead et al. | 435/29 |
| 5,908,750 | 6/1999 | Reed et al. | 435/6 |

OTHER PUBLICATIONS

Haughland, R.P. and I.D. Johnson, "Detecting Enzymes in Living Cells Using Fluorogenic Substrates," *J. Fluorescence* 3:119–127 (1993).

Haughland, R.P., "Detecting Enzymatic Activity in Cells Using Fluorogenic Substrates," *Biotechnic & Histochem.* 70:243–251 (1995).

Johnson, A.F. et al., "Nonisotopic DNA Detection System Employing Elastase and a Fluorogenic Rhodamine Substrate," *Anal. Chem.* 65:2352–2359 (1993).

Klingel, S. et al., "Chapter 29, Flow Cytometric Determination of Cysteine and Serine Proteinase Activities in Living Cells with Rhodamine 110 Substrates," *Methods in Cell Biology* 41:449–459 (1994).

Leytus, S.P. et al., "Rhodamine–based compounds as fluorogenic substrates for serine proteinases," *Biochem. J.* 209:299–307 (1983).

Leytus, S.P. et al., "New class of sensitive and selective fluorogenic substrates for serine proteinases," *Biochem J.* 215:253–260 (1983).

Morliere, P. et al., "Interaction of Tetrapyrrolic Rings with Rhodamine 110 and 123 and with Rhodamine 110 Derivatives Bearing a Peptide Side Chain," *Biochem. Biophys. Res. Commun.* 146:107–113 (1987).

Rothe, G. et al., "Flow Cytometric Analysis of Protease Activities in Vital Cells," *Biol. Chem.* Hoppe–Seyler 373:547–554 (1992).

Alphabetical Price List of New Products, Molecular Probes, Inc pp–1–4, (Jan. 1994).

Adams, S.R. et al., "Biologically Useful Chelators That Take Up $Ca^{2+}$ upon Illumination," *J. Am. Chem. Soc.* 111:7957–7968 (1989).

Alnemri, E.S. et al., "Human ICE/CED–3 Protease Nomenclature," *Cell* 87:171 (1996).

An, S. and K.A. Knox, "Ligation of CD40 Rescues Ramos–Burkitt lymphoma B cells from calcium ionophore–antigen receptor–triggered apoptosis by inhibiting activation of the cysteine protease CPP32/Yama and cleavage of its substrate PARP," *FEBS Letters* 386:115–122 (1996).

Armstrong, R.C. et al., "Fas–induced Activation of the Cell Death–related Protease CPP32 Is Inhibited by Bcl–2 and by ICE Family Protease Inhibitors," *J. Biol. Chem.* 271:16850–16855 (1996).

Bonneau, P.R. et al., "Design of Fluorogenic Peptide Substrates for Human Cytomegalovirus Protease Based on Structure–Activity Relationship Studies," *Anal. Biochem.* 255:59–65 (1998).

di Giovine, F.S. and G.W. Duff, "Interleukin 1: the first interleukin," *Immunol. Today* 11:13–19 (1990).

Dilanni, C.L. et al., "In Vitro Activity of the Herpes Simplex Virus Type 1 Protease with Peptide Substrates," *J. Biol. Chem.* 268:25449–25454 (1993).

Dinarello, C.A., "Interleukin–1 and Interleukin–1 Antagonism," *Blood* 77:1627–1652 (1991).

Ding, J. et al., "Crystal structure of the human adenovirus proteinase with its 11 amino acid cofactor," *EMBO J.* 15:1778–1783 (1996).

Diouri, M. et al., "Cleavage Efficiency by Adenovirus Protease Is Site–dependent," *J. Biol. Chem.* 271:32511–32514 (1996).

Evans, D.B. et al., "An Ultrasensitive Human Immunodeficiency Virus Type 1 Protease Radioimmuno Rate Assay with a Potential for Monitoring Blood Levels of Protease Inhibitors in Acquired Immunodeficiency Disease Syndrome Patients," *Anal. Biochem.* 206:288–292 (1992).

Friesen, C. et al., "Involvement of the CD95 (APO–1/Fas) receptor/ligand system in drug–induced apoptosis in leukemia cells," *Nature Med.* 2:574–577 (1996).

Gamen, S. et al., "Doxorubicin–induced apoptosis in human T–cell leukemia is mediated by caspase–3 activation in a Fas–independent way," *FEBS Lett.* 417:360–364 (Nov. 1997).

Gao, M. et al., "The Protease of Herpes Simplex Virus Type 1 Is Essential for Functional Capsid Formation and Viral Growth," *J. Virol.* 68:3702–3712 (1994).

Griffith, E.C. et al., "Methionine aminopeptidase (type 2) is the common target for angiogenesis inhibitors AGM–1470 and ovalicin," *Chem. Biol.* 4:461–471 (Jun. 1997).

Haugland, R.P., *Handbook of Fluorescent Probes and Research Chemicals*, $6^{th}$ Ed., Molecular Probes, Inc., Eugene, OR, pp. 28, 54 (1996).

Hickman, J.A., "Apoptosis induced by anticancer drugs," *Cancer and Metastasis Rev.* 11:121–139 (1992).

Holskin, B.P. et al., "A Continuous Fluorescence–Based Array of Human Cytomegalovirus Protease Using a Peptide Substrate," *Anal. Biochem.* 226:148–155 (1995).

Hyland, L.J. et al., "A Radiometric Assay for HIV–1 Protease," *Anal. Biochem.* 188:408–415 (1990).

Joensuu, H. et al., "Bcl–2 Protein Expression and Long–Term Survival in Breast Cancer," *Am. J. Pathol.* 145:1191–1198 (1994).

Li, X. and Y.–H. Chang, "Evidence That the Human Homologue of a Rat Initiation Factor–2 Associated Protein ($p^{67}$) Is a Methonine Aminopeptidase," *Biochem. Biophys. Res. Comm.* 227:152–159 (1996).

Los, M. et al., "Requirement of an ICE/CED–3 protease for Fas/APO–1–mediated apoptosis," *Nature* 375:81–83 (1995).

Los, M. et al., "Cross–Resistance of CD95– and Drug–Induced Apoptosis as a Consequence of Deficient Activation of Caspases (ICE/Ced–3 Proteases)," *Blood* 90:3118–3129 (Oct. 1997).

Maldonado, V. et al.,"Modulation of NF–κB, p53 and Bcl–2 in apoptosis induced by cisplatin in HeLa cells," *Mutation Res.* 381:67–75 (Nov. 1997).

Martin, J. A. et al., "Inhibitors of HIV Proteinase," *Prog. Med. Chem.* 32:239–287 (1995).

Matayoshi, E.D. et al., "Novel Fluorogenic Substrates for Assaying Retroviral Proteases by Resonance Energy Transfer," *Science* 247:954–958 (1990).

McCann III, P.J. et al., "Invesitgation of the Specificity of the Herpes Simplex Virus Type 1 Protease by Point Mutagenesis of the Autoproteolysis Sites," *J. Virol.* 68:526–529 (1994).

Miller, L.K., "Baculovirus Interaction With Host Apoptotic Pathways," *J. Cell. Physiol.* 173:178–182 (Nov. 1997).

Miura, M. et al., "Induction of Apoptosis in Fibroblasts by IL–1β–Converting Enzyme, a Mammalian Homolog of the *C. elegans* Cell Death Gene ced–3," *Cell* 75:653–660 (1993).

Mosley, B. et al., "The Interleukin–1 Receptor Binds the Human Interleukin–1α Precursor but Not the Interleukin–1β Precursor," *J. Biol. Chem.* 262:2941–2944 (1987).

O'Boyle II, D. R. et al., "Identification of a Novel Peptide Substrate of HSV–1 Protease Using Substrate Phage Display," *Virology* 236:338–347 (Sep. 1997).

Oppenheim, J.J. et al., "There is more than one interleukin 1," *Immunol. Today* 7:45–56 (1986).

Richards, A.D. et al., "Sensitive, Soluble Chromogenic Substrates for HIV–1 Proteinase," *J. Biol. Chem.* 265:7733–7736 (1990).

Sin, N. et al., "The anti–angiogenic agent fumagillin covalently binds and inhibits the methionine aminopeptidase, MetAP–2," *Proc. Natl. Acad. Sci. USA* 94:6099–6103 (Jun. 1997).

Stevens, J.T. et al., "In vitro proteolytic activity and active–site identification of the human cytomegalovirus protease," *Eur. J. Biochem.* 226:361–367 (1994).

Tamburini, P.P. et al., "A Fluorometric Assay for HIV–Protease Activity Using High–Performance Liquid Chromatography," *Anal. Biochem.* 186:363–368 (1990).

Thornberry, N.A. et al., "A novel heterodimeric cysteine protease is required for interleukin–1β processing in monocytes," *Nature* 356:768–774 (1992).

Thornberry, N.A. et al., "A Combinatorial Approach Defines Specificities of Members of the Caspase Family and Granzyme B," *J. Biol. Chem.* 272:17907–17911 (Jul. 1997).

Toth, M.V. and G.R. Marshall, "A simple, continuous fluorometric assay for HIV protease," *Int. J. Peptide Protein Res.* 36:544–550 (1990).

Tyagi, S.C. and C.A. Carter, "Continuous Assay of the Hydrolytic Activity of Human Immunodeficiency Virus–1 Protease," *Anal. Biochem.* 200:143–148 (1992).

Webb, N.R. and M.D. Summers, "Expression of Proteins Using Recombinant Baculoviruses," *Tech.—J. Meth. Cell Molec. Biol.* 2:173–188 (1990).

Weber, J.M., "Adenovirus Endopeptidase and Its Role in Virus Infection," in *The Molecular Repertoire of Adenoviruses I, Viron Structure and Infection,* Doerfler, W. and Böhm, P., eds., Springer–Verlag, Berlin, pp. 227–235 (1995).

West, M.L. and D.P. Fairlie, "Targeting HIV–1 protease: a test of drug–design methodologies," *Trends Pharmacol. Sciences* 16:67–74 (1995).

Yoon, H. J. et al., "DNA topoisomerase II cleavage of telomeres in vitro and in vivo," *Biochem. Biophys. Acta* 1395:110–120 (Jan. 1998).

Yuan, J. et al., "The *C. elegans* Cell Death Gene ced–3 Encodes a Protein Similar to Mammalian Interleukin–1β–Converting Enzyme," *Cell* 75:641–652 (1993).

Zhang, R. et al., "Probing the Substrate Specificity of Hepatitis C Virus NS3 Serine Protease by Using Synthetic Peptides," *J. Virol.* 71:6208–6213 (Aug. 1997).

Zhang,

\* cited by examiner

R110

Pentafluorobenzoyl R110

N-Gly-R110-PFB

N-Cbz-Gly-R110-PFB

SEQUENCE LISTING

```
<160> NUMBER OF SEQ ID NOS: 139

<210> SEQ ID NO: 1
<211> LENGTH: 4
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 1

Trp Glu His Asp
  1

<210> SEQ ID NO: 2
<211> LENGTH: 4
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 2

Tyr Val Ala Asp
  1
```

```
<210> SEQ ID NO: 3
<211> LENGTH: 4
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 3

Leu Glu His Asp
 1

<210> SEQ ID NO: 4
<211> LENGTH: 4
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 4

Asp Glu Thr Asp
 1

<210> SEQ ID NO: 5
<211> LENGTH: 4
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 5

Asp Glu Val Asp
 1

<210> SEQ ID NO: 6
<211> LENGTH: 4
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 6

Asp Glu His Asp
 1

<210> SEQ ID NO: 7
<211> LENGTH: 4
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 7

Val Glu His Asp
 1

<210> SEQ ID NO: 8
<211> LENGTH: 4
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 8
```

Leu Glu Thr Asp
 1

<210> SEQ ID NO: 9
<211> LENGTH: 4
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 9

Leu Glu Val Asp
 1

<210> SEQ ID NO: 10
<211> LENGTH: 4
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 10

Ser His Val Asp
 1

<210> SEQ ID NO: 11
<211> LENGTH: 4
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 11

Asp Glu Leu Asp
 1

<210> SEQ ID NO: 12
<211> LENGTH: 4
<212> TYPE: PRT
<213> ORGANISM: Artificial Sequence
<220> FEATURE:
<223> OTHER INFORMATION: Description of Artificial Sequence: Synthetic
      Peptide
<220> FEATURE:

<400> SEQUENCE: 12

Asp Gly Pro Asp
 1

<210> SEQ ID NO: 13
<211> LENGTH: 4
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 13

Asp Glu Pro Asp
 1

<210> SEQ ID NO: 14
<211> LENGTH: 4
<212> TYPE: PRT

```
<213> ORGANISM: Artificial Sequence
<220> FEATURE:
<223> OTHER INFORMATION: Description of Artificial Sequence: Synthetic
      Peptide

<400> SEQUENCE: 14

Asp Gly Thr Asp
 1

<210> SEQ ID NO: 15
<211> LENGTH: 4
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 15

Asp Leu Asn Asp
 1

<210> SEQ ID NO: 16
<211> LENGTH: 4
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 16

Asp Glu Glu Asp
 1

<210> SEQ ID NO: 17
<211> LENGTH: 4
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 17

Asp Ser Leu Asp
 1

<210> SEQ ID NO: 18
<211> LENGTH: 4
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 18

Asp Val Pro Asp
 1

<210> SEQ ID NO: 19
<211> LENGTH: 4
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 19

Asp Glu Ala Asp
 1
```

```
<210> SEQ ID NO: 20
<211> LENGTH: 4
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 20

Asp Ser Tyr Asp
  1

<210> SEQ ID NO: 21
<211> LENGTH: 4
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 21

Glu Leu Pro Asp
  1

<210> SEQ ID NO: 22
<211> LENGTH: 4
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 22

Val Glu Asp Asp
  1

<210> SEQ ID NO: 23
<211> LENGTH: 4
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 23

Ile Glu Pro Asp
  1

<210> SEQ ID NO: 24
<211> LENGTH: 4
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 24

Ile Glu Thr Asp
  1

<210> SEQ ID NO: 25
<211> LENGTH: 4
<212> TYPE: PRT
<213> ORGANISM: Artificial Sequence
<220> FEATURE:
<221> NAME/KEY: UNSURE
<222> LOCATION: (1)
```

```
<223> OTHER INFORMATION: Amino Acid may be Tryptophan or Leucine
<220> FEATURE:
<223> OTHER INFORMATION: Description of Artificial Sequence: Synthetic
      Peptide

<400> SEQUENCE: 25

Xaa Glu His Asp
  1

<210> SEQ ID NO: 26
<211> LENGTH: 4
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 26

Val Glu Ile Asp
  1

<210> SEQ ID NO: 27
<211> LENGTH: 4
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 27

Val Glu Pro Asp
  1

<210> SEQ ID NO: 28
<211> LENGTH: 7
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 28

Ser Gln Asn Tyr Pro Ile Val
  1               5

<210> SEQ ID NO: 29
<211> LENGTH: 7
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 29

Ala Arg Val Leu Ala Glu Ala
  1               5

<210> SEQ ID NO: 30
<211> LENGTH: 7
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 30

Ala Thr Ile Met Met Gln Arg
  1               5
```

```
<210> SEQ ID NO: 31
<211> LENGTH: 7
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 31

Arg Gln Ala Asn Phe Leu Gly
  1               5

<210> SEQ ID NO: 32
<211> LENGTH: 7
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 32

Pro Gly Asn Phe Leu Gln Ser
  1               5

<210> SEQ ID NO: 33
<211> LENGTH: 7
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 33

Ser Phe Ser Phe Pro Gln Ile
  1               5

<210> SEQ ID NO: 34
<211> LENGTH: 7
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 34

Thr Leu Asn Phe Pro Ile Ser
  1               5

<210> SEQ ID NO: 35
<211> LENGTH: 7
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 35

Ala Glu Thr Phe Tyr Val Asp
  1               5

<210> SEQ ID NO: 36
<211> LENGTH: 7
<212> TYPE: PRT
<213> ORGANISM: Artificial Sequence
<220> FEATURE:
<223> OTHER INFORMATION: Description of Artificial Sequence: Synthetic
      Peptide
```

```
<400> SEQUENCE: 36

Arg Lys Val Leu Phe Leu Asp
 1               5

<210> SEQ ID NO: 37
<211> LENGTH: 4
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 37

Arg Gly Phe Pro
 1

<210> SEQ ID NO: 38
<211> LENGTH: 7
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 38

Ser Gln Asn Tyr Pro Val Val
 1               5

<210> SEQ ID NO: 39
<211> LENGTH: 14
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 39

Asp Arg Val Tyr Ile His Pro Phe His Leu Leu Glu Glu Ser
 1               5                  10

<210> SEQ ID NO: 40
<211> LENGTH: 4
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 40

Leu Glu Glu Ser
 1

<210> SEQ ID NO: 41
<211> LENGTH: 8
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 41

Ser Gln Asn Tyr Pro Ile Val Gln
 1               5

<210> SEQ ID NO: 42
<211> LENGTH: 8
```

```
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 42

Ser Gln Asn Leu Phe Leu Asp Gly
  1               5

<210> SEQ ID NO: 43
<211> LENGTH: 8
<212> TYPE: PRT
<213> ORGANISM: Artificial Sequence
<220> FEATURE:
<223> OTHER INFORMATION: Description of Artificial Sequence:  Synthetic
      Peptide

<400> SEQUENCE: 43

Arg Lys Ile Leu Phe Leu Asp Gly
  1               5

<210> SEQ ID NO: 44
<211> LENGTH: 9
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 44

Lys Ala Arg Val Leu Phe Glu Ala Met
  1               5

<210> SEQ ID NO: 45
<211> LENGTH: 4
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 45

Ser Gln Asn Tyr
  1

<210> SEQ ID NO: 46
<211> LENGTH: 4
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 46

Pro Ile Val Gln
  1

<210> SEQ ID NO: 47
<211> LENGTH: 5
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 47

Lys Ala Arg Val Leu
```

```
          1               5

<210> SEQ ID NO: 48
<211> LENGTH: 4
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 48

Ala Arg Val Leu
  1

<210> SEQ ID NO: 49
<211> LENGTH: 4
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 49

Phe Glu Ala Met
  1

<210> SEQ ID NO: 50
<211> LENGTH: 4
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 50

Pro Phe His Leu
  1

<210> SEQ ID NO: 51
<211> LENGTH: 4
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 51

Gln Asn Leu Phe
  1

<210> SEQ ID NO: 52
<211> LENGTH: 5
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 52

Arg Lys Ile Leu Phe
  1               5

<210> SEQ ID NO: 53
<211> LENGTH: 4
<212> TYPE: PRT
<213> ORGANISM: Artificial Sequence
<220> FEATURE:
<223> OTHER INFORMATION: Description of Artificial Sequence: Synthetic
```

Peptide

<400> SEQUENCE: 53

Lys Ile Leu Phe
 1

<210> SEQ ID NO: 54
<211> LENGTH: 4
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 54

Ser Leu Asn Phe
 1

<210> SEQ ID NO: 55
<211> LENGTH: 4
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 55

Leu Arg Gly Gly
 1

<210> SEQ ID NO: 56
<211> LENGTH: 4
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 56

Met Arg Gly Gly
 1

<210> SEQ ID NO: 57
<211> LENGTH: 4
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 57

Ile Arg Gly Gly
 1

<210> SEQ ID NO: 58
<211> LENGTH: 4
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 58

Leu Val Gly Gly
 1

<210> SEQ ID NO: 59

```
<211> LENGTH: 4
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 59

Met Val Gly Gly
  1

<210> SEQ ID NO: 60
<211> LENGTH: 4
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 60

Ile Val Gly Gly
  1

<210> SEQ ID NO: 61
<211> LENGTH: 8
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 61

Leu Val Leu Ala Ser Ser Ser Phe
  1               5

<210> SEQ ID NO: 62
<211> LENGTH: 4
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 62

Leu Val Leu Ala
  1

<210> SEQ ID NO: 63
<211> LENGTH: 11
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 63

Arg Gly Val Val Asn Ala Ser Ser Arg Leu Ala
  1               5                  10

<210> SEQ ID NO: 64
<211> LENGTH: 4
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 64
```

Val Val Asn Ala
1

<210> SEQ ID NO: 65
<211> LENGTH: 4
<212> TYPE: PRT
<213> ORGANISM: Artificial Sequence
<220> FEATURE:
<221> NAME/KEY: SITE
<222> LOCATION: (1)..(2)
<223> OTHER INFORMATION: t-butylglycine
<220> FEATURE:
<223> OTHER INFORMATION: Description of Artificial Sequence: Synthetic
      Peptide

<400> SEQUENCE: 65

Gly Gly Asn Ala
1

<210> SEQ ID NO: 66
<211> LENGTH: 10
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 66

Asp Asp Ile Val Pro Cys Ser Met Ser Tyr
1               5                   10

<210> SEQ ID NO: 67
<211> LENGTH: 6
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 67

Asp Asp Ile Val Pro Cys
1               5

<210> SEQ ID NO: 68
<211> LENGTH: 5
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 68

Asp Ile Val Pro Cys
1               5

<210> SEQ ID NO: 69
<211> LENGTH: 4
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 69

Ile Val Pro Cys
1

<210> SEQ ID NO: 70

```
<211> LENGTH: 4
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 70

Ser Met Ser Tyr
 1

<210> SEQ ID NO: 71
<211> LENGTH: 4
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 71

Glu Val Asp Gly
 1           4

<210> SEQ ID NO: 72
<211> LENGTH: 4
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 72

Leu Gln Thr Asp
 1           4

<210> SEQ ID NO: 73
<211> LENGTH: 4
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 73

Glu Glu Thr Asp
 1           4

<210> SEQ ID NO: 74
<211> LENGTH: 4
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 74

Ala Glu His Asp
 1           4

<210> SEQ ID NO: 75
<211> LENGTH: 6
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 75
```

Asp Glu Val Asp Gly Gly
1               5

<210> SEQ ID NO: 76
<211> LENGTH: 5
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 76

Asp Glu Val Asp Gly
1               5

<210> SEQ ID NO: 77
<211> LENGTH: 4
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 77

Ala Ala Ala Ala
1           4

<210> SEQ ID NO: 78
<211> LENGTH: 5
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 78

Ser Gln Asn Leu Phe
1               5

<210> SEQ ID NO: 79
<211> LENGTH: 6
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 79

Thr Ile Asn Phe Gln Arg
1               5

<210> SEQ ID NO: 80
<211> LENGTH: 7
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 80

Ser Leu Asn Phe Pro Ile Val
1               5

<210> SEQ ID NO: 81
<211> LENGTH: 6
<212> TYPE: PRT
<213> ORGANISM: Artificial Sequence
<220> FEATURE:

<223> OTHER INFORMATION: Description of Artificial Sequence: Synthetic
      Peptide

<400> SEQUENCE: 81

Ser Leu Asn Phe Pro Ile
 1               5

<210> SEQ ID NO: 82
<211> LENGTH: 5
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 82

Ser Leu Asn Phe Pro
 1               5

<210> SEQ ID NO: 83
<211> LENGTH: 6
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 83

Leu Asn Phe Pro Ile Val
 1               5

<210> SEQ ID NO: 84
<211> LENGTH: 5
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 84

Leu Asn Phe Pro Ile
 1               5

<210> SEQ ID NO: 85
<211> LENGTH: 4
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 85

Leu Asn Phe Pro
 1

<210> SEQ ID NO: 86
<211> LENGTH: 6
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 86

Arg Gln Ala Asn Phe Leu
 1               5

```
<210> SEQ ID NO: 87
<211> LENGTH: 5
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 87

Arg Gln Ala Asn Phe
 1               5

<210> SEQ ID NO: 88
<211> LENGTH: 6
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 88

Arg Lys Val Leu Phe Leu
 1               5

<210> SEQ ID NO: 89
<211> LENGTH: 5
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 89

Arg Lys Val Leu Phe
 1               5

<210> SEQ ID NO: 90
<211> LENGTH: 7
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 90

Ala Arg Val Leu Phe Leu Gly
 1               5

<210> SEQ ID NO: 91
<211> LENGTH: 6
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 91

Ala Arg Val Leu Phe Leu
 1               5

<210> SEQ ID NO: 92
<211> LENGTH: 5
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 92
```

Ala Arg Val Leu Phe
1               5

<210> SEQ ID NO: 93
<211> LENGTH: 7
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 93

Ser Gln Asn Tyr Phe Leu Gly
1               5

<210> SEQ ID NO: 94
<211> LENGTH: 6
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 94

Ser Gln Asn Tyr Phe Leu
1               5

<210> SEQ ID NO: 95
<211> LENGTH: 5
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 95

Ser Gln Asn Tyr Phe
1               5

<210> SEQ ID NO: 96
<211> LENGTH: 5
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 96

Met Arg Gly Gly Gly
1               5

<210> SEQ ID NO: 97
<211> LENGTH: 5
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 97

Ile Arg Gly Gly Gly
1               5

<210> SEQ ID NO: 98
<211> LENGTH: 5
<212> TYPE: PRT
<213> ORGANISM: Artificial Sequence

```
<220> FEATURE:
<223> OTHER INFORMATION: Description of Artificial Sequence: Synthetic
      Peptide

<400> SEQUENCE: 98

Leu Val Gly Gly Gly
  1               5

<210> SEQ ID NO: 99
<211> LENGTH: 5
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 99

Met Val Gly Gly Gly
  1               5

<210> SEQ ID NO: 100
<211> LENGTH: 5
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 100

Ile Val Gly Gly Gly
  1               5

<210> SEQ ID NO: 101
<211> LENGTH: 5
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 101

Leu Arg Gly Gly Gly
  1               5

<210> SEQ ID NO: 102
<211> LENGTH: 5
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 102

Leu Arg Gly Gly Ala
  1               5

<210> SEQ ID NO: 103
<211> LENGTH: 7
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 103

Leu Val Leu Ala Ser Ser Ser
  1               5
```

```
<210> SEQ ID NO: 104
<211> LENGTH: 6
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 104

Leu Val Leu Ala Ser Ser
 1               5

<210> SEQ ID NO: 105
<211> LENGTH: 5
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 105

Leu Val Leu Ala Ser
 1               5

<210> SEQ ID NO: 106
<211> LENGTH: 6
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 106

Val Val Asn Ala Ser Ser
 1               5

<210> SEQ ID NO: 107
<211> LENGTH: 5
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 107

Val Val Asn Ala Ser
 1               5

<210> SEQ ID NO: 108
<211> LENGTH: 6
<212> TYPE: PRT
<213> ORGANISM: Artificial Sequence
<220> FEATURE:
<221> NAME/KEY: SITE
<222> LOCATION: (1)..(2)
<223> OTHER INFORMATION: t-butylglycine
<220> FEATURE:
<223> OTHER INFORMATION: Description of Artificial Sequence: Synthetic
      Peptide

<400> SEQUENCE: 108

Gly Gly Asn Ala Ser Ser
 1               5

<210> SEQ ID NO: 109
<211> LENGTH: 5
<212> TYPE: PRT
<213> ORGANISM: Artificial Sequence
```

```
<220> FEATURE:
<221> NAME/KEY: SITE
<222> LOCATION: (1)..(2)
<223> OTHER INFORMATION: t-butylglycine
<220> FEATURE:
<223> OTHER INFORMATION: Description of Artificial Sequence: Synthetic
      Peptide

<400> SEQUENCE: 109

Gly Gly Asn Ala Ser
 1               5

<210> SEQ ID NO: 110
<211> LENGTH: 4
<212> TYPE: PRT
<213> ORGANISM: Artificial Sequence
<220> FEATURE:
<221> NAME/KEY: SITE
<222> LOCATION: (1)..(2)
<223> OTHER INFORMATION: t-butylglycine
<220> FEATURE:
<223> OTHER INFORMATION: Description of Artificial Sequence: Synthetic
      Peptide

<400> SEQUENCE: 110

Gly Gly Asn Ala
 1

<210> SEQ ID NO: 111
<211> LENGTH: 10
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 111

Asp Asp Ile Val Pro Cys Ser Met Ser Thr
 1               5                  10

<210> SEQ ID NO: 112
<211> LENGTH: 9
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 112

Asp Ile Val Pro Cys Ser Met Ser Thr
 1               5

<210> SEQ ID NO: 113
<211> LENGTH: 8
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 113

Ile Val Pro Cys Ser Met Ser Thr
 1               5

<210> SEQ ID NO: 114
<211> LENGTH: 7
<212> TYPE: PRT
<213> ORGANISM: Artificial Sequence
<220> FEATURE:
```

<223> OTHER INFORMATION: Description of Artificial Sequence:Synthetic
      Peptide

<400> SEQUENCE: 114

Ile Val Pro Cys Ser Met Ser
  1               5

<210> SEQ ID NO: 115
<211> LENGTH: 6
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 115

Ile Val Pro Cys Ser Met
  1               5

<210> SEQ ID NO: 116
<211> LENGTH: 5
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 116

Ile Val Pro Cys Ser
  1               5

<210> SEQ ID NO: 117
<211> LENGTH: 6
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 117

Ser Gln Asn Tyr Pro Ile
  1               5

<210> SEQ ID NO: 118
<211> LENGTH: 6
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 118

Ala Arg Val Leu Ala Glu
  1               5

<210> SEQ ID NO: 119
<211> LENGTH: 6
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 119

Ala Thr Ile Met Met Gln
  1               5

```
<210> SEQ ID NO: 120
<211> LENGTH: 6
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 120

Arg Gln Ala Asn Phe Leu
 1               5

<210> SEQ ID NO: 121
<211> LENGTH: 6
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 121

Pro Gly Asn Phe Leu Gln
 1               5

<210> SEQ ID NO: 122
<211> LENGTH: 6
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 122

Ser Phe Ser Phe Pro Gln
 1               5

<210> SEQ ID NO: 123
<211> LENGTH: 6
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 123

Thr Leu Asn Phe Pro Ile
 1               5

<210> SEQ ID NO: 124
<211> LENGTH: 6
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 124

Ala Glu Thr Phe Tyr Val
 1               5

<210> SEQ ID NO: 125
<211> LENGTH: 6
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 125
```

Arg Lys Val Leu Phe Leu
 1               5

<210> SEQ ID NO: 126
<211> LENGTH: 5
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 126

Ser Gln Asn Tyr Pro
 1               5

<210> SEQ ID NO: 127
<211> LENGTH: 5
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 127

Ala Arg Val Leu Ala
 1               5

<210> SEQ ID NO: 128
<211> LENGTH: 5
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 128

Ala Thr Ile Met Met
 1               5

<210> SEQ ID NO: 129
<211> LENGTH: 5
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 129

Arg Gln Ala Asn Phe
 1               5

<210> SEQ ID NO: 130
<211> LENGTH: 5
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 130

Pro Gly Asn Phe Leu
 1               5

<210> SEQ ID NO: 131
<211> LENGTH: 5
<212> TYPE: PRT
<213> ORGANISM: Artificial Sequence

```
<220> FEATURE:
<223> OTHER INFORMATION: Description of Artificial Sequence: Synthetic
      Peptide

<400> SEQUENCE: 131

Ser Phe Ser Phe Pro
 1               5

<210> SEQ ID NO: 132
<211> LENGTH: 5
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 132

Thr Leu Asn Phe Pro
 1               5

<210> SEQ ID NO: 133
<211> LENGTH: 5
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 133

Ala Glu Thr Phe Tyr
 1               5

<210> SEQ ID NO: 134
<211> LENGTH: 5
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 134

Arg Lys Val Leu Phe
 1               5

<210> SEQ ID NO: 135
<211> LENGTH: 5
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 135

Met Arg Gly Gly Ala
 1               5

<210> SEQ ID NO: 136
<211> LENGTH: 5
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 136

Ile Arg Gly Gly Ala
 1               5
```

```
<210> SEQ ID NO: 137
<211> LENGTH: 5
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 137

Leu Val Gly Gly Ala
 1               5

<210> SEQ ID NO: 138
<211> LENGTH: 5
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 138

Met Val Gly Gly Ala
 1               5

<210> SEQ ID NO: 139
<211> LENGTH: 5
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 139

Ile Val Gly Gly Ala
 1               5
```

FLUORESCENCE DYES AND THEIR APPLICATIONS FOR WHOLE-CELL FLUORESCENCE SCREENING ASSAYS FOR CASPASES, PEPTIDASES, PROTEASES AND OTHER ENZYMES AND THE USE THEREOF

The present application claims the benefit of U.S. provisional application 60/093,642 filed Jul. 21, 1998 abandoned.

DESCRIPTION OF BACKGROUND ART

1. Field of the Invention

This invention is in the field of intracellular detection of enzymes using fluorogenic or fluorescent probes. The invention relates to novel fluorescent dyes and application of these dyes for the preparation of novel fluorogenic or fluorescent peptide or amino acid derivatives which are substrates of proteases and peptidases. In particular, the invention relates to novel fluorogenic or fluorescent peptide derivatives which are substrates of enzymes involved in apoptosis, such as caspases and the lymphocyte-derived serine protease Granzyme B. The invention also relates to a process for measuring the activity of caspases and other enzymes involved in apoptosis in living or dead whole cells, cell lines or tissue samples derived from any healthy, diseased, infected or cancerous organ or tissue. The invention also relates to the use of the fluorogenic or fluorescent substrates in a novel assay system for discovering or detecting inhibitors or inducers of apoptosis in compound collections or compound libraries. Furthermore, the invention relates to the use of the fluorogenic or fluorescent substrates in determining the sensitivity of cancer cells to treatment with chemotherapeutic drugs. The invention also relates to novel fluorogenic or fluorescent peptide derivatives which are substrates of exopeptidases such as aminopeptidase A and N, methionine aminopeptidase and dipeptidyl-peptidase IV, endopetidases such as calpain, proteases such as HIV proteases, HCMV protease, HSV protease, HCV protease and adenovirus protease.

2. Related Art

Organisms eliminate unwanted cells by a process variously known as regulated cell death, programmed cell death or apoptosis. Such cell death occurs as a normal aspect of animal development as well as in tissue homeostasis and aging (Glucksmann, A., *Biol. Rev. Cambridge Philos. Soc.* 26:59–86 (1951); Glucksmann, A., *Archives de Biologie* 76:419–437 (1965); Ellis et al., *Dev.* 112:591–603 (1991); Vaux et al., *Cell* 76:777–779 (1994)). Apoptosis regulates cell number, facilitates morphogenesis, removes harmful or otherwise abnormal cells and eliminates cells that have already performed their function. Additionally, apoptosis occurs in response to various physiological stresses, such as hypoxia or ischemia (PCT published application WO96/20721).

There are a number of morphological changes shared by cells experiencing regulated cell death, including plasma and nuclear membrane blebbing, cell shrinkage (condensation of nucleoplasm and cytoplasm), organelle relocalization and compaction, chromatin condensation and production of apoptotic bodies (membrane enclosed particles containing intracellular material) (Orrenius, S., *J. Internal Medicine* 237:529–536 (1995)).

Apoptosis is achieved through an endogenous mechanism of cellular suicide (Wyllie, A. H., in *Cell Death in Biology and Pathology*, Bowen and Lockshin, eds., Chapman and Hall (1981), pp. 9–34). A cell activates its internally encoded suicide program as a result of either internal or external signals. The suicide program is executed through the activation of a carefully regulated genetic program (Wylie et al., *Int. Rev. Cyt.* 68:251 (1980); Ellis et al., *Ann. Rev. Cell Bio.* 7:663 (1991)). Apoptotic cells and bodies are usually recognized and cleared by neighboring cells or macrophages before lysis. Because of this clearance mechanism, inflammation is not induced despite the clearance of great numbers of cells (Orrenius, S., *J. Internal Medicine* 237:529–536 (1995)).

Mammalian interleukin-1β (IL-1β) plays an important role in various pathologic processes, including chronic and acute inflammation and autoimmune diseases (Oppenheim, J. H., et al., *Immunology Today*, 7:45–56 (1986)). IL-1β is synthesized as a cell associated precursor polypeptide (pro-IL-1β) that is unable to bind IL-1 receptors and is biologically inactive (Mosley et al., *J. Biol. Chem.* 262:2941–2944 (1987)). By inhibiting conversion of precursor IL-1β to mature IL-1β, the activity of interleukin-1 can be inhibited. IL-1 is also a cytokine involved in mediating a wide range of biological responses including inflammation, septic shock, wound healing, hematopoiesis and growth of certain leukemias (Dinarello, C. A., Blood 77:1627–1652 (1991); diGiovine et al., *Immunology Today* 11:13 (1990)). Interleukin-1β converting enzyme (ICE) is a protease responsible for the activation of interleukin-1β (IL-1β) (Thornberry, N. A., et al., *Nature* 356:768 (1992); Yuan, J., et al., *Cell* 75:641 (1993)). ICE is a substrate-specific cysteine protease that cleaves the inactive prointerleukin-1 to produce the mature IL-1. The genes that encode for ICE and CPP32 are members of the mammalian ICE/Ced-3 family of genes which presently includes at least twelve members: ICE, CPP32/Yama/Apopain, mICE2, ICE4, ICH1, TX/ICH-2, MCH2, MCH3, MCH4, FLICE/MACH/MCH5, ICE-LAP6 and ICEre1III. The proteolytic activity of this family of cysteine proteases, whose active site cysteine residue is essential for ICE-mediated apoptosis, appears critical in mediating cell death (Miura et al., *Cell* 75:653–660 (1993)). This gene family has recently been named caspases (Alnernri, E. S., et al. *Cell*, 87:171 (1996)).

A death trigger, such as Tumor Necrosis Factor, FAS-ligand, oxygen or nutrient deprivation, viruses, toxins, anti-cancer drugs etc., can activate caspases within cells in a cascade-like fashion where caspases upstream in the cascade (e.g. FLICE/MACH/MCH5) can activate caspases further downstream in the cascade (e.g. CPP-32/Yama/Apopain). Activation of the caspase cascade leads to cell death.

A wealth of scientific evidence suggests that, in many diseases, the caspase cascade is activated when it shouldn't be. This leads to excessive cellular suicide and organ failure. Diseases involving inappropriate activation of the caspase cascade and subsequent cellular suicide include myocardial infarction, congestive heart failure, autoimmune diseases, AIDS, viral infections, kidney failure, liver failure, rheumatoid arthritis, ischemic stroke, neurodegenerative diseases, atherosclerosis etc. Therefore, the discovery of novel drugs that can block or inhibit the activation of the caspase cascade would have wide-ranging impact on the treatment of degenerative diseases of most, if not all, organ systems of the human body.

Caspases are also thought to be crucial in the development and treatment of cancer. There is mounting evidence that cancer cells, while containing caspases, lack parts of the molecular machinery that activate the caspase cascade (Los et al., *Blood*, Vol. 90, No 8:3118–3129 (1997)). This causes the cancer cells to lose their capacity to undergo cellular suicide and the cells become immortal-they become cancerous.

It has been shown that chemotherapeutic (anti-cancer) drugs can trigger cancer cells to undergo suicide by re-activating the dormant caspase cascade. This may be a crucial aspect of the mode of action of most, if not all, known anticancer drugs (Los et al., *Blood*, Vol. 90, No 8:3118–3129 (1997); Friesen et al., *Nat. Med.* 2:574 (1996)). Chemotherapeutic drugs may differ in their capacity to activate the caspase system in different classes of cancers. Moreover, it is likely that anti-cancer drugs differ in their ability to activate the caspase cascade in a given cancer (e.g. lung cancer) and in different patients. In other words, there are differences from one patient to another in the chemosensitivity of, e.g. lung cancer cells, to various anti-cancer drugs.

In summary, the excessive activation of the caspase cascade plays a crucial role in a wide variety of degenerative organ diseases, while a non-functioning caspase system is a hallmark of cancer cells. New drugs that inhibit or stimulate the caspase cascade are likely to revolutionize the treatment of numerous human diseases ranging from infectious, cardiovascular, endocrine, kidney, liver and brain diseases to diseases of the immune system and to cancer.

In order to find drugs that either inhibit or stimulate the caspase cascade, it is necessary to develop high-throughput caspase activation (HTCA) assays. These HTCA assays must be able to monitor activation or inhibition of the caspase cascade inside living or whole cells. Ideally, HTCA assays should be versatile enough to measure the caspase cascade activity inside any living or whole cell regardless of the cell's origin. Furthermore, such HTCA assays should be able to measure—within living or whole cells—the activation or inhibition of any of the caspase enzymes or any other enzymes that are involved in the caspase cascade. Developing such versatile HTCA assays represents a substantial advance in the field of drug screening.

Currently available HTCA assays do not permit inner cellular screening for compounds that can either activate or inhibit the caspase cascade. There are only cell-free, high-throughput screening assays available that can measure the activity of individually isolated caspase enzymes, or assays that can measure the activity of caspases in dead cells which have been permeabilized by osmotic shock (Los et al., *Blood*, Vol. 90, No 8:3118–3129 (1997)). These cell-free enzyme assays cannot predict the effect of a compound on the caspase cascade in living cells for the following reasons:

1) Cell free assays, or assays using dead, permeabilized cells, cannot predict the ability of compounds to penetrate the cellular membrane. This is crucial because the caspase cascade resides in the interior of the cells. In order to be active, a compound must not only be able to modulate the caspase enzyme or enzymes, but it must also be able to penetrate the intact cell membrane. Cell-free assays or assays using dead cells are therefore unable to determine whether or not a compound will be potentially useful as a drug.
2) Isolated caspases in cell-free assays are highly susceptible to oxidation and to compounds that can cause oxidation of the enzymes. This property of isolated caspases makes cell free caspase screening assays highly susceptible to oxidative impurities and has precluded successful use of these assays for high-throughput screening of combinatorial (or other) chemical libraries. Previous mass screening efforts, using cell-free caspase enzyme assays, have led to the discovery of numerous inhibitors which oxidize caspases, but no compound that would be useful as a potential drug.
3) Numerous cellular receptors, proteins, cell constituents and cofactors—many of which are still unknown—can influence the caspase cascade in living cells. Cell-free caspase assays or assays using permeabilized, dead cells do not take into account these cellular receptors and cofactors. Because of this, it is possible that a compound identified in a cell-free or dead-cell caspase assay will not work in living cells. On the other hand, a compound that might inhibit or stimulate the caspase cascade indirectly through one of the cellular receptors or cofactors would be missed entirely in an cell-free or dead-cell caspase assay.
4) It is highly likely that the caspase cascade functions differently in cells derived from different organs. There is growing evidence that the receptors and cofactors that influence the caspase cascade differ among cell types. Using cell-free or dead cell assays, it would be virtually impossible to identify cell-type or organ specific modulators of the caspase cascade.

A potentially important application of a HTCA assay system for measuring intracellular caspase enzymes or any other enzymes involved in apoptosis is chemosensitivity testing of human cancers. It is known that there is a genetic difference in the susceptibility of human cancers to the currently marketed anti-cancer drugs. For example, lung cancer cells in one patient might be sensitive to Drug A, while another patient's lung cancer might be insensitive to Drug A, but sensitive to Drug B. This pharmacogenetic difference in chemosensitivity of cancer cells from different individuals is a well-known phenomenon.

In the past, attempts have been made to determine the chemosensitivity of cancer cells taken from individual patients prior to designing a treatment regimen with one or more of the marketed anti-cancer drugs. However, chemosensitivity testing has not found wide-spread use because the procedures involved have some inherent technical difficulties. The testing is very time consuming (six or more days per screen) and it requires culturing of the cells prior to screening. The cell culture leads to clonal selection of cells and the cultured cells are then no longer representative of the cancer in the patient. A HTCA assay system for quickly measuring intracellular caspase activity could be used to determine very rapidly the chemosensitivity profile of freshly excised cancer cells. If the assay has a high throughput, it would be feasible to test chemosensitivity of multiple samples taken from the same patient, e.g. from different metastases. This information could then be used to design a treatment regimen using combinations of marketed anti-cancer drugs to which the cells showed greatest sensitivity.

It is clear that the need exists for HTCA assays and reagents for such assays that can be employed in drug discovery or diagnostic procedures to quickly detect and measure the activity of compounds that activate or inhibit the caspase cascade or other enzymes involved in apoptosis in the interior of living or dead whole cells. A reagent for this type of cell assay ideally should meet the following conditions: a) there should be a big difference in fluorescence signal between peptide-reporter molecule and reporter molecule after the amide bond in peptide-reporter is cleaved by the caspases or other enzymes involved in apoptosis, preferably the peptide-reporter molecule should be non-fluorescent and most preferably the peptide-reporter molecule should be non-fluorescent and colorless; b) the peptide-reporter molecule should be cell permeable, therefore there should be minimum numbers of hydrophilic groups in the molecule and the size of the molecule should preferably be small; c) the peptide-reporter molecule should preferably not diffuse out of the cell once it permeates the cell membrane; d) the reporter molecule should preferably not diffuse out of the cell once it is liberated from the peptide.

The method of screening apoptosis inhibitors or inducers in whole cells vs cell-free enzyme assay can also be used for the screening of inhibitors of enzymes other than caspases. Traditionally, enzyme inhibitors were first identified by cell-free enzyme assays. Cell cultures were then used for secondary assay to assess activity of the active compounds in intact cells. A cell permeable fluorogenic or fluorescent substrate will enable the screening of inhibitors of proteases and peptidases and other enzymes directly in living whole cells. There are several advantages in whole cell assays vs cell-free enzyme assays. One of the advantages is that in whole cell assays, the inhibitor will have to penetrate the cell to be detected. Since many proteases, in living cells are regulated by other proteins, receptors or genes, screening using living cells will allow the identification of small molecule compounds which interfere with cellular proteases by binding to the active site, as well as compounds which modulate protease function by interfering with transcription, translation, biosynthesis, sub-unit assembly, cellular cofactors or signal transduction mechanisms (or viral entry into host cells, in the case of viral proteases). Furthermore, since there is an abundance of aminopeptidases in the cells, these aminopeptidases can be used in the design of fluorogenic or fluorescent substrates for whole cell assay which otherwise will not work in cell-free enzyme assays. Therefore there is a need to develop HTS assays and reagents for such assays in whole cells which can be used for drug discovery or diagnostic procedures.

AGM-1470 (also known as TNP-470) is an angiogenesis inhibitor in clinical trials for a variety of cancers. The mechanism of action of AGM-1470 was recently discovered by two independent research groups (Sin, N., et al. *Proc. Natl. Acad. Sci. USA*. 94:6099–6103 (1997); Griffith, E. C., et al, *Chem. Biol.* 4:461–471 (1997)). They found that AGM-1470 and analogs are inhibitors of methionine aminopeptidase type 2 (MetAP-2). The potency for inhibition of endothelial cell proliferation and inhibition of methionine aminopeptidase activity was determined for a series of AGM-1470 analogs and a significant correlation between the two activities was found.

Since angiogenesis inhibitors are known to be able to selectively kill cancer cells, a cellular screening assay for inhibitors of MetAP-2 may result in novel anti-cancer drugs. Therefore cell permeable fluorogenic or fluorescent substrates for MetAP-2 can be used for the screening of inhibitors of MetAP-2 in endothelial cells which could lead to novel anticancer agents.

Recently, HIV protease inhibitors such as ritonavir and viracept have been shown to be very effective in the treatment of patients infected with HIV. These inhibitors were designed based on the structure of the HIV protease substrate. The activities of these inhibitors were first determined against HIV protease. Active compounds were then tested for inhibition of HIV infection in cell cultures. A cell permeable fluorogenic or fluorescent substrate for HIV protease can be used for the screening of HIV protease inhibitors in HIV infected cells which could speed up the process for the discovery of novel HIV protease inhibitors and lead to new and better treatment for HIV infection. Since HIV protease processes viral precursor proteins at a late stage in viral replication, a cell permeable fluorogenic or fluorescent substrate for HIV protease also can be used to screen compounds which inhibit gene transcription or translation, viral entry, or other key proteins in the early stage of HIV infection. The fluorogenic or fluorescent substrates also could be used for diagnosis of HIV infection, which might be more sensitive than the currently available methods.

Applying the same principle, cell permeable fluorogenic or fluorescent substrates for cathepsin B can be used for the screening of cathepsin B inhibitors. Cell permeable fluorogenic or fluorescent substrates for dipeptidyl-peptidase IV can be used for the screening of dipeptidyl-peptidase IV inhibitors. Cell permeable fluorogenic or fluorescent substrates for renin can be used for the screening of renin inhibitors and cell permeable fluorogenic or fluorescent substrates for adenovirus protease or other viral proteases can be used for the screening of adenovirus protease or other viral protease inhibitors.

U.S. Pat. Nos. 4,557,862 and 4,640,893 disclose Rhodamine 110 derivatives as fluorogenic substrates for proteinases of the formula:

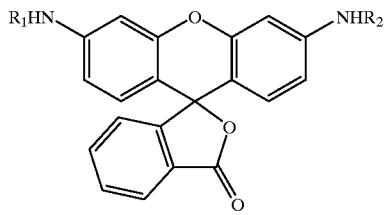

wherein $R_1$ and $R_2$, which are the same or different, are selected from the group consisting of amino acids, amino acid derivatives, blocked amino acids, blocked amino acid derivatives, and peptides. Exemplary $(AA)_2$-Rhodamines and (peptide)$_2$-Rhodamines are (Z-Arg)$_2$-Rhodamine 110, (Arg)$_2$-Rhodamine 110, (Z-Ala-Arg)$_2$-Rhodamine 110, (Z-Gln-Arg)$_2$-Rhodamine 110, (Z-Glu-Arg)$_2$-Rhodamine 110, (Z-Gly-Arg)$_2$-Rhodamine 110, (Z-Leu-Arg)$_2$-Rhodamine 110, (Z-Met-Arg)$_2$-Rhodamine 110, (Z-Phe-Arg)$_2$-Rhodamine 110, (Z-Pro-Arg)$_2$-Rhodamine 110, (Z-Trp-Arg)$_2$-Rhodamine 110, (Z-Val-Arg)$_2$-Rhodamine 110, and (Z-Ile-Pro-Arg)$_2$-Rhodamine 110.

WO 96/36729 discloses compounds or their salts for assaying the activity of an enzyme inside a metabolically active whole cell. The assay compound is said to include a leaving group and an indicator group. The leaving group is selected from the group comprising amino acids, peptides, saccharides, sulfates, phosphates, esters, phosphate esters, nucleotides, polynucleotides, nucleic acids, pyrimidines, purines, nucleosides, lipids and mixtures. The indicator group is selected from compounds which have a first state when joined to the leaving group, and a second state when the leaving group is cleaved from the indicator group by the enzyme. Preferred indicator compounds are said to be Rhodamine 110, rhodol, and fluorescein and analogs of these compounds.

U.S. Pat. No. 5,576,424 disclosed haloalkyl derivatives of reporter molecules used to analyze metabolic activity in cells of the Formula:

XR-SPACER-REPORTER-BLOCK

Wherein -BLOCK is a group selected to be removable by action of a specific analyte, to give reporter spectral properties different from those of the substrate; -REPORTER- is a molecule that, when no longer bound to BLOCK by a BLOCK-REPORTER bond, has spectral properties different from those of the substrate; -SPACER- is a covalent linkage; and XR- is a haloalkyl moiety that can covalently react with an intracellular thiol to form a thioether conjugate. Preferred reporter compounds are said to include Rhodamine-110, rhodol, fluorescein and others.

SUMMARY OF THE INVENTION

The present invention relates to fluorogenic or fluorescent reporter compounds of general Formula I:

X-Y-Z          (I)

or biologically acceptable salts or pro-reporter molecules (such as methyl or ethyl ester forms of carboxyl-containing amino acid residues) thereof, wherein X is a peptide, amino acid or other structure such that the compound of Formula I is a substrate for caspases, or other proteases or peptidases or other enzymes; and wherein X-Y is the scissile bond. Z is a halo-substituted benzoyl blocking group and the Y-Z bond is not a scissile bond. Y is a fluorogenic or fluorescent moiety, preferably a Rhodamine including, but not limited to, Rhodamine 110, Rhodamine 116, Rhodamine 19 and sulforhodamine. Most preferably Y is Rhodamine 110. Preferably Z is a multifluoro-substituted benzoyl group, and most preferably pentafluorobenzoyl and tetrafluorobenzoyl.

Preferred compounds are represented by Formula II:

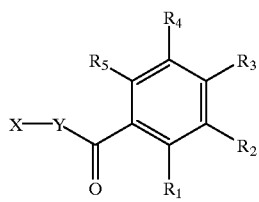

(II)

or biologically acceptable salts or pro-reporter molecules thereof, wherein X and Y are as defined above.

$R_1$–$R_5$ are independently hydrogen, fluoro, chloro, bromo, iodo, haloalkyl, aryl, cycloalkyl, alkyl, alkenyl, alkynyl, aralkyl, aralkenyl, aryl alkynyl, hydroxyalkyl, nitro, amino, cyano, acyl (alkanoyl), acylamino, hydroxy, acyloxy, alkoxy, alkylthio, or carboxy, provided that at least one of $R_1$, $R_3$ or $R_5$ is fluoro or chloro. Preferrably, three of the $R_1$–$R_5$ are fluoro, more preferably, four of the $R_1$–$R_5$ are fluoro, and most preferably, $R_1$–$R_5$ are all fluoro.

Especially preferred compounds are represented by Formula III:

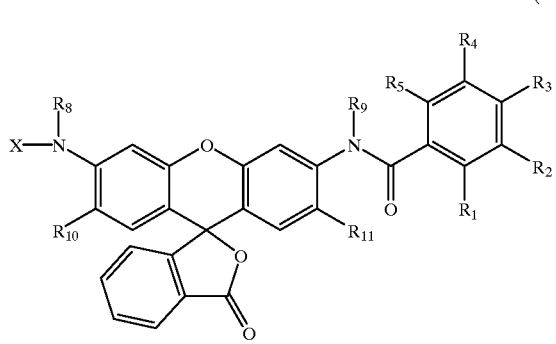

(III)

or biologically acceptable salts or pro-reporter molecules (such as methyl ester form of carboxyl-containing amino acid residues) thereof, wherein X and $R_1$–$R_5$ are as defined previously; $R_8$ and $R_9$ are the same or different and are independently hydrogen, alkyl or aryl; and $R_{10}$ and $R_{11}$ are the same or different and are independently hydrogen or alkyl.

Preferred $R_8$ and $R_9$ are hydrogen, methyl, or ethyl and $R_{10}$ and $R_{11}$ are hydrogen or methyl. Most preferably $R_8$ and $R_{11}$ are hydrogen.

Specifically, one class of the novel fluorogenic or fluorescent reporter compounds of this invention are of Formula IV:

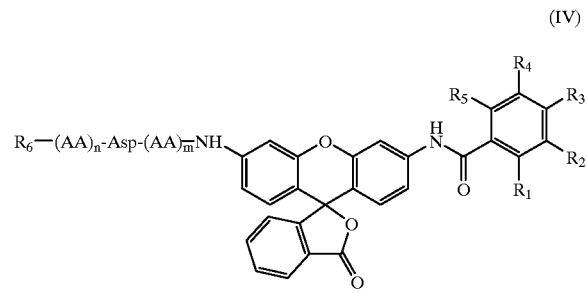

(IV)

or biologically acceptable salts or pro-reporter molecules thereof, wherein: $R_1$–$R_5$ are as defined previously in Formula II; and $R_6$ is a N-terminal protecting group, e.g. t-butyloxycarbonyl, acyl, benzyloxycarbonyl and pentafluorobenzoyl. Each AA independently is any natural or non-natural amino acid or derivative of an amino acid. Preferably, n is an integer from 0–5 and m is an integer from 0–3.

Another class of the novel fluorogenic or fluorescent reporter compounds of this invention are of Formula V:

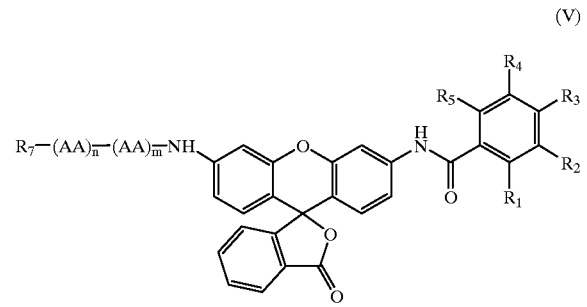

(V)

or biologically acceptable salts or pro-reporter molecules thereof, wherein: $R_1$–$R_5$, AA, n and m are as defined previously in Formulae II and IV; and $R_7$ is a N-terminal protecting group including t-butyloxycarbonyl, acyl, benzyloxycarbonyl and pentafluorobenzoyl. $R_7$ may also be H.

The invention also relates to a method for the preparation of a Gly-containing compound of Formula IV, comprising the steps of:

(a) reacting Rhodamine with a compound of Formula (VI)

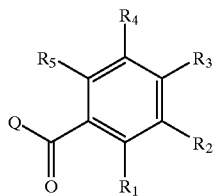

(VI)

wherein $R_1$–$R_5$ are defined above and Q is halo, hydroxy or a group of Formula VII:

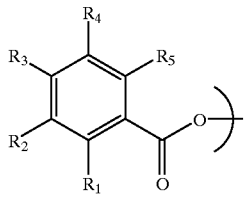

(VII)

where $R_1$–$R_5$ defined above,
to give the substituted benzoyl-Rhodamine of Formula VIII;
  (b) condensing the substituted N-benzoyl-Rhodamine together with N-Z-Gly to give N-Z-Gly-N'-substituted benzoyl-Rhodamine;
  (c) removing the Z group to give N-Gly-N'-substituted benzoyl-Rhodamine;
  (d) condensing N-Gly-N'-substituted benzoyl-Rhodamine with Z-$(AA)_n$-Asp(OBu-t) to give N-(Z-$(AA)_n$-Asp(OBu-t)-Gly)-N'-substituted benzoyl-Rhodamine; and
  (e) removing the OBu-t protecting group to give N-(Z-$(AA)_n$-Asp-Gly)-N'-substituted benzoyl-Rhodamine.

In a preferred embodiment, the substituted benzoyl group is pentafluoro substituted.

Alternatively, the step introducing Gly may be omitted and a compound of general Formula IV can be obtained by a method comprising the steps of:
  (a) reacting Rhodamine with a compound of Formula VI to give N-substituted benzoyl-Rhodamine of Formula VIII;
  (b) condensing the substituted N-benzoyl-Rhodamine with Z-$(AA)n$-Asp(-OBu-t) to give N-(Z-$(AA)n$-Asp(OBu-t))-N'-substituted benzoyl-Rhodamine; and
  (c) removing the OBu-t protecting group to give N-(Z-$(AA)_n$-Asp)-N'-substituted benzoyl-Rhodamine.

In this embodiment, where $(AA)_n$ includes amino acids such as glutamic acid or aspaartic acid, the carboxy group may be protected as an OBu-t group which is cleaved in the last step.

Thus, the invention also relates to the novel fluorescent dyes of Formula VIII which are derivatives of Rhodamine by introducing a fluoro- or chloro-substituted benzoyl blocking group into one of the two amino groups of Rhodamine. The HN-$R_8$ group in Formula VIII provides the point of attachment for reaction with a potential enzyme substrate, such as the carboxylic group of a N-protected peptide, to form a peptide amide bond. The reaction will convert the fluorescent molecule of Formula VIII into a non-fluorescent peptide-reporter molecule of Formulae IV or V which is a substrate for proteases or peptidases. Cleavage of the scissile peptide-reporter amide bond in peptide-reporter by proteases or peptidases produces compound of Formula VIII or VIII' which is fluorescent.

Specifically, the novel fluorescent dyes of this invention are of Formula VIII:

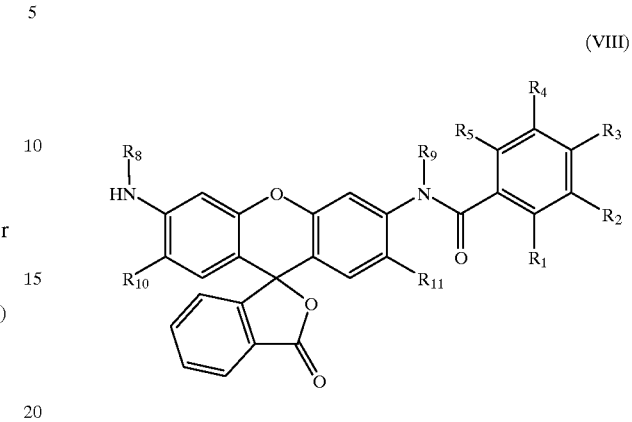

(VIII)

or biologically acceptable salts wherein $R_1$–$R_5$ are as defined previously in Formula II; $R_8$–$R_{11}$ are as defined previously in Formula III. Preferrably, three of the $R_1$–$R_5$ are fluoro, more preferably, four of the $R_1$–$R_5$ are fluoro, and most preferably, $R_1$–$R_5$ are all fluoro. Preferrably, $R_8$–$R_{11}$ are hydrogen or alkyl. Most preferably, $R_8$–$R_{11}$ are all hydrogen.

Compounds of Formula VIII of the present invention may exist in tautomeric forms, particularly the ring opening form of Formula VIII'. The invention includes all tautomeric forms including, but not limited to, VIII and VIII'.

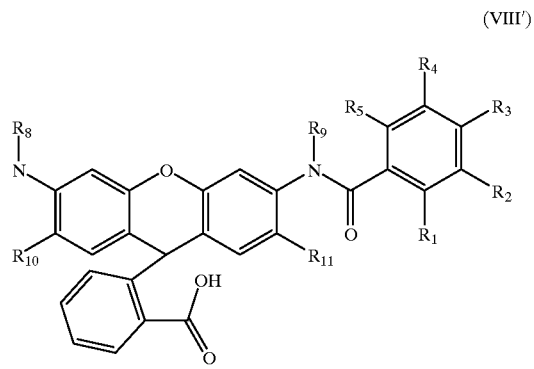

(VIII')

The invention also relates to a process of using the reporter compounds represented by Formula IV to measure the activity of intracellular caspases or other enzymes involved in apoptosis in living or dead whole cells or tissues. The invention also relates to methods of using the compounds represented by Formula IV and the assay processes described herein to measure the activation or inhibition of any of the caspase enzymes inside any living or dead whole cell or tissue (normal or cancerous) by a test substance or substances. The compounds represented by Formula IV are cell-permeable, that is they can be introduced into whole cells or tissue samples. The compounds are fluorogenic or fluorescent and can be designed to be specific for any of the known caspases or for any other intracellular enzymes involved in apoptosis.

Thornberry, N. A., et al., *J. Biol. Chem.* 272:17907 (1997), describe the optimal sequences for various caspase substrates and for the Granzyme B substrate. The optimal substrate sequences are shown in Table 1.

TABLE 1

| Enzyme* | Optimal Sequence** |
|---|---|
| caspase-1 (ICE) | WEHD (SEQ ID NO:1) |
| caspase-2 (ICH-1, mNEDD2) | DEHD (SEQ ID NO:6) |
| caspase-3 (apopain, CPP-32, YAMA) | DEVD (SEQ ID NO:5) |
| caspase-4 ($ICE_{re}II$, TX, ICH-2) | (W/L)EHD (SEQ ID NO:25) |
| caspase-5 ($ICE_{re}III$, TY) | (W/L)EHD (SEQ ID NO:25) |
| caspase-6 (Mch2) | VEHD (SEQ ID NO:7) |
| caspase-7 (Mch-3, ICE-LAP3, CMH-1) | DEVD (SEQ ID NO:5) |
| caspase-8 (MACH, FLICE, Mch5) | LETD (SEQ ID NO:8) |
| caspase-9 (ICE-LAP6, Mch6) | LEHD (SEQ ID NO:3) |
| granzyme B | IEPD (SEQ ID NO:23) |

*Enzymes are identified by both new and old (in parentheses) nomenclature.
**Standard one-letter abbreviations for amino acids are used to indicate the optimal amino acid sequences.

Using the optimal sequences described by Thornberry et al., fluorogenic or fluorescent substrates for specific caspases can be synthesized by the procedures described herein.

It is also possible to design other fluorogenic or fluorescent substrates for known or unknown caspases or other enzymes by utilizing known or potential cleavage site peptide sequences from known or potential natural substrates of caspase or other enzymes. Table 2 depicts peptide sequences corresponding to known or potential cleavage sites in proteins that may be natural substrates for caspases.

TABLE 2

| Enzyme | Substrate | Cleavage Sequence* |
|---|---|---|
| caspase-3 | PARP | DEVD (SEQ ID NO:5) |
| | PAK2 | SHVD (SEQ ID NO:10) |
| | D4-GDI | DBLD (SEQ ID NO:11) |
| | U1-70kDa | DGPD (SEQ ID NO:12) |
| | SREBP | DEPD (SEQ ID NO:13) |
| | DNA-PK | DEVD (SEQ ID NO:5) |
| | huntingtin | DGTD (SEQ ID NO:14) |
| | | DLND (SEQ ID NO:15) |
| | | DEED (SEQ ID NO:16) |
| | | DSLD (SEQ ID NO:17) |
| | mdm2 | DVPD (SEQ ID NO:18) |
| caspase-3 + other unknown caspases | fodrin | DETD (SEQ ID NO:4) |
| possibly caspase-3 | Rb | DEAD (SEQ ID NO:19) |
| possibly caspase-3 | presenilins | DSYD (SEQ ID NO:20) |
| ? | actin | ELPD (SEQ ID NO:21) |
| caspase-6 | lamin A | VEID (SEQ ID NO:26) |
| caspase-8 | CPP32 | IETD (SEQ ID NO:24) |

*Standard one-letter abbreviations for amino acids are used to indicate the amino acid sequences.

The fluorogenic or fluorescent substrates can also be designed to measure more than one enzyme at a time, by designing substrates that are recognized and cleaved by more than one of the enzymes involved in the caspase cascade. Fluorogenic or fluorescent substrates which are "promiscuous" for more than one caspase may be utilized using the assay process described herein to measure the activity of as yet unknown caspases.

When the caspase cascade is activated by a cell-death inducing stimulus, the fluorogenic or fluorescent reporter molecules described herein are cleaved and respond with a large increase in fluorescence emission. The change in fluorescence can be measured spectrofluorometrically. The reporter molecules can also be used to measure baseline caspase activity in cells that are not undergoing apoptosis. The method is easily adaptable to high throughput or ultra-high throughput screening assays.

The assay system is very versatile. Examples of the extreme versatility of the assay system are given below:

1) The assay can be used to screen a cell or tissue for baseline activity of any caspase enzyme or any other enzyme involved in apoptosis.
2) The assay can be used with equal ease to screen for compounds that can either activate or inhibit the caspase cascade. That means the assay can be used to screen for drugs against degenerative diseases or for drugs against cancer.
3) The assay can be used to screen for caspase cascade activation or inhibition in any living or dead cells or cell lines derived from any organ system in the body including, but not limited to, hair, brain, peripheral nervous system, eye, ear, nose, mouth, tonsils, teeth, esophagus, lung, heart, blood, blood vessels, bone marrow, lymph nodes, thymus, spleen, immune system, liver, stomach, intestinal tract, pancreas, endocrine glands and tissues, kidney, bladder, reproductive organs and glands, joints, bones and skin. The assay can be used to screen for drugs with potential use in any disease of any organ system in the body that involves malfunction of the caspase cascade.
4) The assay can be used to screen for drugs that might modulate the caspase cascade directly or indirectly, i.e. by modulating the caspases itself or by modulating cellular receptors and co-factors that influence the caspase cascade.
5) The assay can be used to determine the site of action at which a caspase cascade modulator interferes. That is, the assay can help to pin down the molecular mechanism of action of a novel caspase cascade modulator drug.

The invention also relates to the use of the fluorogenic or fluorescent substrates represented by Formula IV for finding new compounds or new uses for known compounds in reducing, preventing or treating maladies in which apoptotic cell death is either a causative factor or a result. Examples of uses for the present invention include screening for compounds that can protect the nervous system following focal ischemia and global ischemia; screening for compounds that can treat neurodegenerative disorders such as Alzheimer's disease, Huntington's Disease, prion diseases, Parkinson's Disease, multiple sclerosis, amyotrophic lateral sclerosis, ataxia, telangiectasia, and spinobulbar atrophy; screening for compounds that can treat heart disease including myocardial infarction, congestive heart failure and cardiomyopathy; screening for compounds that can treat retinal disorders; screening for compounds that treat autoimmune disorders including lupus erythematosus, rheumatoid arthritis, type I diabetes, Sjögren's syndrome and glomerulonephritis; screening for compounds that treat polycystic kidney disease and anemia/erythropoiesis; screening for compounds that treat immune system disorders, including AIDS and SCIDS; screening for compounds that reduce or prevent cell, tissue and organ damage during transplantation (e.g. graft versus host disease in bone marrow transplantation procedures); screening for compounds that reduce or prevent cell line death in industrial biotechnology; screening for compounds that reduce or prevent alopecia (hair loss); and screening for compounds that reduce the premature death of skin cells.

The present invention also relates to the use of the fluorogenic or fluorescent substrates represented by Formula IV in screening procedures where libraries of known drugs or combinatorial or other compound libraries are screened for compounds with anti-tumor or anti-cancer activity. The cancer cells or cell lines can be derived from any cancer of any internal or external organ system in the body including, but not limited to brain, peripheral nervous system, eye, ear, nose, mouth, tonsils, teeth, esophagus, lung, heart, blood, blood vessels, bone marrow, lymph nodes, thymus, spleen, immune system, liver, stomach, intestinal tract, pancreas, endocrine glands and tissues, kidney, bladder, reproductive organs and glands (e.g. prostate gland), joints, bones and skin.

The present invention also relates to the use of the fluorogenic or fluorescent substrates represented by Formula I in diagnostic procedures to determine the chemosensitivity or resistance of cancer cells taken from an animal or a human being to treatment with chemotherapeutic drugs. The cancer cells or cell lines can be derived from any cancer of any internal or external organ system in the body including, but not limited to brain, peripheral nervous system, eye, ear, nose, mouth, tonsils, teeth, esophagus, lung, heart, blood, blood vessels, bone marrow, lymph nodes, thymus, spleen, immune system, liver, stomach, intestinal tract, pancreas, endocrine glands and tissues, kidney, bladder, reproductive organs and glands (e.g. prostate gland), joints, bones and skin.

In particular, the invention relates to a method for detecting an enzyme involved in the apoptosis cascade in one or more cells, comprising (a) contacting the one or more cells with a reporter compound according to the invention under conditions whereby the reporter compound is taken into said one or more cells, and (b) recording the fluorescence of said one or more cells, wherein a change in fluorescence, either of magnitude or of wave length, within the one or more cells compared to control cells which have not been so contacted or one that has been contacted with the reporter compound and a known competitive inhibitor of the enzyme, is an indication of the presence of the enzyme.

The invention also relates to a method for measuring the activity of an enzyme involved in the apoptosis cascade in one or more cells, comprising (a) contacting the one or more cells with the reporter compound according to the invention under conditions whereby said reporter compound is taken into the one or more cells, and (b) recording the fluorescence of the one or more cells, wherein the relative change in fluorescence, either of magnitude or of wave length within the one or more cells, compared to control cells which have not been so contacted or one that has been contacted with the reporter compound and a known competitive inhibitor of the enzyme, is a measure of the activity of the enzyme.

The invention also relates to a method for determining whether a test substance has an effect on an enzyme involved in the apoptosis cascade in one or more test cells, comprising (a) contacting the one or more test cells with the test substance and the reporter compound according to the invention under conditions whereby the reporter compound is taken into the one or more cells and the test substance either interacts with an external membrane receptor or is taken into said cells, and (b) recording the fluorescence of the test cells, wherein a change in fluorescence, either of magnitude or of wavelength, within the cells compared to the control cells which have only been contacted with the reporter compound and not with the test substance, is an indication that the test substance has an effect either directly or indirectly on the apoptosis enzyme being tested.

In the practice of this aspect of the invention, the test cells may be contacted with said test substance prior to, after, or substantially simultaneously with the reporter compound according to the invention. The method may be used to detect whether the test substance stimulates or inhibits the activity of the enzyme.

The invention also relates to further contacting the test cells with a second test substance or mixture of test substances in the presence of the first test substance.

In a preferred embodiment, the test cell is a cancer cell or cell line derived from a human in need of treatment with a chemotherapeutic drug and the test substance is a chemotherapeutic agent or a mixture of chemotherapeutic agents.

The invention also relates to a method to determine the sensitivity of an animal with cancer to treatment with one or more chemotherapeutic agents, comprising (a) contacting cancer cells taken from said animal with one or more chemotherapeutic agents and the reporter compound according to the invention under conditions whereby the reporter compound is taken into the cancer cells and the one or more agents either interact with an external membrane receptor of said cell or are taken into said cell, and (b) recording the fluorescence of the cancer cells, wherein a change in fluorescence, either of magnitude or of wavelength, within the cancer cells compared to contol cells which have only been contacted with the reporter compound, compared to control cells is an indication that the cancer cells are chemosensitive to the one or more agents and that the animal is sensitive to the treatment.

The invention also relates to a method of monitoring the treatment of an animal with one or more chemotherapeutic drugs, comprising (a) administering one or more chemotherapeutic drugs to the animal, (b) contacting cells taken from the animal with the reporter compound according to the invention under conditions whereby the reporter compound is taken into the cells, and (c) recording the fluorescence of the cells contacted with the reporter compound, wherein a change in fluorescence, either of magnitude or of wavelength, within the cells taken from the animal after the administering compared to the control cells which have been taken from the animal before the administration is an indication that the animal is sensitive to the chemotherapeutic agent. In this embodiment, the animal may suffer from a malady in which apoptotic cell death is either a causative factor or a result.

The invention also relates to a method for determining whether a test substance inhibits or prevents cell death in one or more test cells, comprising (a) contacting the test cell with the test substance and the reporter compound according to the invention under conditions whereby the test substance either interacts with an external membrane receptor or is taken into the cell and the reporter compound is taken into the cell, and (b) recording the fluorescence of the test cells, wherein a change in fluorescence, either of magnitude or of wavelength, within the test cells compared to control cells that have only been contacted with the reporter compound, is an indication that the test substance inhibits or prevents cell death.

The invention also relates to a method for determining whether a test substance causes or enhances cell death in one or more test cells, comprising the steps of:

(a) contacting the test cells with the test substance and the reporter compound according to the invention under conditions whereby the test substance either interacts with an external membrane receptor or is taken into the cells and the reporter compound is taken into the cells, (b) recording the fluorescence of the test cells, wherein a change in fluorescence, either of magnitude or of wavelength, within the test cells compared to control cells which have only been contacted with the reporter compound, is an indication that the test substance causes or enhances cell death.

The invention also relates to a process of using the reporter compounds represented by Formula V to measure the activity of intracellular peptidases and proteases in living whole cells, including, but not limited to, type-2 methionine aminopeptidase in endothelial cells and HIV protease in HIV infected cells. The invention also relates to methods of using the compounds represented by Formula V and the assay processes described herein to measure the inhibition of enzymes inside living whole cell by a test compound or compounds. The reporter compounds represented by Formula V are cell-permeable, that is they can be introduced into whole cells. The compounds are fluorogenic or fluorescent and can be designed to be specific for the known enzymes of interest, such as methionine aminopeptidase or HIV protease.

DETAILED DESCRIPTION OF THE INVENTION

Figure 1:
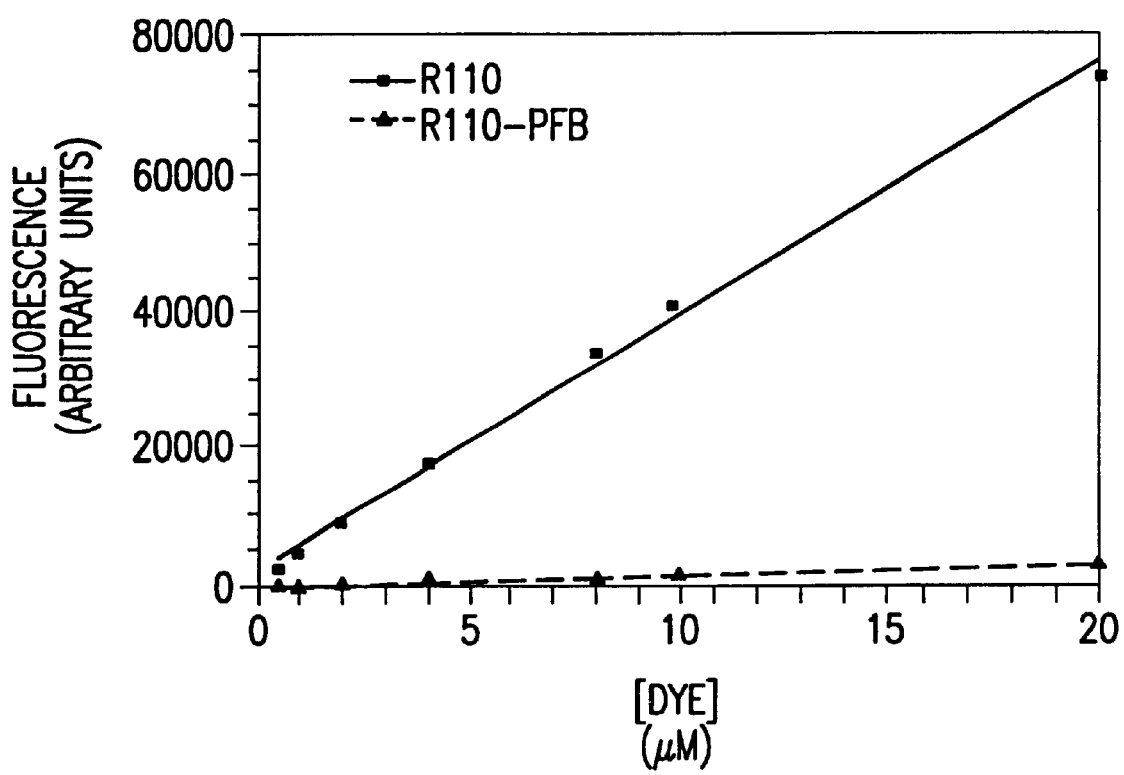
FIG. 1 depicts a graph showing the fluorescence of N-pentafluorobenzoyl-Rhodamine 110 (R110-PFB) compared to Rhodamine 110 (R110).

The fluorogenic or fluorescent substrates of the present invention are compounds having the general Formula I:

X-Y-Z　　　　(I)

or biologically acceptable salts or pro-reporter molecules (such as methyl ester form of carboxyl-containing amino acid residues) thereof, wherein X is a peptide, amino acid or other structure such that compounds of Formula I is a substrate for a caspase or other proteases or peptidases or other enzymes; and wherein X-Y is a scissile bond. Y is a fluorogenic or fluorescent moiety, preferably a Rhodamine including, but not limited to, Rhodamine 110, Rhodamine 116, Rhodamine 19 and sulfonorhodamine and most preferably Rhodamine 110. Z is a halo-substituted benzoyl blocking group and the Y-Z bond is not a scissile bond. Preferably Z is a multifluoro-substituted benzoyl group and most preferably Z is a tetrafluoro or pentafluorobenzoyl group.

Preferred compounds falling within the scope of Formula I include compounds wherein the first amino acid attached to Y is an Asp. Most preferably, X is a N-blocked tetrapeptide substrate of a caspase including WEHD SEQ ID NO:1, YVAD SEQ ID NO:2, LEHD SEQ ID NO:3, DETD SEQ ID NO:4, DEVD SEQ ID NO:5, DEHD SEQ ID NO:6, VEHD SEQ ID NO:7, LETD SEQ ID NO:8, SHVD SEQ ID NO:10, DELD SEQ ID NO:11, DGPD SEQ ID NO:12, DEPD SEQ ID NO:13, DGTD SEQ ID NO:14, DLND SEQ ID NO:15, DEED SEQ ID NO:16, DSLD SEQ ID NO:17, DVPD SEQ ID NO:18, DEAD SEQ ID NO:19, DSYD SEQ ID NO:20, ELPD SEQ ID NO:21, VEID SEQ ID NO:26, IETD SEQ ID NO:24, or a N-blocked tetrapeptide substrate of granzyme B including IEPD SEQ ID NO:23 and VEPD SEQ ID NO:27; or X is a N-blocked peptide which corresponds to a carboxyterminal or aminoterminal fragment consisting of 1,2 or 3 amino acids of the tetrapeptide substrate of a caspase including WEHD SEQ ID NO:1, YVAD SEQ ID NO:2, LEHD SEQ ID NO:3, DETD SEQ ID NO:4, DEVD SEQ ID NO:5, DEHD SEQ ID NO:6, VEHD SEQ ID NO:7, LETD SEQ ID NO:8, SHVD SEQ ID NO:10, DELD SEQ ID NO:11, DGPD SEQ ID NO:12, DEPD SEQ ID NO:13, DGTD SEQ ID NO:14, DLND SEQ ID NO:15, DEED SEQ ID NO:16, DSLD SEQ ID NO:17, DVPD SEQ ID NO:18, DEAD SEQ ID NO:19, DSYD SEQ ID NO:20, ELPD SEQ ID NO:21, VEID SEQ ID NO:26, IETD SEQ ID NO:24 and granzyme B including IEPD SEQ ID NO:23 and VEPD SEQ ID NO:27; or X is a N-blocked peptide which corresponds to a carboxyterminal or aminoterminal fragment consisting of 1, 2, 3 or 4 amino acids of the tetrapeptide substrate of a caspase including WEHD SEQ ID NO:1, YVAD SEQ ID NO:2, LEHD SEQ ID NO:3, DETD SEQ ID NO:4, DEVD SEQ ID NO:5, DEHD SEQ ID NO:6, VEHD SEQ ID NO:7, LETD SEQ ID NO:8, SHVD SEQ ID NO:10, DELD SEQ ID NO:11, DGPD SEQ ID NO:12, DEPD SEQ ID NO:13, DGTD SEQ ID NO:14, DLND SEQ ID NO:15, DEED SEQ ID NO:16, DSLD SEQ ID NO:17, DVPD SEQ ID NO:18, DEAD SEQ ID NO:19, DSYD SEQ ID NO:20, ELPD SEQ ID NO:21, VEID SEQ ID NO:26, IETD SEQ ID NO:24 and granzyme B including IEPD SEQ ID NO:23 and VEPD SEQ ID NO:27, plus 1–2 amino acids corresponds to the $P_1'$–$P_2'$ portion of the substrate of a caspase including G, A, GA, GG and AG.

In particular, preferred embodiments of the compounds of Formula I are represented by Formula II:

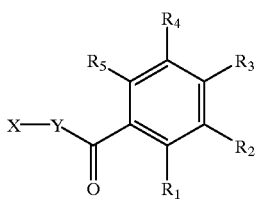
(II)

or biologically acceptable salts or pro-reporter molecules thereof, wherein X and Z are as defined previously in Formula I;

$R_1$–$R_5$ are independently hydrogen, fluoro, chloro, bromo, iodo, haloalkyl, aryl, cycloalkyl, alkyl, alkenyl, alkynyl, aralkyl, aralkenyl, aralkynyl, hydroxyalkyl, nitro, amino, cyano, acylamino, acyl, hydroxy, acyloxy, alkoxy, alkylthio, or carboxy; provided that at least one of the $R_1$, $R_3$ or $R_5$ is fluoro or chloro. Preferrably, three of the $R_1$–$R_5$ are fluoro, more preferably, four of the $R_1$–$R_5$ are fluoro, and most preferably, $R_1$–$R_5$ are all fluoro.

Especially preferred embodiments of the compounds of Formula I are represented by Formula III:

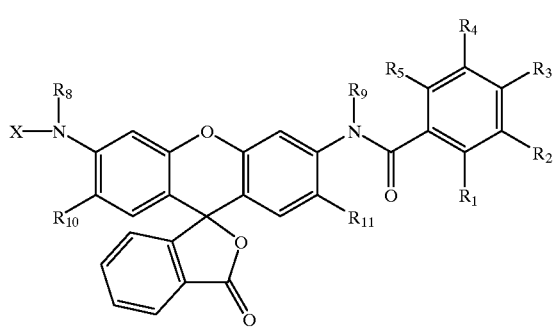
(III)

or biologically acceptable salts or pro-reporter molecules thereof, wherein X and $R_1$–$R_5$ are as defined previously in Formulae I and II; and $R_8$ and $R_9$ are the same or different and are independently hydrogen, alkyl or aryl; and $R_{10}$ and $R_{11}$ are the same or different and are independently hydrogen or alkyl.

Preferably $R_8$ and $R_9$ are hydrogen, methyl or ethyl. Preferably $R_{10}$ and $R_{11}$ are hydrogen or methyl. Most preferably $R_8$ and $R_{11}$ are hydrogen.

The fluoro- or chloro-substituted benzoyl group in Formula III is introduced to block one of the two amino groups in a Rhodamine. The remaining $HNR_8$ group is used for reaction with a potential enzyme substrate X, to give a fluorogenic substrate of Formula III. By blocking one of the two amino groups in a Rhodamine, the overall size of the substrate is reduced compared to a bis-substituted Rhodamine, such as a bis-peptide-Rhodamine. More importantly, the fluoro- or chloro-substituted benzoyl group also increases the lipophilicity of the molecule, thus increasing cell permeability of the substrates of Formula III. In addition, the presence of the carbonyl group, together with other electron withdrawing groups present in the benzoyl group, activate the ring so that the fluoro or chloro groups on the ring may be replaced by a nucleophile inside the cells, such as a thiol, amino or hydroxyl group from proteins or peptides. This will result in the accumulation of the substrates inside the cells, as well as retention of the fluorescent moiety of the substrate inside the cells after cleavage of the X-N bond in Formula III by the targeted enzymes. Furthermore, replacement of the fluoro or chloro group by a nucleophile also results in the replacement of the electron withdrawing fluoro or chloro group by an electron donating group such as sulfide, amino or ether, or the replacement of the fluoro or chloro group by a highly hydrophilic moiety such as glutathion, which can change the fluorescent intensity or wavelength of the fluorogenic or fluorescent moiety of the substrates.

Specifically, one class of the novel fluorogenic or fluorescent reporter compounds of this invention are of Formula IV:

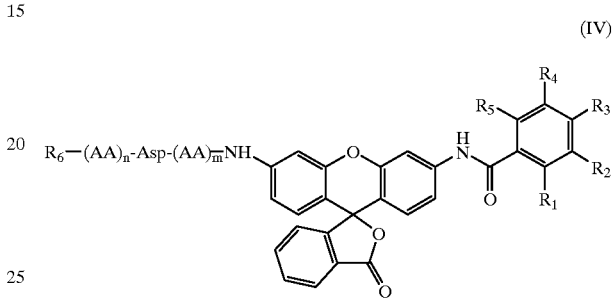
(IV)

or biologically acceptable salts or pro-reporter molecules thereof, wherein: $R_1$–$R_5$ are as defined previously in Formula II; and $R_6$ is a N-terminal protecting group, e.g., t-butyloxycarbonyl, acyl, benzyloxycarbonyl and pentafluorobenzoyl; each AA independently is a residue or derivative of any natural or non-natural amino acid; n is 0–5; and m is 0–3.

Preferably $R_6$ is t-butyloxycarbonyl, benzyloxycarbonyl, acetyl, octanoyl, dodecanoyl or pentafluorobenzoyl.

Compounds of Formula IV are novel fluorogenic or fluorescent substrates for caspases or other enzymes related with apoptosis. When m is 0, cleavage of the amide bond between Asp and Rhodamine will convert the fluorogenic substrate into the fluorescent dye of Formula VIII. When m is not 0, cleavage of the amide bond between Asp and $(AA)_m$ will leave the Rhodamine attached to $NH_2$-$(AA)_m$. The remaining amino acids $(AA)_m$ will then be removed by aminopeptidases present in the cells to give the fluorescent dye of Formula VIII. $(AA)_m$ may be designed to correspond with the P' sequence of the cleavage site of substrates of caspases or apoptosis related enzymes. The incorporation of the P' sequence of known substrates of caspases or apoptosis related enzymes are expected to increase specificity and affinity of the fluorogenic substrates. Since aminopeptidases are widely present in cells, one can insert a $(AA)_m$ sequence in the design of substrates of Formula IV for whole cell assays. This is another advantage of whole cell assays over cell-free enzyme assays. For instance, when $(AA)_m$ is Gly, a substrate of Formula IV will work in whole cell assays but otherwise will not work in cell-free caspase assay because cleavage of Asp-Gly amide bond will leave the Gly attached to the Rhodamine, which is not fluorescent.

An example of a pro-reporter molecule is the methyl or ethyl ester forms of carboxyl-containing amino acid residues comprising compounds of Formula IV. Another example of a pro-reporter molecule is the acetoxymethyl (AM) or pivaloyloxymethyl (PM) ester form of carboxyl-containing amino acid residues of compounds of Formula IV. AM esters of carboxyl-containing compounds are known to be cell permeable and can be hydrolyzed by esterases inside the cells. Once hydrolyzed, the carboxyl-containing compounds become cell impermeable and are trapped inside the cells (Adams et al., *J. Am. Chem. Soc.* 111:7957–7968 (1989)). AM esters can be prepared by reacting the corresponding carboxy-containing compounds with bromomethyl acetate.

Another class of the novel fluorogenic or fluorescent reporter compounds of this invention are of Formula V:

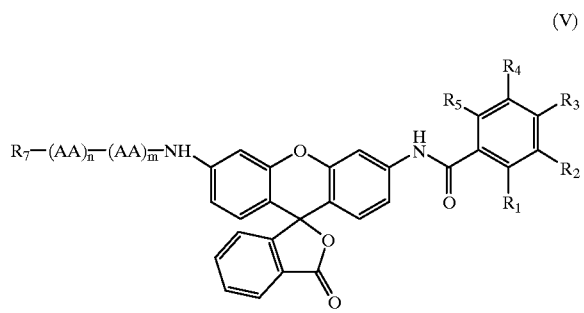

(V)

or biologically acceptable salts or pro-reporter molecules thereof, wherein: $R_1$–$R_5$ and AA are as defined previously in Formula II and IV; n is 1–5; m is 0–3; $R_7$ is a H; or $R_7$ is a N-terminal protecting group, preferably t-butyloxycarbonyl, acyl, acetyl, octanoyl, dodecanoyl, benzyloxycarbonyl or pentafluorobenzoyl.

In Formula V, $(AA)_n$ is designed to be an amino acid or a peptide which is recognized by a specific peptidase or protease as the sequence in the p side and will be cleaved by the targeted peptidase or protease. $(AA)_m$ is designed to be an amino acid or peptide which is recognized by a specific peptidase or protease as the sequence in the P' side, and which can be removed by aminopeptidases presented in the cells. When $R_7$ is a N-terminal protecting group such as a t-butyloxycarbonyl, Cbz or acetyl, compounds of Formula V are substrates for endopeptidases such as cathepsin D or protease such as HIV protease; when $R_7$ is H, compounds of Formula V are substrates for exopeptidases such as methionine aminopeptidase.

Specifically, compounds of Formula V may be designed to be substrates of type 2 methionine aminopeptidase (MetAP-2). MetAP-2 was identified recently by two research groups (Griffith, E. C., et al., *Chem. Biol.* 4:461–471 (1997) and Sin, N., et al., *Proc. Natl. Acad. Sci. USA* 94:6099–6103 (1997)) to be the commom target of angiogenesis inhibitor AGM-1470, an anti-cancer drug currently undergoing clinical trials. MetAP-2 is a bifunctional enzyme which also regulate protein synthesis by affecting the phosphorylaton state of eIF-2. AGM-1470 is reported to only inhibit the aminopeptidase activity of MetAP-2 and have no effect on the regulatory activity of MetAP-2 (Griffith, E. C., et al., *Chem. Biol.* 4:461–471 (1997)). Since angiogenesis inhibitor such as AGM-1470 is known to be able to selectively kill cancer cells, inhibitors of MetAP-2 are expected to have anti-angiogenic properties and to be potential novel anticancer agents.

MetAP-2 is a cobalt-dependent enzyme that hydrolyzes the amino-terminal methionine from certain proteins. Its preferred substrates are Met-X-Y. X is an amino acid with small and uncharged side groups, such as Gly, Ala, Ser, Leu, Met, Arg and Tyr are known to result in inactive substrates. Y can be Ser, Met, Gly or other amino acids (Li, X. & Chang Y.-H., *Biochem. Biophy. Res. Com.* 227:152–159 (1996)). Since Rhodamine is much larger than an amino acid, a compound with methionine directly attached to Rhodamine most probably will not be a substrate for MetAP-2. Taking advantage of the presence of aminopeptidase in whole cells, the insertion of a $(AA)_m$ sequence between methionine and Rhodamine will make a good substrate for MetAP-2. This type of substrate is expected to work well in a whole cell assay but otherwise will not work in a cell-free MetAP-2 enzyme assay.

For compounds of Formula V designed to be substrates of MetAP-2, preferred $R_7$ is H, preferred $(AA)_n$ is Met, and preferred $(AA)_m$ is Gly, Ala, Gly-Gly, Ala-Gly or Gly-Ala. The methionine will be cleaved by type 2 methionine aminopeptidase in endothelial cells to give the Rhodamine attached to $(AA)_m$. Aminopeptidases present inside the cells will then remove the $(AA)_m$ to give the fluorescent dye of Formula VI. Compounds of Formula V will be used for the screening of inhibitors of MetAP-2 in endothelial cells, which is expected to lead to the identification of novel anti-cancer drugs.

Compounds of Formula V also can be designed to be substrates of HIV protease. HIV protease is an aspartic protease which processes polypeptides transcribed from the gag and pol genes and is essential for the maturation of infectious virus. Therefore HIV protease has been one of the major targets for chemotherapeutic intervention of HIV. Recently, several HIV protease inhibitors have shown great potential in the treatment of HIV and have been approved for marketing. Most of these HIV protease inhibitors were designed based on the structure of the substrates of the protease. Therefore these compounds are either peptides or peptidomimetics. The search for new and novel HIV protease inhibitors is expected to provide more efficacious drugs for the fight against this deadly disease.

The preferred substrates of HIV protease are peptides with a scissile hydrophobic-hydrophobic or aromatic-proline peptide bond between the $P_1$–$P_1$' (West, M. L., and Fairlie, D. P., *Trand. Pharm. Sci.* 16:67–74 (1995)). Nine distinct sites in the viral gag and gag-pol proteins have been found to be cleaved by the protease (Martin, J. A., et al., *Prog. Med. Chem.* 32:239–287 (1995)). The $P_4$-$P_3$' sequences of these nine sites are Ser-Gln-Asn-Tyr-Pro-Ile-Val SEQ ID NO:28, Ala-Arg-Val-Leu-Ala-Glu-Ala SEQ ID NO:29, Ala-Thr-Ile-Met-Met-Gln-Arg SEQ ID NO:30, Arg-Gln-Ala-Asn-Phe-Leu-Gly SEQ ID NO:31, Pro-Gly-Asn-Phe-Leu-Gln-Ser SEQ ID NO:32, Ser-Phe-Ser-Phe-Pro-Gln-Ile SEQ ID NO:33, Thr-Leu-Asn-Phe-Pro-Ile-Ser SEQ ID NO:34, Ala-Glu-Thr-Phe-Tyr-Val-Asp SEQ ID NO:35 and Arg-Lys-Val-Leu-Phe-Leu-Asp SEQ ID NO:36. Many fluorogenic, radioactive, or chromogenic substrates of HIV protease have been prepared based on these natural substrates for HIV protease activity assays. An intramolecularly quenched fluorogenic substrate, 2-aminobenzoyl-Thr-Ile-Nle-(4-$NO_2$-Phe)-Gln-Arg-$NH_2$ SEQ ID NO:79, wherein the scissile bond is the Nle-(4-$NO_2$-Phe), was prepared based on the p24/p15 cleavage site-derived hexapeptide substrate (Toth, M. V., and Marshall, G. R., *Int. J. Pept. Protein Res.* 36:544–550 (1990)). A fluorometric assay for HIV-protease activity using HPLC with the substrate N-Dns-Ser-Gln-Asn-Tyr-Pro-Ile-Val SEQ ID NO:28 were reported by Tamburini et al. (Tamburini, P. P., et al., *Anal. Biochem.* 186:363–368 (1990)), wherein the Tyr-Pro is the scissile bond. Many other HIV protease substrates incorporating sequences from both the P side and P' side of the cleavage sites of HIV protease substrates have been developed, and these include the fluorogenic N-alpha-benzoyl-Arg-Gly-Phe-Pro-MeO-beta-naphthylamide SEQ ID NO:37, which contains the Phe-Pro dipeptide bond recognized by HIV-1 protease (Tyagi, S. C., and Carter, C. A., *Anal. Biochem.* 200:143–148 (1992)); the radiolabeled heptapeptide substrate, [tyrosyl-3,5-$^3$H]Ac-Ser-Gln-Asn-Tyr-Pro-Val-Val-NH$_2$ SEQ ID NO:38, which is based on the p17–p24 cleavage site Tyr-Pro found in the viral polyprotein substrate Pr55gag (Hyland, L. J., et al., *Anal. Biochem.* 188:408–415 (1990)); the angiotensin I-based peptide Asp-Arg-Val-Tyr-Ile-His-Pro-Phe-His-Leu-Leu-Glu-Glu-Ser SEQ ID NO:39, which yields angiotensin I (Ang I) and Leu-Glu-Glu-Ser SEQ ID NO:40 (Evans, D. B., et al.,*Anal. Biochem.* 206:288–292 (1992)); the intramolecular fluorescence resonance energy transfer (FRET) substrate 4-(4-dimethylaminophenylazo)benzoic acid (DABCYL)-Ser-Gln-Asn-Tyr-Pro-Ile-Val-Gln-5-[(2-aminoethyl)amino] naphthalene- 1-sulfonic acid (EDANS) SEQ ID NO:41, wherein Tyr-Pro is the cleavage site (Matayoshi, E. D., et al., *Science* 247:954–958 (1990)); and the chromophoric peptide substrates H-Ser-Gln-Asn-Leu-Phe(NO$_2$)-Leu-Asp-Gly-NH$_2$ SEQ ID NO:42 and acetyl-Arg-Lys-Ile-Leu-Phe (NO$_2$)-Leu-Asp-Gly-NH$_2$ SEQ ID NO:43, wherein the amide bond between the p-nitrophenylalanyl and leucyl residues is the scissile bond. In adddition, the chromogenic substrate, Lys-Ala-Arg-Val-Leu-Phe(NO$_2$)-Glu-Ala-Met SEQ ID NO:44, wherein the Leu-Phe(NO$_2$) is the cleavage site, was reported (Richards, A. D., et al., *J. Biol. Chem.* 265:7733–7736 (1990)). SAR studies found that substitution of the Leu residue in P$_1$ with norleucine, Met, Phe, or Tyr had minimal effects on the kinetic parameters (K$_{cat}$ and K$_{cat}$/K$_m$), as determined at different pH values, whereas peptides containing Ile or Val in P$_1$ were found to hydrolyze extremely slowly. Taking advantage of the presence of non-specific aminopeptidases in whole cells, fluorogenic or fluorescent substrates of HIV protease of Formula V can be designed to incorporate amino acids from both the P side and P' side of HIV substrate for application in whole cell assays. It is expected that after the peptide sequence in the P side is cleaved by the HIV protease, the peptide sequence in the P' side will be removed by aminopeptidases presented in the cells.

For compounds of Formula V designed to be substrates of HIV protease, preferred R$_7$ is acetyl or Cbz, preferred (AA)$_n$ is Thr-Ile-Nle, and preferred (AA)$_m$ is Phe-Gln-Arg, Phe-Gln, or Phe; or preferred (AA)$_n$ is Ser-Leu-Asn-Phe SEQ ID NO:54 or Leu-Asn-Phe, and preferred (AA)$_m$ is Pro-Ile-Val, Pro-Ile, or Pro; or preferred (AA)$_n$ is Ser-Gln-Asn-Tyr SEQ ID NO:45, or Gln-Asn-Tyr, and preferred (AA)$_m$ is Pro-Ile-Val-Gln SEQ ID NO:46, Pro-Ile-Val, Pro-Val-Val-NH$_2$, Pro-Val-NH$_2$, Pro-Ile, or Pro; or preferred (AA)$_n$ is Arg-Gly-Phe, and preferred (AA)$_m$ is Pro; or preferred (AA)$_n$ is Lys-Ala-Arg-Val-Leu SEQ ID NO:47, Ala-Arg-Val-Leu SEQ ID NO:48, or Arg-Val-Leu, and preferred (AA)$_m$ is Phe-Glu-Ala-Met SEQ ID NO:49, Phe-Glu-Ala, Phe-Glu, or Phe; or preferred (AA)$_n$ is Pro-Phe-His-Leu SEQ ID NO:50, or Phe-His-Leu, and preferred (AA)$_n$ is Leu-Glu-Glu-Ser SEQ ID NO:40, Leu-Glu-Glu, Leu-Glu, or Leu; or preferred (AA)$_n$ is Ser-Gln-Asn-Leu-Phe SEQ ID NO:78, Gln-Asn-Leu-Phe SEQ ID NO:51, Asn-Leu-Phe, Arg-Lys-Ile-Leu-Phe SEQ ID NO:52, Lys-Ile-Leu-Phe SEQ ID NO:53, or Ile-Leu-Phe, and preferred (AA)$_m$ is Leu-Asp-Gly-NH$_2$, Leu-Asp-NH$_2$, or Leu-NH$_2$. More preferred (AA)$_n$ is Ser-Leu-Asn-Phe SEQ ID NO:54, or Leu-Asn-Phe, and more preferred (AA)$_m$ is Pro-Ile-Val, Pro-Ile, or Pro; or more preferred (AA)$_n$ is Arg-Gly-Phe, and more preferred (AA)$_m$ is Pro.

Substrates of HIV protease of Formula V are expected to work in whole cell assays but otherwise will not work in cell-free enzyme assays. Cleavage of the (AA)$_n$-(AA)$_m$ amide bond by HIV protease in HIV infected cells will give the Rhodamine attached to (AA)$_m$. Aminopeptidases present inside the cells will then remove the (AA)$_m$ to give the fluorescent dye of Formula VI. Compounds of Formula V will be used for the screening of inhibitors of HIV protease in HIV infected cells. This should speed up the process for the discovery of novel HIV protease inhibitors, especially the discovery of non-peptide or non-peptidomimetic HIV protease inhibitors, which might lead to better anti-HIV agents than currently available drugs. Since HIV protease processes viral precursor proteins at a late stage in viral replication, a cell permeable fluorogenic or fluorescent substrate for an HIV protease also can be used to screen compounds which inhibit gene transcription or translation, viral entry, or other key proteins in the early stage of HIV infection. Therefore this method can lead to the identification of inhibitors of HIV infections with a novel mechanism, which could not be identified in a cell-free enzyme assay. In addition, since HIV protease in HIV infected cells will cleave the cell permeable substrates of Formula V to produce the fluorescent dye of Formula VIII inside the cells, substrates of Formula V also can be used for the diagnosis of HIV infection.

Compounds of Formula V also can be designed to be substrates of adenovirus protease. Adenovirus are the cause of several diseases including sporatic respiratory disease and epidemic acute respiratory disease which can lead to preumonia. Adenovirus protease is a cysteine protease which cleaves several viral proteins and is required for virus maturation and infectivity (Weber, J. M., *Curr. Top. Microbiol. Immunol.* 199/I:227–235 (1995)). The preferred substrates of adenovirus protease includes (M,L,I)XGX-G and (M,L,I)XGG-X. The specificity of the substrates are mainly determined by P$_2$ and P$_4$ amino acids (Diouri, M., et al., *J. Biol. Chem.* 271.32511–32514 (1996)). Hydrophobic amino acids such as Met, Leu and Ile are perferred in P$_4$. Small amino acid such as Gly is preferred in P$_2$. A small and hydrophobic amino acid is also preferred for P$_1$ and P$_1$', such as Ala and Gly; while P$_3$ can accommodate almost any amino acid. These observations were supported by the recently determined crystal structure of human adenorivus proteinase with its 11 aminoacid cofactor and substrate modeling based on the crystal structure (Ding, J., et al., *EMBO J.* 15:1778–1783 (1996)). Taking advantage of the presence of aminopeptidase in whole cells, fluorogenic or fluorescent substrates of adevovirus protease can be designed to incorporate amino acids either from the P side only, or from both the P side and P' side of adenovirus protease substrate for application in whole cell assays.

For compounds of Formula V designed to be substrates of adenovirus protease, preferred R$_7$ is acetyl or Cbz, preferred (AA)$_n$ is Leu-Arg-Gly-Gly SEQ ID NO:55, Met-Arg-Gly-Gly SEQ ID NO:56, Ile-Arg-Gly-Gly SEQ ID NO:57, Leu-Val-Gly-Gly SEQ ID NO:58, Met-Val-Gly-Gly SEQ ID NO:59 or Ile-Val-Gly-Gly SEQ ID NO:60, and preferred (AA)$_m$ is Gly, Ala, or m=0. When m is 0, cleavage of (AA)$_n$-Rhodamine amide bond by the adenovirus protease will produce fluorescent dye of Formula VIII. When m is not 0, cleavage of the (AA)$_n$-(AA)$_m$ amide bond by adenovirus protease in the cells will give the Rhodamine attached to (AA)$_m$. Aminopeptidases present inside the cells will then remove the (AA)$_m$ to give the fluorescent dye of Formula VIII. Compounds of Formula V will be used for the screening of inhibitors of adenovirus protease in adenovirus infected cells.

Compounds of Formula V also can be designed to be substrates of herpes simplex virus type 1 (HSV-1) protease. Human herpes simplex virus type 1 is responsible for herpes labialis (cold sores). The HSV-1 protease is a serine protease and is responsible for proteolytic processing of itself and ICP$_{35}$ for assembly of viral capside (Gao, M., et al., *J. Virol.* 68:3702–3712 (1994)). Two proteolytic sites have been identified to be Ala247 and Ser248 and Ala610 and Ser611 within the protease (DiIanni, C. L., et al., *J. Biol. Chem.* 268:25449–25454 (1993)). Recently, an eight amino acid consensus peptide of LVLASSSF SEQ ID NO:61 was found to be cleaved as efficiently as a 20-mer maturation site peptide, and the P$_4$ to P$_1$ sequence was defined as the minimal substrate recognition domain for the HSV-1 protease (O'Boyle, D. R., et al., *Virology* 236:338–347 (1997)). It also have been reported that the specificity of HSV-1 protease resides within the P$_4$–P$_1$' region of the cleavage sites (McCann, P. J., et al., *J. Virol.* 68:526–529 (1994)). Taking advantage of the presence of aminopeptidase in whole cells, fluorogenic or fluorescent substrates of HSV-1 protease are designed to incorporate amino acids either from the P$_4$–P$_1$ only, or both from P$_4$–P$_1$ and P' side of HSV-1 protease substrate for application in whole cell assays.

For compounds of Formula V designed to be substrates of HSV-1 protease, preferred R$_7$ is acetyl or Cbz, preferred (AA)$_n$ is Leu-Val-Leu-Ala SEQ ID NO:62, and preferred (AA)$_m$ is Ser, Ser-Ser, or m=0. When m is 0, cleavage of (AA)$_n$-Rhodamine amide bond by the HSV-1 protease will produce fluorescent dye of the Formula VIII. When m is not 0, cleavage of the (AA)$_n$-(AA)$_m$ amide bond by HSV-1 in the cells will give the Rhodamine attached to (AA)$_m$. Aminopeptidases present inside the cells will then remove the (AA)$_m$ to give the fluorescent dye of Formula VIII. Compounds of Formula V will be used for the screening of inhibitors of HSV-1 protease in HSV-1 infected cells.

Compounds of Formula V also can be designed to be substrates of human cytomegalovirus (HCMV) protease. HCMV can cause life-threatening infections in congenitally infected infants, immunocompromised individuals and immunosuppressed cancer or transplant patients. Human cytomegalovirus (HCMV) encodes a protease that cleaves itself and the HCMV assembly protein and is essential for virus replication, therefore it is a potential target for therapeutic intervention. The HCMV protease is a serine protease and two proteolytic processing sites within the protease were identified at Ala 256-Ser 257 (release site) and Ala 643-Ser 644 (maturation site). (Sztevens, J. T., et al., *Eur. J. Biochem.* 226:361–367 (1994)). A fluorogenic substrate, DABCYL-Arg-Gly-Val-Val-Asn-Ala-Ser-Ser-Arg-Leu-Ala-EDANS SEQ ID NO:63 was synthesized and found to be cleaved efficiently by CMV protease at the Ala-Ser peptide bond (Holskin, B. P., et al., *Anal. Biochem.* 227.148–155 (1995)). Recently, it was reported that replacement of the Val-Val-Asn sequence corresponding to the P$_4$–P$_2$ residues of the maturation site of the enzyme by the optimized Tbg-Tbg-Asn(NMe$_2$) (Tbg, t-butylglycine) sequence increase significantly the affinity of the substrate to the protease. An AMC fluorogenic substrate was prepared with the P side peptide sequence including these improved amino acids (Bonneau, P. R., et al., *Anal. Biochem.* 255.59–65 (1998)). Taking advantage of the presence of aminopeptidase in whole cells, fluorogenic or fluorescent substrates of HCMV protease are designed to incorporate amino acids either from the P side only, or both from P side and P' side of HCMV protease substrate for application in whole cell assays.

For compounds of Formula V designed to be substrates of HCMV protease, preferred R$_7$ is acetyl or Cbz, preferred (AA)$_n$ is Val-Val-Asn-Ala SEQ ID NO:64 or Tbg-Tbg-Asn-Ala SEQ ID NO:65, and preferred (AA)$_m$ is Ser, Ser-Ser, or m=0. When m is 0, cleavage of (AA)$_n$-Rhodamine amide bond by the HCMV protease will produce fluorescent dye of the Formula VIII. When m is not 0, cleavage of the (AA)$_n$-(AA)$_m$ amide bond by HCMV in the cells will give the Rhodamine attached to (AA)$_m$. Aminopeptidases present inside the cells will then remove the (AA)$_m$ to give the fluorescent dye of Formula VIII. Compounds of Formula V will be used for the screening of inhibitors of HCMV protease in HCMV infected cells.

Compounds of Formula V also can be designed to be substrates of hepatitis C virus (HCV) protease. HCV is the major causative agent of both parenterally transmitted and sporadic non-A and non-B hepatitis, which infects an estimated 50 million people worldwide. HCV protease NS3 and its protein activator NS4A participate in the processing of the viral polyprotein, thus the NS3/4A protease complex is an attractive target for antiviral therapy against HCV. The HCV protease is a serine protease and Cys-Ser has been identified as a cleavage site. One of the substrate sequence is Asp-Asp-Ile-Val-Pro-Cys-Ser-Met-Ser-Tyr SEQ ID NO:66, and P$_1$ Cys and P$_3$ Val were found to be critical (Zhang, R., et al., *J. Virol.* 71:6208–6213 (1997)). Taking advantage of the presence of aminopeptidase in whole cells, fluorogenic or fluorescent substrates of HCV protease are designed to incorporate amino acids both from the P side and P' side of HCV protease substrate for application in whole cell assays.

For compounds of Formula V designed to be substrates of HCV protease, preferred R$_7$ is acetyl or Cbz, preferred (AA)$_n$ is Asp-Asp-Ile-Val-Pro-Cys SEQ ID NO:67, Asp-Ile-Val-Pro-Cys SEQ ID NO:68, or Ile-Val-Pro-Cys SEQ ID NO:69 and preferred (AA)$_m$ is Ser-Met-Ser-Tyr SEQ ID NO:70, Ser-Met-Ser, Ser-Met, Ser, or m=0. When m is 0, cleavage of (AA)$_n$-Rhodamine amide bond by the HCV protease will produce fluorescent dye of the Formula VIII. When m is not 0, cleavage of the (AA)$_n$-(AA)$_m$ amide bond by HCV in the cells will give the Rhodamine attached to (AA)$_m$. Aminopeptidases present inside the cells will then remove the (AA)$_m$ to give the fluorescent dye of Formula VIII. Compounds of Formula V will be used for the screening of inhibitors of HCV protease in HCV infected cells.

The invention also relates to the novel compound of Formula VIII which are derivatives of a Rhodamine obtained by introducing a fluoro- or chloro-substituted benzoyl blocking group into one of the two amino groups in a Rhodamine. The HNR$_8$ group in Formula VIII provides the point of attachment for the reaction with a potential enzyme substrate, such as the carboxylic group of a N-blocked peptide, to form a peptide amide bond. The reaction will convert the fluorescent molecule of Formula VIII into a non-fluorescent molecule of Formula IV or V and produce a peptide-reporter molecule which functions as a substrate for a protease or peptidase. Cleavage of the scissile peptide-reporter amide bond in the peptide-reporter by proteases or peptidases produces a compound of Formula VIII or VIII' which is fluorescent. More importantly, the hydrophobic fluoro- or chloro-substituted benzoyl blocking group is designed to increase cell permeability of the substrates of Formula I. The fluoro- or chloro-substituted benzoyl group is also designed to react with nucleophiles presented inside the cells, thus resulting in an accumulation of the substrates of Formula I inside the cells, as well as an increase in retention of the fluorescent moiety inside the cells after cleavage by target enzymes. In addition, replacement of the fluoro or chloro group by a nucleophile is expected to increase fluorescent intensity of the fluorescence moiety of the substrate of Formula I.

Specifically, the novel fluorescent dyes of this invention are of Formula VIII:

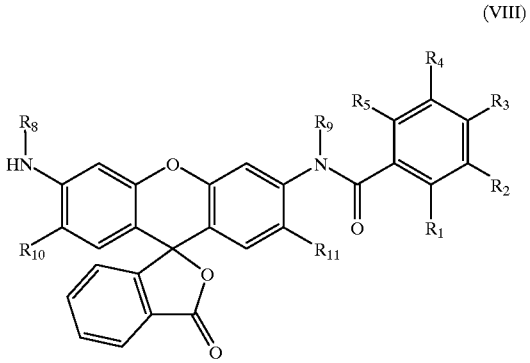
(VIII)

or biologically acceptable salts wherein $R_1$–$R_5$, $R_8$–$R_{11}$ are defined above with respect to Formula II and III.

Compounds of Formula VIII of the present invention may exist in tautomeric forms, particularly the ring opening form of Formula VIII'. The invention includes all tautomeric forms including VIII and VIII'.

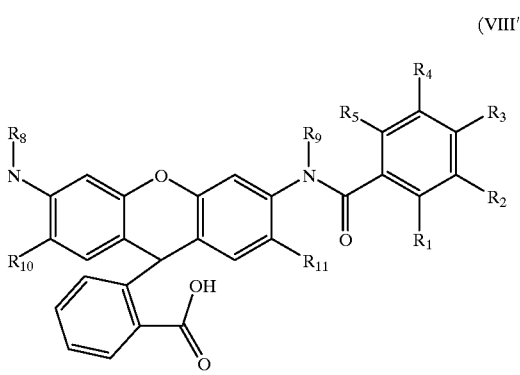
(VIII')

Preferred fluorogenic or fluorescent substrates of the present invention are compounds having Formula I and include, but are not limited to:

N-(Z-WEHD)-N'-pentafluorobenzoyl-Rhodamine 110, (SEQ ID NO:1)
N-(Z-YVAD)-N'-pentafluorobenzoyl-Rhodamine 110, (SEQ ID NO:2)
N-(Z-LEHD)-N'-pentafluorobenzoyl-Rhodamine 110, (SEQ ID NO:3)
N-(Z-DETD)-N'-pentafluorobenzoyl-Rhodamine 110, (SEQ ID NO:4)
N-(Z-DEVD)-N'-pentafluorobenzoyl-Rhodamine 110, (SEQ ID NO:5)
N-(Z-VEHD)-N'-pentafluorobenzoyl-Rhodamine 110, (SEQ ID NO:7)
N-(Z-LETD)-N'-pentafluorobenzoyl-Rhodamine 110, (SEQ ID NO:8)
N-(Z-LEHD)-N'-pentafluorobenzoyl-Rhodamine 110, (SEQ ID NO:3)
N-(Z-IEPD)-N'-pentafluorobenzoyl-Rhodamine 110, (SEQ ID NO:23)
N-(Z-VEPD)-N'-pentafluorobenzoyl-Rhodamine 110, (SEQ ID NO:27)
N-(Z-SHVD)-N'-pentafluorobenzoyl-Rhodamine 110, (SEQ ID NO:10)
N-(Z-DELD)-N'-pentafluorobenzoyl-Rhodamine 110, (SEQ ID NO:11)
N-(Z-DGPD)-N'-pentafluorobenzoyl-Rhodamine 110, (SEQ ID NO:12)
N-(Z-DEPD)-N'-pentafluorobenzoyl-Rhodamine 110, (SEQ ID NO:13)
N-(Z-DGTD)-N'-pentafluorobenzoyl-Rhodamine 110, (SEQ ID NO:14)
N-(Z-DLND)-N'-pentafluorobenzoyl-Rhodamine 110, (SEQ ID NO:15)
N-(Z-DEED)-N'-pentafluorobenzoyl-Rhodamine 110, (SEQ ID NO:16)
N-(Z-DSLD)-N'-pentafluorobenzoyl-Rhodamine 110, (SEQ ID NO:17)
N-(Z-DVPD)-N'-pentafluorobenzoyl-Rhodamine 110, (SEQ ID NO:18)
N-(Z-DEAD)-N'-pentafluorobenzoyl-Rhodamine 110, (SEQ ID NO:19)
N-(Z-DSYD)-N'-pentafluorobenzoyl-Rhodamine 110, (SEQ ID NO:20)
N-(Z-ELPD)-N'-pentafluorobenzoyl-Rhodamine 110, (SEQ ID NO:21)
N-(Z-VEID)-N'-pentafluorobenzoyl-Rhodamine 110, (SEQ ID NO:26)
N-(Z-IETD)-N'-pentafluorobenzoyl-Rhodamine 110, (SEQ ID NO:24)
N-(Z-VD)-N'-pentafluorobenzoyl-Rhodamine 110,
N-(Z-TD)-N'-pentafluorobenzoyl-Rhodamine 110,
N-(Z-AD)-N'-pentafluorobenzoyl-Rhodamine 110,
N-(Z-VAD)-N'-pentafluorobenzoyl-Rhodamine 110,
N-(Z-DEVDG)-N'-pentafluorobenzoyl-Rhodamine 110, (SEQ ID NO:76)
N-(Z-EVDG)-N'-pentafluorobenzoyl-Rhodamine 110, (SEQ ID NO:71)
N-(PFB-DEVDG)-N'-pentafluorobenzoyl-Rhodamine 110, (SEQ ID NO:76)
N-(PFB-EVDG)-N'-pentafluorobenzoyl-Rhodamine 110, (SEQ ID NO:71)
N-(PFB-DEVD)-N'-pentafluorobenzoyl-Rhodamine 110, (SEQ ID NO:5)
N-(Octanoyl-DEVD)-N'-pentafluorobenzoyl-Rhodamine 110, (SEQ ID NO:5)
N-(PFB-EVD)-N'-pentafluorobenzoyl-Rhodamine 110,
N-(Boc-WEHD)-N'-pentafluorobenzoyl-Rhodamine 110, (SEQ ID NO:1)
N-(Boc-YVAD)-N'-pentafluorobenzoyl-Rhodamine 110, (SEQ ID NO:2)
N-(Ac-LETD)-N'-pentafluorobenzoyl-Rhodamine 110, (SEQ ID NO:8)
N-(Ac-DEVD)-N'-pentafluorobenzoyl-Rhodamine 110, (SEQ ID NO:5)
N-(Ac-IETD)-N'-pentafluorobenzoyl-Rhodamine 110, (SEQ ID NO:24)
N-(Ac-LQTD)-N'-pentafluorobenzoyl-Rhodamine 110, (SEQ ID NO:72)
N-(Ac-EETD)-N'-pentafluorobenzoyl-Rhodamine 110, (SEQ ID NO:73)
N-(Ac-LEVD)-N'-pentafluorobenzoyl-Rhodamine 110, (SEQ ID NO:9)
N-(Ac-AEHD)-N'-pentafluorobenzoyl-Rhodamine 110, (SEQ ID NO:74)
N-(Ac-WEHD)-N'-pentafluorobenzoyl-Rhodamine 110, (SEQ ID NO:1)
N-(Ac-YVAD)-N'-pentafluorobenzoyl-Rhodamine 110, (SEQ ID NO:2)
N-(Ac-D(OEt)E(OEt)VD(OEt))-N'-pentafluorobenzoyl-Rhodamine 110, (SEQ ID NO:5)
N-(Ac-LEHD)-N'-pentafluorobenzoyl-Rhodamine 110, (SEQ ID NO:3)
N-(Z-DEVD)-N'-(2,3,4,5-tetrafluorobenzoyl)-Rhodamine 110, (SEQ ID NO:5)

N-(Ac-DEVD)-N'-(2,3,4,5-tetrafluorobenzoyl)-Rhodamine 110, (SEQ ID NO:5)
N-(Ac-IETD)-N'-(2,3,4,5-tetrafluorobenzoyl)-Rhodamine 110, (SEQ ID NO:24)
N-(Ac-LQTD)-N'-(2,3,4,5-tetrafluorobenzoyl)-Rhodamine 110, (SEQ ID NO:72)
N-(Ac-EETD)-N'-(2,3,4,5-tetrafluorobenzoyl)-Rhodamine 110, (SEQ ID NO:73)
N-(Ac-LEVD)-N'-(2,3,4,5-tetrafluorobenzoyl)-Rhodamine 110, (SEQ ID NO:9)
N-(Ac-AEHD)-N'-(2,3,4,5-tetrafluorobenzoyl)-Rhodamine 110, (SEQ ID NO:74)
N-(Ac-WEHD)-N'-(2,3,4,5-tetrafluorobenzoyl)-Rhodamine 110, (SEQ ID NO:1)
N-(Ac-YVAD)-N'-(2,3,4,5-tetrafluorobenzoyl)-Rhodamine 110, (SEQ ID NO:2)
N-(Z-YVAD)-N'-(2,3,4,5-tetrafluorobenzoyl)-Rhodamine 110, (SEQ ID NO:2)
N-(Z-DEVD)-N'-(2,3,4,5-tetrafluorobenzoyl)-Rhodamine 110, (SEQ ID NO:5)
N-(Z-YVAD)-N'-(2,3,4,5-tetrafluorobenzoyl)-Rhodamine 110, (SEQ ID NO:2)
N-(Z-DEVD)-N'-pentafluorobenzoyl-Rhodamine 116, (SEQ ID NO:5)
N-(Z-YVAD)-N'-(2,3,4,5-tetrafluorobenzoyl)-Rhodamine 116, (SEQ ID NO:2)
N-(Z-DEVD)-N'-pentafluorobenzoyl-Rhodamine 19, (SEQ ID NO:5)
N-(Z-YVAD)-N'-(2,3,4,5-tetrafluorobenzoyl)-Rhodamine 19, (SEQ ID NO:2)
N-(Z-YVAD(OAM))-N'-pentafluorobenzoyl-Rhodamine 110, (SEQ ID NO:2)
N-(Z-LE(OAM)HD(OAM))-N'-pentafluorobenzoyl-Rhodamine 110, (SEQ ID NO:3)
N-(Z-D(OAM)E(OAM)TD(OAM))-N'-pentafluorobenzoyl-Rhodamine 110, (SEQ ID NO:4)
N-(Z-D(OAM)E(OAM)VD(OAM))-N'-pentafluorobenzoyl-Rhodamine 110, (SEQ ID NO:5)
N-(Z-D(OMe)E(OMe)VD(OAM))-N'-pentafluorobenzoyl-Rhodamine 110, (SEQ ID NO:5)
N-(Z-D(OMe)E(OMe)VD)-N'-pentafluorobenzoyl-Rhodamine 110, (SEQ ID NO:5)
N-(Z-VD(OAM))-N'-pentafluorobenzoyl-Rhodamine 110,
N-(Z-E(OAM)VD(OAM))-N'-pentafluorobenzoyl-Rhodamine 110,
N-(MG)-N'-pentafluorobenzoyl-Rhodamine 110,
N-(MA)-N'-pentafluorobenzoyl-Rhodamine 110,
N-(MGG)-N'-pentafluorobenzoyl-Rhodamine 110,
N-(MGA)-N'-pentafluorobenzoyl-Rhodamine 110,
N-(MAG)-N'-pentafluorobenzoyl-Rhodamine 110,
N-G-N'-pentafluorobenzoyl-Rhodamine 110,
N-(MG)-N'-(2,3,4,5-tetrafluorobenzoyl)-Rhodamine 110,
N-(MA)-N'-(2,3,4,5-tetrafluorobenzoyl)-Rhodamine 110,
N-G-N'-(2,3,4,5-tetrafluorobenzoyl)-Rhodamine 110,
N-(MG)-N'-(3,4,5-trifluorobenzoyl)-Rhodamine 110,
N-(MA)-N'-(3,4,5-trifluorobenzoyl)-Rhodamine 110,
N-G-N'-(3,4,5-trifluorobenzoyl)-Rhodamine 110,
N-(MG)-N'-(2,4,6-trifluorobenzoyl)-Rhodamine 110,
N-G-N'-(2,4,6-trifluorobenzoyl)-Rhodamine 110,
N-(Ac-SLNFPIV)-N'-pentafluorobenzoyl-Rhodamine 110, (SEQ ID NO:80)
N-(Ac-SLNFPI)-N'-pentafluorobenzoyl-Rhodamine 110, (SEQ ID NO:81)
N-(Ac-SLNFP)-N'-pentafluorobenzoyl-Rhodamine 110, (SEQ ID NO:82)
N-(Ac-LNFPIV)-N'-pentafluorobenzoyl-Rhodamine 110, (SEQ ID NO:83)
N-(Ac-LNFPI)-N'-pentafluorobenzoyl-Rhodamine 110, (SEQ ID NO:84)
N-(Ac-LNFP)-N'-pentafluorobenzoyl-Rhodamine 110, (SEQ ID NO:85)
N-(Ac-RGFP)-N'-pentafluorobenzoyl-Rhodamine 110, (SEQ ID NO:37)
N-(Z-LNFPIV)-N'-pentafluorobenzoyl-Rhodamine 110, (SEQ ID NO:83)
N-(Z-LNFPI)-N'-pentafluorobenzoyl-Rhodamine 110, (SEQ ID NO:84)
N-(Z-LNFP)-N'-pentafluorobenzoyl-Rhodamine 110, (SEQ ID NO:85)
N-(Z-RGFP)-N'-pentafluorobenzoyl-Rhodamine 110, (SEQ ID NO:37)
N-(Z-RQANFLG)-N'-pentafluorobenzoyl-Rhodamine 110, (SEQ ID NO:31)
N-(Z-RQANFL)-N'-pentafluorobenzoyl-Rhodamine 110, (SEQ ID NO:86)
N-(Z-RQANF)-N'-pentafluorobenzoyl-Rhodamine 110, (SEQ ID NO:87)
N-(Z-RKVLFLD)-N'-pentafluorobenzoyl-Rhodamine 110, (SEQ ID NO:36)
N-(Z-RKVLFL)-N'-pentafluorobenzoyl-Rhodamine 110, (SEQ ID NO:88)
N-(Z-RKVLF)-N'-pentafluorobenzoyl-Rhodamine 110, (SEQ ID NO:89)
N-(Z-ARVLFLG)-N'-pentafluorobenzoyl-Rhodamine 110, (SEQ ID NO:90)
N-(Z-ARVLFL)-N'-pentafluorobenzoyl-Rhodamine 110, (SEQ ID NO:91)
N-(Z-ARVLF)-N'-pentafluorobenzoyl-Rhodamine 110, (SEQ ID NO:92)
N-(Z-SQNYFLG)-N'-pentafluorobenzoyl-Rhodamine 110, (SEQ ID NO:93)
N-(Z-SQNYFL)-N'-pentafluorobenzoyl-Rhodamine 110, (SEQ ID NO:94)
N-(Z-SQNYF)-N'-pentafluorobenzoyl-Rhodamine 110, (SEQ ID NO:95)
N-(Ac-SLNFPIV)-N'-(2,3,4,5-tetrafluorobenzoyl)-Rhodamine 110, (SEQ ID NO:80)
N-(Ac-SLNFPI)-N'-(2,3,4,5-tetrafluorobenzoyl)-Rhodamine 110, (SEQ ID NO:81)
N-(Ac-SLNFP)-N'-(2,3,4,5-tetrafluorobenzoyl)-Rhodamine 110, (SEQ ID NO:82)
N-(Ac-RGFP)-N'-(2,3,4,5-tetrafluorobenzoyl)-Rhodamine 110, (SEQ ID NO:37)
N-(Ac-SLNFPIV)-N'-(2,4,6-trifluorobenzoyl)-Rhodamine 110, (SEQ ID NO:80)
N-(Ac-SLNFPI)-N'-(2,4,6-trifluorobenzoyl)-Rhodamine 110, (SEQ ID NO:81)
N-(Ac-SLNFP)-N'-(2,4,6-trifluorobenzoyl)-Rhodamine 110, (SEQ ID NO:82)
N-(Ac-RGFP)-N'-(2,4,6-trifluorobenzoyl)-Rhodamine 110, (SEQ ID NO:37)
N-(Ac-MRGGG)-N'-pentafluorobenzoyl-Rhodamine 110, (SEQ ID NO:96)
N-(Ac-IRGGG)-N'-pentafluorobenzoyl-Rhodamine 110, (SEQ ID NO:97)
N-(Ac-LVGGG)-N'-pentafluorobenzoyl-Rhodamine 110, (SEQ ID NO:98)
N-(Ac-MVGGG)-N'-pentafluorobenzoyl-Rhodamine 110, (SEQ ID NO:99)
N-(Ac-IVGGG)-N'-pentafluorobenzoyl-Rhodamine 110, (SEQ ID NO:100)
N-(Ac-LRGGG)-N'-pentafluorobenzoyl-Rhodamine 110, (SEQ ID NO:101)
N-(Ac-LRGGA)-N'-pentafluorobenzoyl-Rhodamine 110, (SEQ ID NO:102)

N-(Ac-LRGG)-N'-pentafluorobenzoyl-Rhodamine 110, (SEQ ID NO:55)
N-(Z-LRGGG)-N'-pentafluorobenzoyl-Rhodamine 10, (SEQ ID NO:101)
N-(Z-LRGGA)-N'-pentafluorobenzoyl-Rhodamine 110, (SEQ ID NO:102)
N-(Z-LRGG)-N'-pentafluorobenzoyl-Rhodamine 110, (SEQ ID NO:55)
N-(Ac-LRGGG)-N'-(2,3,4,5-tetrafluorobenzoyl)-Rhodamine 110, (SEQ ID NO:101)
N-(Ac-LRGGA)-N'-(2,3,4,5-tetrafluorob enzoyl)-Rhodamine 110, (SEQ ID NO:102)
N-(Ac-LRGG)-N'-(2,3,4,5-tetrafluorobenzoyl)-Rhodamine 110, (SEQ ID NO:55)
N-(Ac-LRGGG)-N'-(2,4,6-trifluorobenzoyl)-Rhodamine 110, (SEQ ID NO:101)
N-(Ac-LRGGA)-N'-(2,4,6-trifluorobenzoyl)-Rhodamine 110, (SEQ ID NO:102)
N-(Ac-LRGG)-N'-(2,4,6-trifluorobenzoyl)-Rhodamine 110, (SEQ ID NO:55)
N-(Ac-LVLASSS)-N'-pentafluorobenzoyl-Rhodamine 110, (SEQ ID NO:103)
N-(Ac-LVLASS)-N'-pentafluorobenzoyl-Rhodamine 110, (SEQ ID NO:104)
N-(Ac-LVLAS)-N'-pentafluorobenzoyl-Rhodamine 110, (SEQ ID NO:105)
N-(Ac-LVLA)-N'-pentafluorobenzoyl-Rhodamine 110, (SEQ ID NO:62)
N-(Z-LVLASSS)-N'-pentafluorobenzoyl-Rhodamine 110, (SEQ ID NO:103)
N-(Z-LVLASS)-N'-pentafluorobenzoyl-Rhodamine 110, (SEQ ID NO:104)
N-(Z-LVLAS)-N'-pentafluorobenzoyl-Rhodamine 110, (SEQ ID NO:105)
N-(Z-LVLA)-N'-pentafluorobenzoyl-Rhodamine 110, (SEQ ID NO:62)
N-(Ac-LVLASS)-N'-(2,3,4,5-tetrafluorobenzoyl)-Rhodamine 110, (SEQ ID NO:104)
N-(Ac-LVLAS)-N'-(2,3,4,5-tetrafluorobenzoyl)-Rhodamine 110, (SEQ ID NO:105)
N-(Ac-LVLA)-N'-(2,3,4,5-tetrafluorobenzoyl)-Rhodamine 110, (SEQ ID NO:62)
N-(Ac-LVLASS)-N'-(2,4,6-trifluorobenzoyl)-Rhodamine 110, (SEQ ID NO:104)
N-(Ac-LVLAS)-N'-(2,4,6-trifluorobenzoyl)-Rhodamine 110, (SEQ ID NO:105)
N-(Ac-LVLA)-N'-(2,4,6-trifluorobenzoyl)-Rhodamine 110, (SEQ ID NO:62)
N-(Ac-VVNASS)-N'-pentafluorobenzoyl-Rhodamine 110, (SEQ ID NO:106)
N-(Ac-VVNAS)-N'-pentafluorobenzoyl-Rhodamine 110, (SEQ ID NO:107)
N-(Ac-VVNA)-N'-pentafluorobenzoyl-Rhodamine 110, (SEQ ID NO:64)
N-(Ac-Tbg-Tbg-NASS)-N'-pentafluorobenzoyl-Rhodamine 110, (SEQ ID NO:108)
N-(Ac-Tbg-Tbg-NAS)-N'-pentafluorobenzoyl-Rhodamine 110, (SEQ ID NO:109)
N-(Ac-Tbg-Tbg-NA)-N'-pentafluorobenzoyl-Rhodamine 110, (SEQ ID NO:110)
N-(Z-Tbg-Tbg-NASS)-N'-pentafluorobenzoyl-Rhodarnine 110, (SEQ ID NO:108)
N-(Z-Tbg-Tbg-NAS)-N'-pentafluorobenzoyl-Rhodamine 110, (SEQ ID NO:109)
N-(Z-Tbg-Tbg-NA)-N'-pentafluorobenzoyl-Rhodamine 110, (SEQ ID NO:110)
N-(Ac-Tbg-Tbg-NASS)-N'-(2,3,4,5-tetrafluorobenzoyl)-Rhodamine 110, (SEQ ID NO:108)
N-(Ac-Tbg-Tbg-NAS)-N'-(2,3,4,5-tetrafluorobenzoyl)-Rhodamine 110, (SEQ ID NO:109)
N-(Ac-Tbg-Tbg-NA)-N'-(2,3,4,5-tetrafluorobenzoyl)-Rhodamine 110, (SEQ ID NO:110)
N-(Ac-Tbg-Tbg-NASS)-N'-(2,4,6-trifluorobenzoyl)-Rhodamine 110, (SEQ ID NO:108)
N-(Ac-Tbg-Tbg-NAS)-N'-(2,4,6-trifluorobenzoyl)-Rhodamine 110, (SEQ ID NO:109)
N-(Ac-Tbg-Tbg-NA)-N'-(2,4,6-trifluorobenzoyl)-Rhodamine 110, (SEQ ID NO:110)
N-(Ac-DDIVPCSMST)-N'-pentafluorobenzoyl-Rhodamine 110, (SEQ ID NO:111)
N-(Ac-DIVPCSMST)-N'-pentafluorobenzoyl-Rhodamine 110, (SEQ ID NO:112)
N-(Ac-IVPCSMST)-N'-pentafluorobenzoyl-Rhodamine 110, (SEQ ID NO:113)
N-(Ac-IVPCSMS)-N'-pentafluorobenzoyl-Rhodamine 110, (SEQ ID NO:114)
N-(Ac-IVPCSM)-N'-pentafluorobenzoyl-Rhodamine 110, (SEQ ID NO:115)
N-(Ac-IVPCS)-N'-pentafluorobenzoyl-Rhodamine 110, (SEQ ID NO:116)
N-(Ac-IVPC)-N'-pentafluorobenzoyl-Rhodamine 110, (SEQ ID NO:69)
N-(Z-IVPCSMST)-N'-pentafluorobenzoyl-Rhodamine 110, (SEQ ID NO:113)
N-(Z-IVPCSMS)-N'-pentafluorobenzoyl-Rhodamine 110, (SEQ ID NO:114)
N-(Z-IVPCSM)-N'-pentafluorobenzoyl-Rhodamine 110, (SEQ ID NO:115)
N-(Z-IVPCS)-N'-pentafluorobenzoyl-Rhodamine 110, (SEQ ID NO:116)
N-(Ac-IVPCSMS)-N'-(2,3,4,5-tetrafluorobenzoyl)-Rhodamine 110, (SEQ ID NO:114)
N-(Ac-IVPCSM)-N'-(2,3,4,5-tetrafluorobenzoyl)-Rhodamine 110, (SEQ ID NO:115)
N-(Ac-IVPCS)-N'-(2,3,4,5-tetrafluorobenzoyl)-Rhodamine 110, (SEQ ID NO:116)
N-(Ac-IVPCSMS)-N'-(2,4,6-trifluorobenzoyl)-Rhodamine 110, (SEQ ID NO:114)
N-(Ac-IVPCSM)-N'-(2,4,6-trifluorobenzoyl)-Rhodamine 110, (SEQ ID NO:115)
N-(Ac-IVPCS)-N'-(2,4,6-trifluorobenzoyl)-Rhodamine 110, (SEQ ID NO:116)

where Z is benzyloxycarbonyl, BOC is tert-butoxycarbonyl, Ac is acetyl, PFB is pentafluorobenzoyl, Tbg is t-butylglycine, and AM is acetoxymethyl.

Preferred novel fluorescent dyes of the present invention are compounds having Formula VIII and include, but are not limited to:

N-pentafluorobenzoyl-Rhodamine 110,
N-(2,3,4,5-tetrafluorobenzoyl)-Rhodamine 110,
N-(2,4,6-trifluorobenzoyl)-Rhodamine 110,
N-(4-fluoro-3-trifluoromethylbenzoyl)-Rhodamine 110,
N-(2,3,5,6-tetrafluorobenzoyl)-Rhodamine 110,
N-(2,3,4-trifluorobenzoyl)-Rhodamine 110,
N-(2,4,5-trifluorobenzoyl)-Rhodamine 110,
N-(3,4,5-trifluorobenzoyl)-Rhodamine 110,
N-pentafluorobenzoyl-Rhodamine 116,
N-pentafluorobenzoyl-Rhodamine 19,
N-(2,3,4,5-tetrafluorobenzoyl)-Rhodamine 116,
N-(2,3,4,5-tetrafluorobenzoyl)-Rhodamine 19,
N-(4-fluoro-3-trifluoromethylbenzoyl)-Rhodamine 116, and
N-(4-fluoro-3-trifluoromethylbenzoyl)-Rhodamine 19.

Useful aryl groups are $C_{6-14}$ aryl, especially $C_{6-10}$ aryl. Typical $C_{6-14}$ aryl groups include phenyl, naphthyl, phenanthryl, anthracyl, indenyl, azulenyl, biphenyl, biphenylenyl and fluorenyl groups.

Useful cycloalkyl groups are $C_{3-8}$ cycloalkyl groups, preferably cyclopropyl, cyclobutyl, cyclopentyl, cyclohexyl and cycloheptyl.

Useful alkyl groups include straight-chained and branched $C_{1-12}$ alkyl groups, preferably $C_{1-10}$ alkyl groups, more preferably, $C_{1-6}$ alkyl groups. Typical $C_{1-12}$ alkyl groups include methyl, ethyl, propyl, isopropyl, butyl, sec-butyl, tert-butyl, 3-pentyl, hexyl and octyl groups.

Useful acyl (alkanoyl) groups are $C_{2-10}$ alkanoyl groups such as acetyl, propionyl, butanoyl, pentanoyl, hexanoyl and the like as well as the branched chain isomers.

Useful alkenyl groups are $C_{2-6}$ alkenyl groups, including ethenyl, propenyl, isopropenyl, butenyl, and sec-butenyl.

Useful alkynyl groups are $C_{2-6}$ alkynyl groups, including ethynyl, propynyl, butynyl, and 2-butynyl groups.

Useful aralkyl groups include any of the above-mentioned $C_{1-10}$ alkyl groups substituted by any of the above-mentioned $C_{6-14}$ aryl groups. Particularly useful groups include benzyl, phenethyl and naphthylmethyl.

Useful aralkenyl groups include any of the above-mentioned $C_{2-4}$ alkenyl groups substituted by any of the above-mentioned $C_{6-14}$ aryl groups.

Useful aralkynyl groups include any of the above-mentioned $C_{2-4}$ alkynyl groups substituted by any of the above-mentioned $C_{6-14}$ aryl groups. Particularly useful groups include phenylethynyl and phenylpropynyl.

Useful haloalkyl groups include any of the above mentioned $C_{1-10}$ alkyl groups substituted by one or more fluorine, chlorine, bromine or iodine atoms, e.g. fluoromethyl, difluoromethyl, trifluoromethyl, pentafluoroethyl, 1,1-difluoroethyl, chloromethyl, chlorofluoromethyl and trichloromethyl groups.

Useful hydroxyalkyl groups include any of the above mentioned $C_{1-10}$ alkyl groups substituted by hydroxy, e.g. hydroxymethyl, hydroxyethyl, hydroxypropyl and hydroxybutyl groups.

Useful alkoxy groups include oxygen substituted by one of the $C_{1-10}$ alkyl groups mentioned above.

Useful alkylthio groups include sulphur substituted by one of the $C_{1-10}$ alkyl groups mentioned above.

Useful acylamino groups are any of the above mentioned $C_{1-6}$ acyl (alkanoyl) groups attached to an amino nitrogen, e.g. acetamido, propionamido, butanoylamido, pentanoylamido, hexanoylamido as well as aryl-substituted $C_{2-6}$ acyl groups.

Useful acyloxy groups are any of the above mentioned $C_{1-6}$ acyl (alkanoyl) groups attached to an oxy (—O—) group, e.g. acetoxy, propionoyloxy, butanoyloxy, pentanoyloxy, hexanoyloxy and the like.

Useful amino groups include —$NH_2$, —$NHR_{14}$ and —$NR_{14}R_{15}$, wherein $R_{14}$ and $R_{15}$ are $C_{1-10}$ alkyl or $C_{3-8}$ cycloalkyl groups as defined above.

Certain of the compounds of the present invention may be in tautomeric forms, particularly in the Y-portion of Formula I. The invention includes all such tautomers. The invention also includes stereoisomers, the racemic mixtures of such stereoisomers as well as the individual entantiomers that may be separated according to methods that are well known to those of ordinary skill in the art.

The compounds of this invention may be prepared using methods known to those skilled in the art. Specifically, compounds of Formula VIII can be prepared as illustrated by the exemplary reactions in Scheme 1.

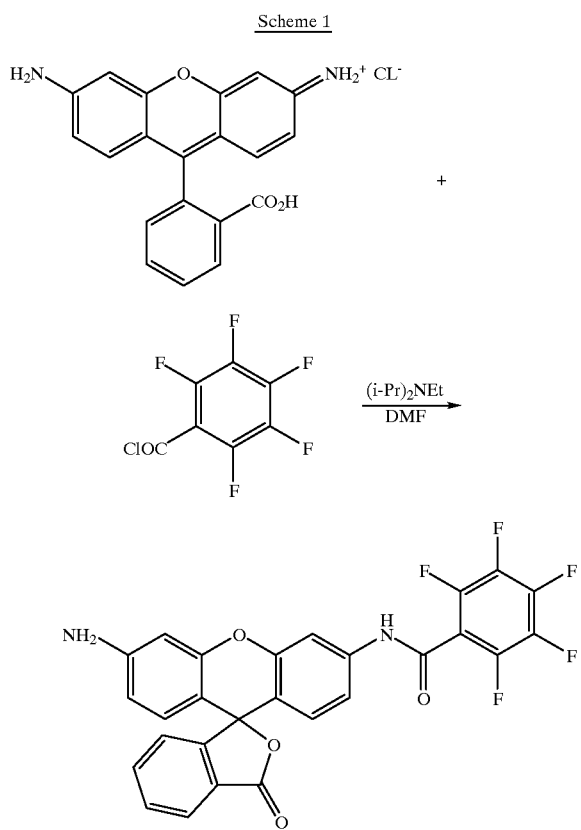

Scheme 1

Compounds with Formulae I–V can be prepared as illustrated by the exemplary reactions in Schemes 2–3.

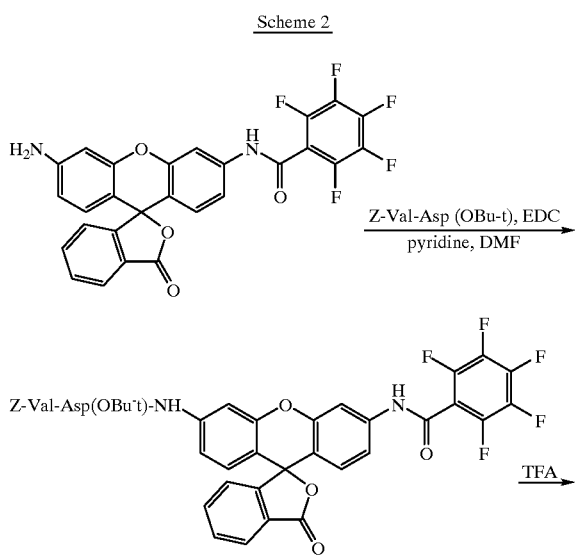

Scheme 2

(b) reacting Rhodamine with a compound of Formula (VI)

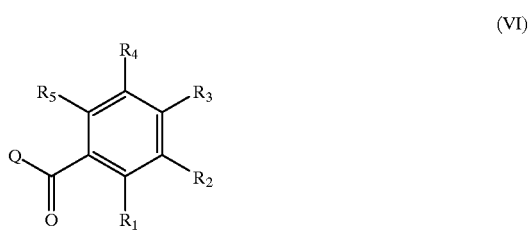

wherein $R_1$–$R_5$ are defined above and Q is halo, hydroxy or a group of Formula VII:

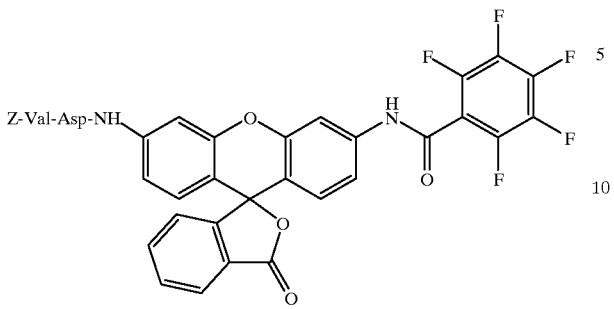

where $R_1$–$R_5$ defined above,
to give the substituted benzoyl-Rhodamine of Formula VIII;
  (b) condensing the substituted N-benzoyl-Rhodamine together with N-Z-Gly to give N-Z-Gly-N'-substituted benzoyl-Rhodamine;
  (c) removing the Z group to give N-Gly-N'-substituted benzoyl-Rhodamine;
  (d) condensing N-Gly-N'-substituted benzoyl-Rhodamine with Z-(AA)$_n$-Asp(OBu-t) to give N-(Z-(AA)$_n$-Asp(OBu-t)-Gly)-N'-substituted benzoyl-Rhodamine; and
  (e) removing the OBu-t protecting group to give N-(Z-(AA)$_n$-Asp-Gly)-N'-substituted benzoyl-Rhodamine.

Alternatively, the step introducing Gly may be omitted and a compound of general Formula IV can be obtained by a method comprising the steps of:
  (a) reacting Rhodamine with a compound of Formula VI to give a substituted N-benzoyl-Rhodamine;
  (b) condensing the substituted N-benzoyl-Rhodamine with Z-(AA)$_n$-Asp(OBu-t) to give N-(Z-(AA)$_n$-Asp(OBu-t))-N'-substituted benzoyl-Rhodamine; and
  (c) removing the OBu-t protecting group to give N-(Z-(AA)$_n$-Asp)-N'-substituted benzoyl-Rhodamine.

In a preferred embodiment, -(AA)$_n$ is WEH, YVA, LEH, DET, DEV, DEH, VEH, LET, SHV, DEL, DGP, DEP, DGT, DLN, DEE, DSL, DVP, DEA, DSY, ELP, VED, IEP or IET.

Compounds of Formula IV also can be prepared using an anhydride in place of an acyl (alkanoyl) chloride, or an acid with a coupling reagent such as EDC in place of acyl (alkanoyl) chloride. Other reagents can be used in place of pentafluorobenzoyl chloride include, but are not limited to, 2,3,4,5-tetrafluorobenzoyl chloride, 2,4,5-trifluorobenzoyl chloride, and 2,3,4-trifluorobenzoyl chloride. The reaction is carried out in the presence of a base, such as $(Et)_3N$, $(i-Pr)_2$-NEt or pyridine, and the preferred solvent is DMF. The reaction is generally carried out at room temperature. The ratio of acyl chloride to Rhodamine is about 1:1.

The condensation reaction may be carried out using any conventional condensing agent that is used for peptide

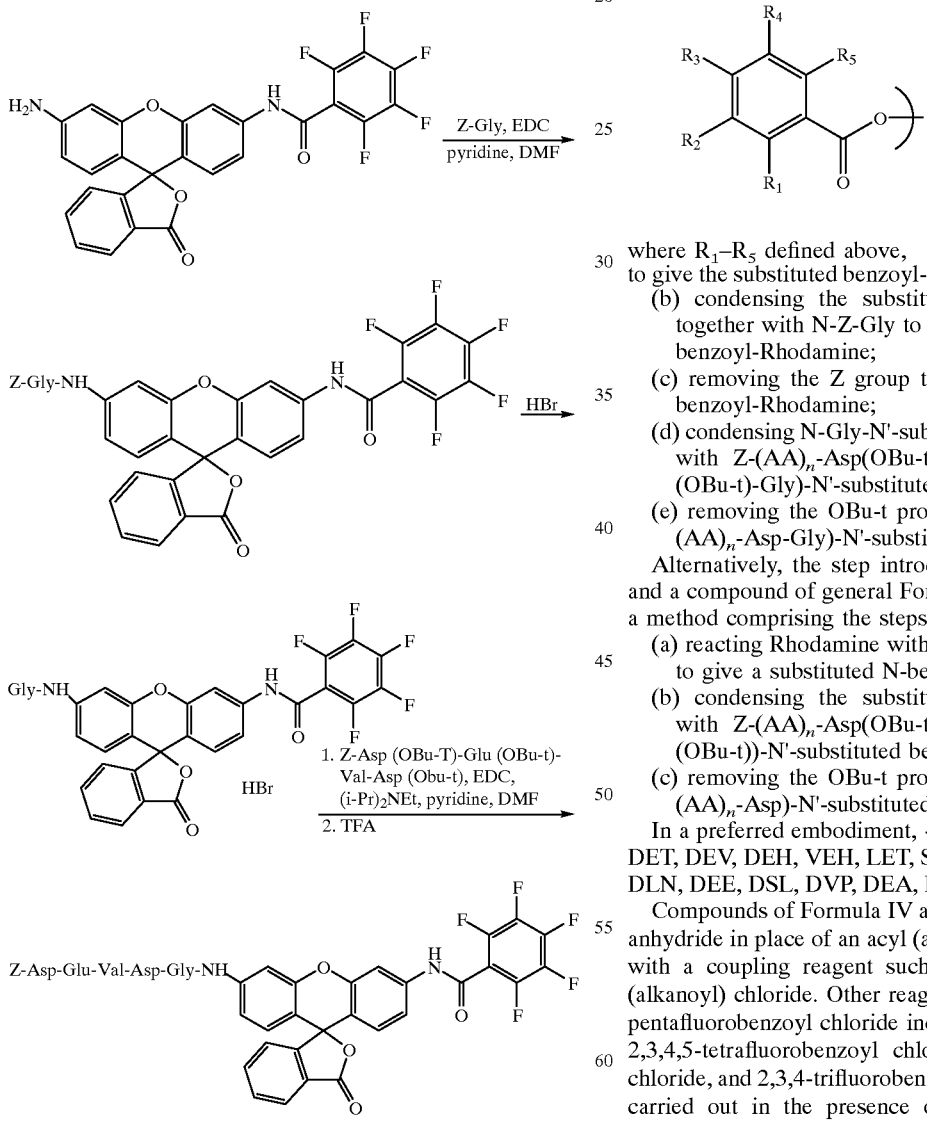

Scheme 3

Thus, the invention also relates to a method for the preparation of a compound of Formula IV, comprising the steps of:

synthesis. In a preferred embodiment, the condensing agent is EDC, EEDQ, IBCF or other known condensing agents for peptide synthesis, and the solvent for the reaction is pyridine or dimethylformamide (DMF). The reaction is generally carried out at room temperature. The ratio of condensing agent to N-pentafluorobenzoyl-Rhodamine is about 3:1 to 1.1:1 and the ratio of protected amino acid or peptide to N-pentafluorobenzoyl-Rhodamine or N-Gly-N'-pentafluorobenzoyl-Rhodamine is about 3:1 to 1.1:1.

Condensing N-substituted benzoyl-Rhodamine with a peptide such as Z-(AA)$_n$-Asp(OBu-t) to give N-(Z-(AA)$_n$-Asp(OBu-t))-N'-substituted benzoyl-Rhodamine in an one-step reaction is a preferred procedure. Thus, compounds of Formula VIII provide fluorescent dyes which can be condensed with any peptide or other structure for the preparation of fluorogenic or fluorescent compounds which are substrates for proteases or peptidases.

In principle, compounds of Formula IV also can be prepared by first condensing a peptide with a Rhodamine to give N-peptide-Rhodamine, then reacting the N-peptide-Rhodamine with pentafluorobenzoyl chloride or other acylating reagent to give for example, N-pentafluorobenzoyl-N'-peptide-Rhodamine. However, a) peptides in general are much more expensive than acyl chlorides or anhydrides, b) the condensation reaction between peptide and Rhodamine is not an efficient reaction. For these reasons it is preferred to attach the peptide to N-pentafluorobenzoyl-Rhodamine rather than attach the acyl group to N-peptide-Rhodamine.

Compounds with Formula V can be prepared as illustrated by the exemplary reactions in Scheme 4.

Scheme 4

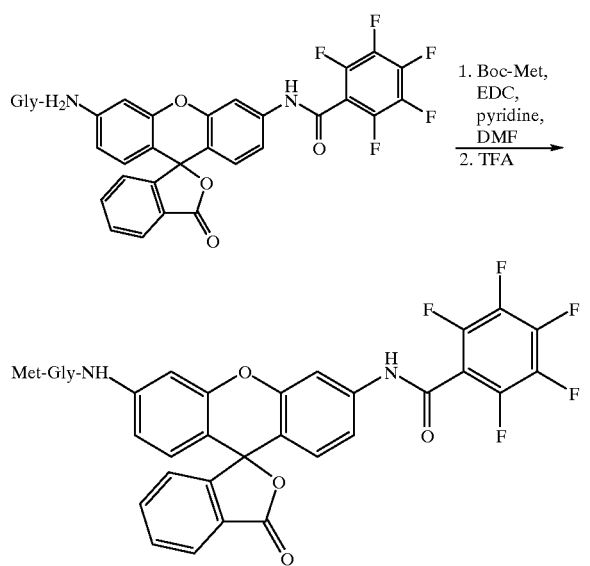

In one aspect, the invention relates to a method for determining whether a test substance has an effect on an enzyme involved in the apoptosis cascade in a test cell, comprising (a) contacting the test cell with the test substance and the reporter compound according to the invention under conditions whereby the test substance either interacts with an external membrane receptor or is taken into said cell and the reporter compound is taken into the cell, and (b) recording the fluorescence of the test cell;

wherein a change in fluorescence, either of magnitude or of wavelength, within the test cell compared to said control cell which has only been contacted with the reporter compound and not with the test substance, is an indication that said test substance has an effect on said enzyme.

The results obtained by this method can be compared to the results obtained with test compounds which are known to affect enzymes involved in the apoptosis cascade in cells to generate a measure of the relative effectiveness of the test substance. Compounds which can be used include known activitors and inhibitors of enzymes involved in the apoptosis cascade. Activators, either by direct or indirect mechanisms, of enzymes involved in the apoptosis cascade include but are not limited to known chemotherapeutic agents, such as etoposide (Yoon, H. J., et al., *Biochim Biophys Acta* 1395:110–120 (1998)) and doxorubicin (Gamen, S., et al., *FEBS Lett* 417:360–364 (1997)) which are topoisomerase II inhibitors; cisplatin (Maldonado, V., et al, *Mutat. Res.* 381:67–75 (1997)); chlorambucil (Hickman, J. A., *Cancer Metastasis Rev.* 11:121–139 (1992)) which is an alkylating agent; and fluorouracil, an RNA/DNA anti-metabolite (Hickman, J. A., *Cancer Metastasis Rev.* 11:121–139 (1992)). Inactivators, either by direct or indirect mechanisms, of enzymes involved in the apoptosis cascade include but are not limited to endogenous proteins including Bcl-2 (Joensuu, H., et al., *Am. J. Pathol.* 5:1191–1198 (1994)), the viral produced agent p35 (Miller, L. K., *J. Cell Physiol.* 173:178–182 (1997)) and the synthetic caspase inhibitor Z-VAD-FMK (An, S., and Knox, K. A., *FEBS Lett.* 386:115–122 (1996)).

In particular, the invention relates to the use of the reporter compounds having Formulae I–IV in whole-cell assays using live or dead whole cells or tissue samples to screen for compounds that inhibit either directly or indirectly an enzyme or enzymes involved in apoptosis (programmed cell death). These screening assays using compounds having Formulae I–IV are expected to lead to discovery of new drugs or new uses for known drugs that slow or block cell death in a variety of clinical conditions in which the loss of cells, tissues or entire organs occurs.

The reporter compounds having Formulae I–IV and the screening assays of the present invention can be used to identify drugs that reduce or prevent cell death in the nervous system (brain, spinal cord, and peripheral nervous system) under various conditions of ischemia and excitotoxicity, including, but not limited to, focal ischemia due to stroke and global ischemia due to cardiac arrest. The screening assays can also be used to identify compounds that reduce or prevent cell death in the nervous system due to traumatic injury (such as head trauma or spinal cord injury), viral infection or radiation-induced nerve cell death (for example, as a side-effect of cancer radiotherapy) or environmental toxicity (e.g. by certain halogenated hydrocarbons). The screening assays can also be used to identify cell death inhibitors which are useful to reduce or prevent cell death in a range of neurodegenerative disorders, including but not limited to Alzheimer's disease, Huntington's Disease, Parkinson's Disease, multiple sclerosis, amyotrophic lateral sclerosis, and spinobulbar atrophy.

The screening assays of this invention can be used to identify compounds that prevent cell death in any condition which potentially results in the death of cardiac muscle. This includes myocardial infarction, congestive heart failure and cardiomyopathy. One particular application of the screening assay is to identify compounds which reduce or prevent myocardial cell death that occurs in certain viral infections of the heart.

The screening assays of the invention can be used to identify compounds which prevent cell death of retinal neurons that occurs in disorders associated with increased intraocular pressure (such as glaucoma) or retinal disorders associated with the aging process (such as age-related macular degeneration). The assays can also be used to identify compounds which treat hereditary degenerative disorders of the retina, such as retinitis pigmentosa.

The screening assays of the invention can also be used to identify cell death inhibitors that can be used to reduce or prevent premature death of cells in the immune system, and are particularly useful in identifying inhibitors which are useful in treating immune deficiency disorders, such as acquired immune deficiency syndrome (AIDS), severe combined immune deficiency syndrome (SCIDS) and related diseases. The screening assays can also be used to identify cell death inhibitors that can be used to treat radiation-induced immune suppression.

The screening assays of the invention can also be used to identify drugs useful in organ transplantation procedures. Transplantation of human organs and tissues is a common treatment for organ failure. However, during the transplantation process, the donor organ or tissue is at risk for cell death since it is deprived of its normal blood supply prior to being implanted in the host. This ischemic state can be treated with cell death inhibitors by infusion into the donor organ or tissue, or by direct addition of the cell death inhibitors to the organ/tissue storage medium. Such cell death inhibitors can be identified using the screening assays described in this invention. Cell death inhibitors may also be used to reduce or prevent cell death in the donor organ/tissue after it has been transplanted to protect it from the effects of host immune cells which kill their targets by triggering apoptosis. The screening assays described in this invention can be used to identify cell death inhibitors useful in protecting transplanted organs from rejection. The cytoprotective effects of cell death inhibitors can also be used to prevent the death of human or animal sperm and eggs used in in vitro fertilization procedures. These inhibitors can be used during the harvesting process and can also be included in the storage medium. Cell death inhibitors useful for application in fertilization procedures can be identified using the screening assay methods described in this invention.

Mammalian cell lines and yeast cells are commonly used to produce large amounts of recombinant proteins (such as antibodies, enzymes or hormones) for industrial or medicinal use. The lifespan of some of these cell lines is limited due to growth conditions, the nature of the recombinant molecule being expressed (some are toxic) and other unknown factors. The lifespans of industrial cell lines can be extended by including cell death inhibitors in the growth medium. Cell death inhibitors useful in extending the life span of cell lines can be identified using the screening assay procedures described in this invention.

The factors governing hair growth and loss are largely unknown. There is some evidence, however, that hair follicle regression (referred to as catagen) may be due at least partially to apoptosis. Therefore, it is possible that cell death inhibitors can be used to treat hair loss that occurs due to various conditions, including but not limited to male-pattern baldness, radiation-induced or chemotherapy-induced hair loss, and hair loss due to emotional stress. There is also evidence that apoptosis may play a role in the loss of hair color. Therefore, it is possible that cell death inhibitors can also be used in treating cases of premature graying of the hair. Cell death inhibitors useful in treating or preventing hair loss or graying of the hair can be identified using the screening assay procedures described in this invention.

The death of skin epithelial cells can occur after exposure to high levels of radiation, heat or chemicals. It is possible that cell death inhibitors can be used to reduce or prevent this type of skin damage. In one particular application, cell death inhibitors can be applied in an ointment to treat acute over-exposure to the sun and to prevent blistering and peeling of the skin. Cell death inhibitors useful in treating or preventing death of skin cells can be identified using the screening assay procedures described in this invention.

Another important aspect of the present invention is use of the reporter compounds having Formulae I–IV in whole-cell assays using live or dead whole cells or tissue samples to screen for compounds that stimulate, either directly or indirectly, an enzyme or enzymes involved in apoptosis. Therefore, these screening assays using compounds having Formulae I–IV are expected to lead to discovery of new drugs or new uses for known drugs that act as anticancer agents in diseases such as cancers, tumors and cell hyperplasias etc. Compounds that may be found using the screening assays and reagents described herein are useful for treatment of cancers, tumors or tissue hyperplasias including but not limited to cancers or tumors of the brain, peripheral nervous system, eye, ear, nose, mouth, tonsils, teeth, esophagus, lung, heart, blood, blood vessels, bone marrow, lymph nodes, thymus, spleen, immune system, liver, stomach, intestinal tract, pancreas, endocrine glands and tissues, kidney, bladder, reproductive organs and glands, joints, bones and skin.

Another important aspect of the present invention is the use of reporter compounds having Formulae I–IV in whole-cell assays using yeast and other fungi, and bacteria to screen compound libraries for anti-fungal or anti-bacterial drugs that act by inducing, either directly or indirectly, the caspase cascade or other enzymes involved in apoptosis in those cells.

Another important aspect of the invention is to use the reporter compounds having Formulae I–IV to monitor the therapeutic effects of therapeutic agents or treatments given to patients with the aim of reducing, preventing or treating maladies in which apoptotic cell death is either a cause or a result.

Another important aspect of the present invention is to use the reporter compounds having Formulae V to screen for HIV protease inhibitors in HIV infected cells, comprising (a) contacting the test cell with the test substance and the reporter compound according to the invention under conditions whereby the test substance either interacts with an external membrane receptor or is taken into said cell and the reporter compound is taken into the cell, and (b) recording the fluorescence of the test cell, wherein a change in fluorescence, either of magnitude or of wavelength, within the test cell compared to a control cell which has only been contacted with the reporter compound and not with the test substance, is an indication that said test substance has an inhibiting effect on the HIV protease.

Yet another important aspect of the present invention is to use the reporter compounds having Formulae V to diagnose HIV infection, comprising (a) contacting a test cell from a patient suspected of having HIV infection with the reporter compound according to the invention under conditions whereby the reporter compound is taken into the cell, and (b) recording the fluorescence of the test cell, wherein a change in fluorescence, either of magnitude or of wavelength, within the test cell compared to a control cell which is contacted with the reporter compound, is an indication that said test cell has been infected by HIV virus and that the patient is infected with HIV.

Applying the same procedure for the screening of HIV protease inhibitors in HIV infected cells, the reporter compounds having Formula V of the present invention can be used to screen for adenovirus protease inhibitors in adenovirus infected cells. The reporter compounds having Formula V of the present invention also can be used to screen for herpes simplex virus type-1 (HSV-1) protease inhibitors in HSV-1 infected cells. The reporter compounds also can be used to screen for human cytomegalovirus (HCMV) protease inhibitors in HCMV infected cells; to screen for hepatitis C virus (HCV) protease inhibitors in HCV infected cells; as well as to screen for type-2 methionine aminopeptidase (MetAP-2) inhibitors in endothelial cells.

Additionally, using the same procedure for the diagnostics of HIV infection, the reporter compounds having Formula V of the present invention also can be used to diagnose adenovirus, herpes simplex virus type-1, human cytomegalovirus and hepatitis C virus.

Compositions within the scope of this invention include all compositions wherein the fluorogenic or fluorescent compounds of the present invention are contained in an amount which are effective to achieve its intended purpose. While amounts may vary from assay to assay, determination of optimal ranges of effective amounts of each component is within the skill of the art. Typically, the fluorogenic or fluorescent substrate compounds may be applied to cells or cell lines from mammals, e.g. humans, or other animals by incubating the cells or tissues containing the cells with the fluorogenic or fluorescent substrate at a concentration of about 0.01 nanomolar to about 1 molar, or an equivalent amount of a salt or proreporter molecule thereof in a physiologically compatible buffer. Such buffers include cellular growth medias, an example for leukemia derived cancer cells being RPMI-1640 with or without 10% fetal bovine serum. Other known cellular incubation buffers could involve isotonic solutions buffered with either phosphate or HEPES. One of ordinary skill in the art can identify other suitable buffers with no more than routine experimentation. The cells can be derived from any organ or organ system for which it is desirable to find—by means of the screening assays-drugs that could be useful in treating apoptosis-mediated disorders, e.g., neuronal cell death, heart disease, liver disease, retinal disorders, kidney, joint and bone diseases, immune system disorders, cancers, tumors and tissue hyperplasias etc.

Suitable solubilizers may be used for presenting the fluorogenic or fluorescent compounds of the present invention to tissues, cells or cell lines. Suitable solubilizers include aqueous solutions of the active compounds in water-soluble form, for example, water-soluble salts and alkaline solutions. In addition, suspensions of the compounds as appropriate oily suspensions may be presented to the cells or tissues. Suitable lipophilic solvents or vehicles include fatty oils, for example, sesame oil, or synthetic fatty acid esters, for example, ethyl oleate or triglycerides or polyethylene glycol-400 (the compounds are soluble in PEG-400) or dimethylsulfoxide (DMSO) or another suitable solubilizer. Optionally, the suspension or solution may also contain stabilizers. Optionally, electroporation or presentation of the reporter molecules in liposomes or detergents may be used to enhance the cell permeability of the fluorogenic or fluorescent reporter molecules.

Typcially, the cells are contacted with the reporter compounds of the invention and the test substance for about 30 minutes to about 5 hours, most preferably, about 1 hour.

The invention also relates to the pro-reporter derivatives of the compounds of the invention. Such pro-reporter derivatives include compounds which are cleaved in situ by endogenous enzymes to give the compounds of Formulae I–V. Such pro-reporter derivatives include lower alkyl esters of carboxyl-containing amino acid residues such as Asp and Glu. Especially preferred pro-reporter derivatives include the methyl or ethyl esters and acetoxymethyl (AM) or pivaloyloxymethyl esters of Asp- and Glu-containing compounds.

The following examples demonstrate the usefulness of the invention in measuring the activity of caspases and other enzymes involved in apoptosis in cells and tissues. The examples also demonstrate usefulness of the invention in drug screening assays that can be utilized to find enhancers or inhibitors of apoptosis. These examples are illustrative, but not limiting, of the method and compositions of the present invention. Other suitable modifications and adaptations of the variety of conditions and parameters normally encountered in in vitro assays, drug screening procedures or diagnostic procedures which are obvious to those skilled in the art are within the spirit and scope of the invention.

EXAMPLE 1

N-Pentafluorobenzoyl-Rhodamine 110

To a solution of Rhodamine 110 (1500 mg, 4.1 mmol) in dimethylformamide (40 mL) at −42° C. was added N,N-diisopropylethylamine (635.5 mg, 4.9 mmol). Then pentafluorobenzoyl chloride (1131 mg, 4.9 mmol) was added dropwise to the above solution. The reaction solution was stirred for 10 min at −42° C. and was then warmed to room temperature and kept stirring for 2 h. It was diluted with 200 mL of ice-water and extracted with ethyl acetate (3×50 mL). The organic phase was washed with brine (3×50 mL), dried over $Na_2SO_4$ and concentrated to give crude product which was purified by column chromatography (hexane/EtOAc 1:1), gave 421 mg (20%) of the title compound as a colorless solid. $R_f$=0.66 (EtOAc/hexane=1:1). $^1$H NMR ($CDCl_3$): 8.00 (d, J=8.1 Hz), 7.81 (s,1H, 7.71–7.59 (m, 3H), 7.16 (d, 1H, J=7.5 Hz), 7.01 (d, 1H, J=8.7 Hz), 6.76 (d, 1H, J=8,7 Hz), 6.55 (s, 1H), 6.36 (m, 1H), 3.93 (bs, 2H).

EXAMPLE 2

N-[Z-Val-Asp(OBut)]-N'-pentafluorobenzoyl-Rhodamine 110

To a solution of Z-Val-Asp(OBut) (103 mg, 0.25 mmol) dissolved in an anhydrous 1:1 mixture of dimethylformamide and pyridine (1 mL) at 0° C. was added EDC (47 mg, 0.25 mmol) and the solution was stirred for 20 min, then a solution of N-pentafluorobenzoyl-Rhodamine 110 (25 mg, 0.047 mmol) in the same solvent (1 mL) was added. The reaction mixture was stirred at room temperature for 5 days and was then diluted with 100 mL of water and extracted with ethyl acetate (3×50 mL). The organic phase was washed with 1N HCl (3×30 mL) and water (2×50 mL). The solution was dried over $Na_2SO_4$ and concentrated to give crude product, which was purified by column chromatography (EtOAc/$CH_2Cl_2$=1:8), gave 20 mg (46%) of the title compound as a solid. $^1$H NMR ($CDCl_3$): 9.02 (bs, 1H), 8.90 (bs, 1H), 8.01(bs, 1H), 7.80(bs, 1H), 7.70–7.50 (m, 4H), 7.31 (m, 5H), 7.22–7.10 (m, 2H), 6.80–6.75(m, 2H), 5.30 (m, 1H), 5.13 (s, 2H), 5.00 (bs, 1H), 4.04 (bs, 1H), 3.73 (1H), 3.45 (bs, 1H), 3.12 (m, 1H), 2.60 (m, 1H), 1.45 (s, 9H), 1.15–1.05 (m, 6H).

EXAMPLE 3

N-(Z-Val-Asp)-N'-pentafluorobenzoyl-Rhodamine 110

To a cooled solution (0° C.) of N-[Z-Val-Asp(OBut)]-N'-pentafluorobenzoyl-Rhodamine 110 (17 mg, 0.018 mmol) in methylene chloride (1 ml) was added 50% trifluoroacetic acid in methylene chloride (2 mL), the solution turned orange and was stirred at room temperature for 4 h. The solvent was removed and the crude product was purified by flash column chromatography to yield 15 mg (96%) of the title compound. $R_f$=0.45 (10 mL EtOAc with 5 drops $CF_3CO_2H$). $^1$H NMR ($CD_3OD$): 8.02 (d, J=6.9 Hz, 1H), 7.88 (s, 1H), 7.82–7.70 (m, 3H), 7.40–7.20 (m, 8H), 6.82 (d, J=8.4 Hz, 1H), 6.72–6.62 (m, 1H), 5.11(m, 2H), 3.90 (d, 2H), 3.79 (d, 2H), 3.18–3.00 (m, 1H), 2.96–2.78 (m, 1H), 2.05 (m, 1H), 1.05–0.98 (m, 6H).

EXAMPLE 4

N-(Z-Gly)-N'-pentafluorobenzoyl-Rhodamine 110

From Z-L-Gly (523 mg, 2.5 mmol), EDC (479 mg, 2.5 mmol) and N-pentafluorobenzoyl-Rhodamine 110 (131 mg, 0.25 mmol) was obtained 151 mg (84%) of the title compound as a solid. $^1$H NMR ($CDCl_3$): 8.82 (s, 1H), 8.52 (s, 1H), 7.97 (m, 1H), 7.68–7.60 (m, 2H), 7.38 (s, 1H), 7.32 (m, 6H), 7.16 (m, 1H), 7.08 (m, 1H), 6.68–6.60 (m, 2H), 6.00 (bs, 1H), 5.14 (s, 2H), 4.04 (bs, 2H).

EXAMPLE 5

N-Gly-N'-pentafluorobenzoyl-Rhodamine 110 HBr

To a cooled (0° C.) solution of 30% HBr in acetic acid (1 mL) was added N-(Z-Gly)-N'-pentafluorobenzoyl-Rhodamine 110 (30 mg, 0.042 mmol), the solution was then warmed to room temperature and stirred for 1 h, after concentration in vacuo, ether (20 mL) was added to precipitate the product. The filtered powder was washed with ether and dried to give 22 mg (81%) of the title compound. $^1$H NMR (DMSO): 11.32 (s, 1H), 10.71 (s, 1H), 8.09 (s, 3H), 8.04 (bs, 1H), 8.02 (bs, 1H), 7.83–7.70 (m, 3H), 7.30 (d, J=8.1 Hz, 1H), 7.21–7.16 (m, 2H), 6.87–6.81 (t, 2H), 3.81(d, J=4.8 Hz, 2H).

EXAMPLE 6

N-[Z-Asp(OBut)-Glu(OBut)-Val-Asp(OBut)]-N'-pentafluorobenzoyl-Rhodamine 110 (SEQ ID NO:5)

From Z-Asp(OBut)-Glu(OBut)-Val-Asp(OBut) (SEQ ID NO:5) (178 mg, 0.23 mmol), EDC (44 mg, 0.23 mmol) and N-pentafluorobenzoyl-Rhodamine 110 (30 mg, 0.057 mmol) was obtained 28 mg (38%) of the title compound as a solid. $^1$H NMR ($CDCl_3$): 9.10–8.18 (m, 2H), 8.05–8.04 (m, 7H), 7.40–7.22 (m, 5H), 7.22–7.05 (m, 1H), 6.85–6.65 (m, 2H), 6.20–6.00 (m, 1H), 5.15 (d, 1H), 4.90 (d, 1H), 4.58 (t, 1H), 4.42 (m, 1H), 4.15 (m, 1H), 3.95 (m, 1H), 3.10–2.65 (m, 6H), 2.45 (m, 2H), 2.10 (m, 1H), 1.50–1.38 (m, 27H), 1.10–0.95 (m, 6H).

EXAMPLE 7

N-(Z-Asp-Glu-Val-Asp)-N'-pentafluorobenzoyl-Rhodamine 110 (SEQ ID NO:5)

From N-[Z-Asp(OBut)-Glu(OBut)-Val-Asp(OBut)]-N'-pentafluorobenzoyl (SEQ ID NO:5) Rhodamine 110 (19 mg, 0.015 mmol) and 50% trifluoroacetic acid in methylene chloride (2 mL) was obtained 16.5 mg (100%) of the title compound. $R_f$=0.46 (10 mL EtOAc with 5 drops $CF_3CO_2H$). $^1$H NMR ($CD_3OD$): 8.40–7.65 (m, 7H), 7.45–7.10 (m, 6H), 6.92–6.72 (m, 2H), 5.08 (m, 2H), 4.48–4.35 (m, 2H), 4.07 (m, 1H), 3.94 (m, 1H), 3.15–2.70 (m, 6H), 2.37 (m, 2H), 2.02(m, 1H), 1.05–0.97 (m, 6H).

EXAMPLE 8

N-[Z-Val-Asp(OBut)-Gly]-N'-pentafluorobenzoyl-Rhodamine 110

From Z-Val-Asp(OBut) (52.1 mg, 0.12 mmol), EDC (24 mg, 0.12 mmol) and N-Gly-N'-pentafluorobenzoyl-Rhodamine 110 (16 mg, 0.025 mmol) was obtained 12.7 mg (52%) of the title compound as a solid. $^1$H NMR ($CDCl_3$): 8.30–7.60 (m, 6H), 7.34 (m, 5H), 7.28–7.05 (m, 2H), 6.90–6.65 (m, 2H), 5.38 (m, 1H), 5.10 (s, 2H), 4.95–4.70 (m, 1H), 4.02 (bs, 1H), 3.05–2.70 (m, 2H), 2.18 (m, 1H), 1.46 (s, 9H), 1.05–0.95 (m, 6H).

EXAMPLE 9

N-(Z-Val-Asp-Gly)-N'-pentafluorobenzoyl-Rhodamine 110

From N-[Z-Val-Asp(OBut)-Gly]-N'-pentafluorobenzoyl Rhodamine 110 (12 mg, 0.012 mmol) and 50% trifluoroacetic acid in methylene chloride (2 mL) was obtained 11.2 mg (100%) of the title compound. $R_f$=0.4 (10 mL EtOAc with 2 drops $CF_3CO_2H$). $^1$H NMR (Acetone-$d_6$): 10.42 (s, 1H), 9.62 (bs, 1H), 8.85 (bs, 1H), 8.10–7.92 (m, 2H), 7.88–7.70 (m, 2H), 7.50–7.12 (m, 10H), 6.91–6.86 (m, 1H), 6.76 (d, J=9.0 Hz, 1H), 5.15 (m, 2H), 4.85 (m, 1H), 4.00 (bs, 1H), 3.20–2.90 (m, 2H), 2.22 (bs, 1H), 0.95 (bs, 6H).

EXAMPLE 10

N-[Z-Asp(OBut)-Glu(OBut)-Val-Asp(OBut)-Gly]-N'-pentafluorobenzoyl-Rhodamine 110 (SEQ ID NO:5)

From Z-Asp-(OBut)-Glu(OBut)-Val-Asp(OBut)(SEQ ID NO:5)(86.8 mg, 0.11 mmol), i-$Pr_2$NEt (0.2 mL), EDC (21.4 mg, 0.11 mmol) and N-Gly-N'-pentafluorobenzoyl-Rhodamine 110HBr (18 mg, 0.028 mmol) was obtained 29 mg (78%) of the title compound as a solid. $R_f$=0.66 (EtOAc/$CH_2Cl_2$=1:1). $^1$H NMR ($CDCl_3$): 10.31 (s, 1H), 9.11 (s, 1H), 8.12 (s, 1H), 8.05–7.42 (m, 8H), 7.37–7.35 (m, 5H), 6.98–6.80 (m, 2H), 5.12 (t, 2H), 4.55 (bs, 2H), 4.30 (bs, 1H), 4.15–3.85 (m, 2H), 3.05–2.70 (m, 2H), 2.30 (m, 2H), 1.95 (m, 1H), 1.41 (m, 27H), 1.00 (m, 6H).

EXAMPLE 11

N-(Z-Asp-Glu-Val-Asp-Gly)-N'-pentafluorobenzoyl-Rhodamine 110 (SEQ ID NO:76)

From N-[Z-Asp(OBut)-Glu(OBut)-Val-Asp(OBut)-Gly]-N'-pentafluorobenzoyl (SEQ ID NO:76) Rhodamine 110 (11 mg, 0.008 mmol) and 50% trifluoroacetic acid in methylene chloride (1 mL) was obtained 8.5 mg (91%) of the title compound. $^1$H NMR (Acetone-$d_6$): 10.34 (s, 1H), 9.15 (s, 1H), 9.12 (s, 1H), 8.05–7.42 (m, 8H), 7.34 (m, 5H), 7.00–6.77 (m, 2H), 5.09 (m, 2H), 4.62 (m, 1H), 4.60 (m, 1H), 4.32 (m, 1H), 4.18–4.00 (m, 2H), 3.02–2.84 (m, 2H), 2.40 (m, 2H), 2.22 (m, 1H), 0.98 (m, 6H).

EXAMPLE 12

N-[Boc-Met-Gly]-N'-pentafluorobenzoyl-Rhodamine 110

From Boc-Met (15.4 mg, 0.062 mmol), EDC (11.9 mg, 0.062 mmol), i-$Pr_2$NEt (0.1 mL) and N-Gly-N'-pentafluorobenzoyl-Rhodamine 110 HBr (10 mg, 0.016 mmol) was obtained 7.8 mg (62%) of the title compound as a solid. R$_f$=0.65 (EtOAc/CH$_2$Cl$_2$=1:1). $^1$H NMR (CDCl$_3$): 8.96 (bs, 1H), 8.47 (s, 1H), 7.98 (d, J=6.9 Hz, 1H), 7.70–7.56 (m, 3H), 7.34–7.10 (m, 5H), 6.69 (m, 2H), 5.42 (bs, 1H), 4.30–4.20 (m, 1H), 4.20–4.12 (m, 2H), 2.59 (m, 2H), 2.11 (s, 3H), 2.10 (m, 2H), 1.41 (s, 9H).

EXAMPLE 13

N-(Met-Gly)-N'-pentafluorobenzoyl-Rhodamine 110. CF$_3$CO$_2$H

From N-[Boc-Met-Gly]-N'-pentafluorobenzoyl Rhodamine 110 (6.8 mg, 0.0084 mmol) and 50% trifluoroacetic acid in methylene chloride (1 mL) was obtained 4.7 mg (69%) of the title compound. $^1$H NMR (CD$_3$OD): 8.05–7.69 (m, 5H), 7.26–7.14 (m, 3H), 6.84–6.73 (m, 2H), 4.11 (m, 3H), 2.69 (t, J=7.1 Hz, 2H), 2.30–2.10 (m, 2H), 2.17 (s, 3H).

EXAMPLE 14

N-(Z-Phe)-N'-pentafluorobenzoyl-Rhodamine 110

From Z-Phe (120 mg, 0.40 mmol), EDC (77 mg, 0.40 mmol) and N-pentafluorobenzoyl-Rhodamine 110 (70 mg, 0.13 mmol) was obtained 101 mg (94%) of the title compound as a solid. $^1$H NMR (CDCl$_3$): 8.78–8.73 (m, 2H), 7.96 (bs, 1H), 7.66 (bs, 2H), 7.42–7.03 (m, 14H), 6.94 (m, 1H), 6.65–6.54 (m, 2H), 5.98 (d, 2H), 5.11–4.96 (m, 2H), 4.68 (bs, 1H), 3.23–3.05 (m, 2H).

EXAMPLE 15

N-Phe-N'-pentafluorobenzoyl-Rhodamine 110 HBr

From N-(Z-Phe)-N'-pentafluorobenzoyl-Rhodarnine 110 (70 mg, 0.087 mmol) and 30% HBr in acetic acid (1 mL) was obtained 65 mg (99%) of the title product. R$_f$=0.4 (EtOAc/CH$_2$Cl$_2$=1:1). $^1$H NMR (CD$_3$OD): 8.05 (d, J=6.9 Hz, 1H), 7.95 (d, 1H), 7.82–7.71 (m, 3H), 7.40–7.28 (m, 5H), 7.26–7.08 (m, 3H), 6.85–6.75 (m, 2H), 4.22 (t, J=6.9 Hz, 1H), 3.20–3.13 (m, 2H).

EXAMPLE 16

N-[Boc-Ala-Gly]-N'-pentafluorobenzoyl-Rhodamine 110

From Boc-Ala-Gly (28.2 mg, 0.115 mmol), EDC (21.9 mg, 0.115 mmol) and N-pentafluorobenzoyl-Rhodamine 110 (20 mg, 0.038 mmol) was obtained 26 mg (91%) of the title compound as a solid. R$_f$=0.43 (EtOAc/CH$_2$Cl$_2$=1:1). $^1$H NMR (CDCl$_3$): 8.98(s, 1H), 8.45 (s, 1H), 8.00 (d, J=6.9 Hz, 1H), 7.70–7.60 (m, 4H), 7.42–7.10 (m, 4H), 6.70(m, 2H), 5.12 (bs, 1H), 4.11 (bs, 1H), 1.41 (s, 9H).

EXAMPLE 17

N-(Ala-Gly)-N'-pentafluorobenzoyl-Rhodamine 110. CF$_3$CO$_2$H

From N-[Boc-Ala-Gly]-N'-pentafluorobenzoyl Rhodamine 110 (10 mg, 0.013 mmol) and 50% trifluoroacetic acid in methylene chloride (1 mL) was obtained 8.1 mg (81%) of the title compound. $^1$H NMR (CD$_3$OD) 8.04 (d, J=7.2 Hz, 1H), 7.94 (d, 1H), 7.83–7.73 (m, 3H), 7.25–7.16 (m, 3H), 6.84–6.74 (m, 2H), 4.10 (d, 2H), 4.03 (m, 1H), 1.57 (d, J=6.9 Hz, 3H).

EXAMPLE 18

N-[Z-Gly-Gly]-N'-pentafluorobenzoyl-Rhodamine 110

From Z-Gly-Gly (40.7 mg, 0.153 mmol), EDC (29.3 mg, 0.153 mmol), and N-pentafluorobenzoyl-Rhodamine 110 (40 mg, 0.076 mmol) was obtained 56 mg (95%) of the title compound as a solid. R$_f$=0.38 (EtOAc/CH$_2$Cl$_2$=2:1). $^1$H NMR (CDCl$_3$): 8.95 (bs, 1H), 8.53 (bs, 1H), 7.96 (d, J=7.8 Hz, 1H), 7.68–7.60 (m, 3 H), 7.53 (s, 1H), 7.35–7.27 (m, 7H), 7.20–7.08 (m, 2H), 6.69–6.62 (m, 2H), 5.73 (bs, 1H), 5.06 (s, 2H), 4.07 (d, 2H), 3.87 (d, 2H).

EXAMPLE 19

N-(Gly-Gly)-N'-pentafluorobenzoyl-Rhodamine 110 HBr

From N-[Z-Gly-Gly]-N'-pentafluorobenzoyl Rhodamine 110 (40 mg, 0.052 mmol) and 30% HBr in acetic acid (1 mL) was obtained 32 mg (86%) of the title product. $^1$H NMR (CD$_3$OD): 8.04 (d, J=7.2 Hz, 1H), 7.93 (bs, 1H), 7.83 (d, 1H), 7.82–7.70 (m, 2H), 7.25–7.17 (m, 3H), 6.84–6.74 (m, 2H), 4.23 (s, 2H), 3.80 (m, 2H).

EXAMPLE 20

N-[Z-Gly-Pro]-N'-pentafluorobenzoyl-Rhodamine 110

From Z-Gly-Pro (35.0 mg, 0.114 mmol), EDC (21.9 mg, 0.114 mmol), and N-pentafluorobenzoyl-Rhodamine 110 (20 mg, 0.038 mmol) was obtained 28 mg (91%) of the title compound as a solid. R$_f$=0.48 (EtOAc/CH$_2$Cl$_2$=2:1). $^1$H NMR (CDCl$_3$): 9.55 (s, 1H), 8.27 (bs, 1H), 8.00 (d, J=7.2 Hz, 1H), 7.70–6.98 (m, 12 H), 6.73–6.62 (m, 2H), 5.63 (bs, 1H), 5.10 (bs, 2H), 4.72 (bs, 1H), 4.04 (m, 2H), 3.60 (bs, 1H), 4.68(m, 1H), 2.42 (bs, 1H), 2.18–1.95(m, 3H).

EXAMPLE 21

N-(Gly-Pro)-N'-pentafluorobenzoyl-Rhodamine 110 HBr

From N-[Z-Gly-Pro]-N'-pentafluorobenzoyl Rhodamine 110 (20 mg, 0.025 mmol) and 30% HBr in acetic acid (1 mL) was obtained 17 mg (89%) of the title product. $^1$H NMR (CD$_3$OD): 8.04 (d, J=6.9 Hz, 1H), 7.94 (d, 1H), 7.83–7.70 (m, 3H), 7.25–7.15 (m, 3H), 6.84–6.74 (m, 2H), 4.60(m, 1H), 3.93 (s, 2H), 3.72–3.58 (m, 2H), 2.40–2.04 (m, 4H).

EXAMPLE 22

N-[Boc-Met-Gly-Gly]-N'-pentafluorobenzoyl-Rhodamine 110

From Boc-Met (10.4 mg, 0.042 mmol), EDC (7.9 mg, 0.042 mmol) and N-Gly-Gly-N'-pentafluorobenzoyl-Rhodamine 110 HBr (15 mg, 0.021) was obtained 14 mg (70%) of the title compound as a solid. R$_f$=0.27 (EtOAc). $^1$H NMR (CDCl$_3$): 8.83 (bs, 1H), 8.42 (1H), 7.99 (d, J=6.9 Hz, 1H), 7.70–7.13 (m, 7H), 6.72 (m, 2H), 5.50 (bs, 1H), 4.25–3.80 (m, 5H), 2.59 (bs, 2H), 2.20–1.95 (m, 5H), 1.37 (s, 9H).

EXAMPLE 23

N-(Met-Gly-Gly)-N'-pentafluorobenzoyl-Rhodamine 110 HBr

From N-[Boc-Met-Gly-Gly]-N'-pentafluorobenzoyl Rhodamine 110 (11 mg, 0.012 mmol) and 50% trifluoroacetic acid in methylene chloride (0.5 mL) was obtained 8.2 mg (81%) of the title compound. $^1$H NMR (CD$_3$OD) 8.04 (d, J=7.2 Hz, 1H), 7.94–7.70 (m, 4H), 7.25–7.19 (m, 3H), 6.84–6.74 (m, 2H), 4.07 (s, 1H), 4.04 (s, 1H), 2.64 (t, J=8.1 Hz, 2H), 2.22–2.10 (m, 5H).

EXAMPLE 24

N-[Z-Asp(OBut)-Glu(OBut)-Val-Asp(OBut)]-N'-(2,4-bis(dodecanemercapto)-3,5,6-trifluorobenzoyl)-Rhodamine 110 (SEQ ID NO:5)

A mixture of Z-N'-[Z-Asp(OBut)-Glu(OBut)-Val-Asp(OBut)]-N'-pentafluorobenzoyl-Rhodamine(SEQ ID NO:5) 110 (8 mg, 0.0062 mmol), 1-dodecanethiol (6.3 mg, 0.031 mmol), diisopropylethyl amine (4 mg, 0.031 mmol) in DMF (0.3 mL) was stirred at room temperature for 24 h, TLC showed the reaction is completed. The reaction was poured into water (10 mL) and extracted with EtOAc (3×10 mL). The organic phase was washed with 1N HCl (2×10 mL) and water (2×10 mL). The solution was dried over $Na_2SO_4$ and concentrated to give crude product, which was purified by column chromatography (EtOAc/hexane 1:3) to give 8.4 mg (82%) of title compound as a solid. $R_f$=0.93 (EtOAc/hexane 1:1). $^1H$ NMR ($CDCl_3$): 9.10–8.78 (m, 1H), 8.34–8.18 (m, 1H), 8.01 (d, J=6.6 Hz, 3H), 7.84–7.10 (m, 12H), 6.82–6.70 (m, 2H), 6.15–6.00 (m, 1H), 5.10–4.80 (m, 3H), 4.60–3.84 (m, 3H), 3.20–2.70 (m, 10H), 2.52 (bs, 2H), 1.56–1.22 (m, 67H), 1.01 (t, J=6.6 Hz, 6H), 0.92–0.85 (m, 6H).

EXAMPLE 25

N-(Z-Asp-Glu-Val-Asp)-N'-(2,4-bis(dodecanemercapto)-3,5,6-trifluorobenzoyl)Rhodamine 110 (SEQ ID NO:5)

From N-[Z-Asp(OBut)-Glu(OBut)-Val-Asp(OBut)]-N'-(2,4-bis(dodecanemercapto)-3,5,6-trifluorobenzoyl)-Rhodamine(SEQ ID NO:5)110 (6.1 mg, 0.0037 mmol) and 50% trifluoroacetic acid in methylene chloride (0.8 mL) was obtained 4.8 mg (84%) of the title compound. $^1H$ NMR ($CD_3OD$) 8.16–7.68 (m, 7H), 7.42–7.16 (m, 6H), 6.82–6.73 (m, 2H), 5.06 (d, 2H), 4.50–3.92 (m, 4H), 3.20–2.72 (m, 8H), 2.37 (m, 2H), 2.15 (m, 2H), 1.54–1.20 (m, 67H), 1.06–0.96 (m, 6H), 0.93–0.85 (m, 6H).

EXAMPLE 26

N-[Z-Asp(OBut)-Glu(OBut)-Val-Asp(OBut)-Gly-Gly]-N'-pentafluorobenzoyl-Rhodamine 110 (SEQ ID NO:75)

From Z-Asp(OBut)-Glu(OBut)-Val-Asp(OBut) (SEQ ID NO:75) (34.7 mg, 0.045 mmol), EDC (8.53 mg, 0.045 mmol), and N-Gly-Gly-N'-pentafluorobenzoyl-Rhodamine 110 HBr (8 mg, 0.011 mmol) was obtained 8 mg (49%) of the title compound as a solid. $R_f$=0.27 (EtOAc/$CH_2Cl_2$=2:1). $^1H$ NMR ($CDCl_3$): 8.77 (m, 1H), 8.64–8.14 (m, 2H), 8.03–7.10 (m, 13H), 6.80–6.70 (m, 2H), 6.22–5.98 (m, 1H), 5.15 (m, 2H), 4.78–3.76 (m, 8H), 3.00–2.74 (m, 4H), 2.60–2.32 (m, 2H), 2.06 (m, 2H), 1.45–1.27 (m, 27H), 0.97–0.90 (m, 6H).

EXAMPLE 27

N-(Z-Asp-Glu-Val-Asp-Gly-Gly)-N'-pentafluorobenzoyl-Rhodamine 110 (SEQ ID NO:75)

From N-[Z-Asp(OBut)-Glu(OBut)-Val-Asp(OBut)-Gly-Gly]-N'-pentafluorobenzoyl-Rhodamine 110 (SEQ ID NO:75) (6.6 mg, 0.0045 mmol) and 50% trifluoroacetic acid in methylene chloride (0.5 mL) was obtained 5.4 mg (98%) of the title compound. $^1H$ NMR ($CD_3OD$) 8.16–7.68 (m, 7 H), 7.37–7.20 (m, 6H), 6.83–6.73 (q, 2H), 5.07 (s, 2H), 4.69–4.85 (m, 8H), 2.92–2.70 (m, 4H), 2.42 (bs, 2H), 2.08 (bs, 2H),1.30 (s, 1H), 1.02–0.91 (m, 6H).

EXAMPLE 28

N-(Asp-Glu-Val-Asp)-N'-pentafluorobenzoyl-Rhodamine 110 HBr (SEQ ID NO:5)

From N-[Z-Asp(OBut)-Glu(OBut)-Val-Asp(OBut)]-N'-pentafluorobenzoyl-Rhodamine(SEQ ID NO:5)110 (9.8 mg, 0.0076 mmol) and 30% HBr in acetic acid (1 mL) was obtained 7.1 mg (92%) of the title compound. $^1H$ NMR ($CD_3OD$): 8.08–7.72 (m, 10 H), 4.42 (m, 1H), 4.21 (m, 1H), 3.09–2.83 (m, 4H), 2.42 (m, 2H), 2.10 (m, 2H), 1.30 (bs, 1H), 1.01 (m, 6H).

EXAMPLE 29

N-[Ac-Asp(OBut)-Glu(OBut)-Val-Asp(OBut)]-N'-pentafluorobenzoyl-Rhodamine 110 (SEQ ID NO:5)

From Ac-Asp(OBut)-Glu(OBut)-Val-Asp(OBut)(SEQ ID NO:5)(206.1 mg, 0.3 mmol), EDC (57.5 mg, 0.3 mmol), and N-pentafluorobenzoyl-Rhodamine 110 (52 mg, 0.1 mmol) was obtained 63 mg (53%) of the title compound as a solid. $R_f$=0.43 (EtOAc/$CH_2Cl_2$=1:1). $^1H$ NMR ($CDCl_3$): 9.80–9.06 (m, 1H), 8.82–8.42 (m, 1H), 8.03–6.64 (m, 10H), 5.00–3.90 (m, 4H), 3.22–2.42 (m, 6H), 2.30–2.00 (m, 2H), 2.06 (s, 3H), 1.49–1.35 (m, 27H), 1.11–1.00 (m, 6H).

EXAMPLE 30

N-(Ac-Asp-Glu-Val-Asp)-N'-pentafluorobenzoyl-Rhodamine 110 (SEQ ID NO:5)

From N-[Ac-Asp(OBut)-Glu(OBut)-Val-Asp(OBut)]-N'-pentafluorobenzoyl-Rhodamine(SEQ ID NO:5)110 (40 mg, 0.034 mmol) and 50% trifluoroacetic acid in methylene chloride (1 mL) was obtained 31 mg (89%) of the title compound. $^1H$ NMR ($CD_3OD$) 8.08–7.68 (m, 8H), 6.83–6.74 (m, 2H), 4.70–4.65 (m, 1H), 4.42–4.30 (m, 1H), 4.12–4.04 (m, 1H), 3.98–3.92 (m, 1H), 3.08–2.72 (m, 4H), 2.38 (m, 2H), 2.12 (m, 2H), 1.98–1.94 (t, 3H), 1.30 (s, 1H), 1.04–0.96 (m, 6H).

EXAMPLE 31

N-(4-Dodecanemercapto-2,3,5,6-tetrafluorobenzoyl)-Rhodamine 110 (I) and N-(2,4-Bis(dodecanemercapto)-3,5,6-trifluorobenzoyl)-Rhodamine 110 (II)

A mixture of N-pentafluorobenzoyl-Rhodamine 110 (26.2 mg, 0.05 mmol), 1-dodecanethiol (12.1 mg, 0.06 mmol), diisopropylethylamine (8.4 mg, 0.065 mmol) in dimethylformamide (2 mL) was stirred at 25° C. for 16 h, TLC showed the reaction is completed. The solution is diluted with water (10 mL), extracted with EtOAc (3×10 mL), washing with water (3×10 mL). The solution was dried over $Na_2SO_4$ and concentrated to give crude product, which was purified by column chromatography (EtOAc/hexane=1:2), gave two compounds. Compound I, 15 mg (42%), $R_f$=0.59 (EtOAc/hexane=1:1). $^1H$ NMR ($CDCl_3$): 8.01–7.59 (m, 6H), 7.15 (d, J=7.5 Hz, 1H), 7.02 (d, J=8.4 Hz, 1H), 6.74 (d, J=8.7 Hz, 1H), 6.54–6.32 (m, 2H), 3.93 (s, 2H), 2.89 (t, J=7.2 Hz, 2H), 1.54 (m, 2H), 1.23 (bs, 18H), 0.88 (t, J=6.0 Hz, 3H). Compound II, 2.5 mg (5.6%), $R_f$=0.76 (EtOAc/hexane=1:1). $^1H$ NMR ($CDCl_3$): 8.00–7.58 (m, 6H), 7.18–6.39 (m, 5H), 3.93 (s, 2H), 2.95 (bs, 2H), 2.86 (t, J=7.5 Hz, 2H), 1.58 (s, 4H), 1.62–1.50 (m, 4H), 1.38–1.20 (m, 36H), 0.88 (t, J=0.57 Hz, 6H).

EXAMPLE 32

N-[Z-Glu(OBut)-Val-Asp(OBut)]-N'-pentafluorobenzoyl-Rhodamine 110

From Z-Glu(OBut)-Val-Asp(OBut) (92 mg, 0.15 mmol), EDC (29 mg, 0.15 mmol), and N-pentafluorobenzoyl- Rhodamine 110 (20 mg, 0.038 mmol) was obtained 34 mg (79%) of the title compound as a solid. $^1$H NMR (CDCl$_3$): 8.80 (bs, 1H), 8.36 (bs, 1H), 7.99 (d, 1H, J=3.3 Hz), 7.83 (bs, 1H), 7.80 (bs, 1H), 7.63 (m, 4 H), 7.43 (m, 6H), 7.30 (m, 5H), 5.08 (s, 2H), 4.64 (m, 1H), 4.03 (m, 2H), 2.31 (m, 2H), 2.23 (m, 2H), 1.88 (m, 2H), 1.41 (s, 18H), 0.95 (m, 6H).

EXAMPLE 33

N-(Z-Glu-Val-Asp)-N'-pentafluorobenzoyl-Rhodamine 110

From N-[Z-Glu(OBut)-Val-Asp(OBut)]-N'-pentafluorobenzoyl Rhodamine 110 (34 mg, 0.03 mmol) and 50% trifluoroacetic acid in methylene chloride (2 ml) was obtained 23 mg (76%) of the title compound as a solid. $^1$H NMR (acetone-d$_6$): 10.32 (bs, 1H), 9.14 (bs, 1H), 8.25 (bs, 1H), 8.13 (bs, 1H), 8.03 (m, 3H), 7.78 (m, 3H), 7.46 (m, 2H), 6.89 (d, 1H, J=9 Hz), 6.78 (dd, 1H, J=8.4, 3.9 Hz), 5.06 (s, 2H), 4.65 (m, 1H), 4.17 (m, 1H), 3.94 (m, 1H), 2.98 (m, 2H), 2.38 (m, 2H), 1.97 (m, 3H), 0.97 (d, 6H, J=6 Hz).

EXAMPLE 34

N-[Z-Glu(OBut)-Val-Asp(OBut)-Gly]-N'-pentafluorobenzoyl-Rhodamine 110 (SEQ ID NO:71)

From Z-Glu(OBut)-Val-Asp(OBut) (57 mg, 0.09 mmol), EDC (17.8 mg, 0.09 mmol), and N-Gly-N'-pentafluorobenzoyl-Rhodamine 110 (15 mg, 0.023 mmol) was obtained 13 mg (45%) of the title compound (13 mg) as a solid. $^1$H NMR (CDCl$_3$): 8.61 (bs, 1H), 7.97 (bs, 1H), 7.94 (d, 1H, J=0.6 Hz), 7.75 (d, 1H, J=2.4 Hz)), 7.63 (m, 3H), 7.33 (s, 5 H), 7.13 (d, 1H, J=6.9 Hz), 7.14 (dd, 1H, J=8.4, 1.8 Hz), 6.65 (d, 1H, J=8.4 Hz), 6.48 (m, 2H), 6.32 (dd, 1H, J=8.4, 2.1 Hz), 5.09 (s, 2H), 4.46 (m, 1H), 4.38 (m, 1H), 4.27 (m, 1H), 3.99 (s, 2H), 2.41 (m, 2H), 2.16 (m, 2H), 1.95 (m, 1H), 1.43 (s, 18H), 0.92 (m, 6H).

EXAMPLE 35

N-(Boc-Leu-Met)-N'-pentafluorobenzoyl-Rhodamine 110

From Boc-Leu-Met (96 mg, 0.27 mmol), EDC (51.3 mg, 0.27 mmol), and N-pentafluorobenzoyl-Rhodamine 110 (30 mg, 0.053 mmol) was obtained 26 mg (56%) of the title compound (26 mg) as a solid. $^1$H NMR (CDCl$_3$): 9.02 (bs, 1H), 8.25 (bs, 1H), 8.23 (bs, 1H), 8.13 (bs, 1H), 8.00 (d, 1H, J=6.6 Hz), 7.65 (m, 3H), 7.38 (m, 3 H), 7.15 (m, 1H), 7.13 (m, 2H), 4.78 (m, 1H), 4.06 (m, 1H), 2.63 (m, 2H), 2.13 (s, 3H), 1.71 (m, 2H), 1.59 (s, 9H), 1.53 (m, 2H), 1.45 (d, 3H, J=3 Hz), 1.39 (d, 3H, J=3.3 Hz).

EXAMPLE 36

N-(Boc-Met)-N'-pentafluorobenzoyl-Rhodamine 110

From Boc-Met (111 mg, 0.44 mmol), EDC (85.4 mg, 0.44 mmol), and N-pentafluorobenzoyl-Rhodamine 110 (25 mg, 0.045 mmol) was obtained 33 mg (92%) of the title compound as a solid. $^1$H NMR (acetone-d$_6$): 9.33 (bs, 1H), 8.92 (bs, 1H), 8.59 (bs, 1H), 7.95 (m, 1H), 7.65 (m, 3H), 7.33 (m, 2H), 7.07 (m, 2H), 6.71 (dd, 1H, J=8.55, 6.6 Hz), 6.59 (dd, 1H, J=20.4 Hz, 8.4 Hz), 4.48 (m, 1H), 2.62 (m, 2H), 2.11 (s, 3H), 1.85 (m, 2H), 1.46 (s, 9H).

EXAMPLE 37

N-Met-N'-pentafluorobenzoyl-Rhodamine 110

From N-(Boc-Met)-N'-pentafluorobenzoyl-Rhodamine 110 (5 mg, 0.0066 mmol) and trifluoroacetic acid (1 ml) was obtained 2 mg (46%) of the title compound as a solid. $^1$H NMR (acetone-d$_6$): 10.41 (bs, 1H), 8.02 (bs, 1H), 7.96 (s, 1H), 7.78 (m, 3H), 7.34 (m, 4H), 6.88 (m, 3H), 5.4 (bs, 2H), 2.74 (m, 2H), 2.49 (m, 2H), 2.07 (s, 3H).

EXAMPLE 38

N-(Z-Ala)-N'-pentafluorobenzoyl-Rhodamine 110

From Z-Ala (100 mg, 0.45 mmol), EDC (86 mg, 0.45 mmol), and N-pentafluorobenzoyl-Rhodamine 110 (25 mg, 0.045 mmol) was obtained 24 mg (69%) of the title compound as a solid. $^1$H NMR (acetone-d$_6$): 9.24 (bd, 1H, J=20.7 Hz), 8.89 (bs, 1H), 8.63 (bd, 1H, J=25.2 Hz), 7.96 (m, 1H), 7.65 (m, 3H), 7.28 (m, 5 H), 7.09 (m, 3H), 6.83 (s, 1H), 6.60 (m, 2H), 5.12 (m, 2H), 4.55(m, 1H), 1.47 (d, 3H, J=5.7 Hz).

EXAMPLE 39

N-Ala-N'-pentafluorobenzoyl-Rhodamine 110

From N-(Z-Ala)-N'-pentafluorobenzoyl-Rhodamine 110 (10 mg, 0.013 mmol) and 30% hydrogen bromide in acetic acid (1 ml) was obtained 8 mg (90%) of the title compound as a brown solid. $^1$H NMR (CDCl$_3$): 8.81 (bs, 1H), 8.32 (bs, 1H), 8.29 (s, 1H), 7.97 (dd, 1H, J=7.2, 1.2 Hz), 7.95 (d, 1H, J=2.4 Hz), 7.64 (m, 2H), 7.14 (d, 1H, J=6 Hz), 7.05 (dd, 1H, J=8.7, 2.1 Hz), 6.69 (d, 1H, J=8.4 Hz), 6.47 (m, 2H), 4.45 (bs, 2H), 4.21 (m, 1H), 0.93 (m, 3H).

EXAMPLE 40

N-(Z-Ala-Ala)-N'-pentafluorobenzoyl-Rhodamine 110

From Z-Ala-Ala (262 mg, 0.9 mmol), EDC (172 mg, 0.9 mmol), and N-pentafluorobenzoyl-Rhodamine 110 (50 mg, 0.09 mmol) was obtained 32 mg (49%) of the title compound as a solid. $^1$H NMR (CDCl$_3$): 9.44 (bs, 1H), 9.21 (bs, 1H), 8.85 (bs, 1H), 8.78 (bs, 1H), 7.98 (d, 1H, J=6.5 Hz), 7.63 (m, 3H), 7.28 (m, 5H), 7.19 (m, 4H), 6.62 (m, 2H), 5.08 (s, 2H), 4.71 (m, 1H), 4.26 (m, 1H), 1.37 (m, 6H).

EXAMPLE 41

N-(Ala-Ala)-N'-pentafluorobenzoyl-Rhodamine 110

From N-(Z-Ala-Ala)-N'-pentafluorobenzoyl-Rhodamine 110 (25 mg, 0.033 mmol) and 30% hydrogen bromide in acetic acid (1 ml) was obtained 21 mg (93%) of the title compound as a solid. $^1$H NMR (CDCl$_3$): 8.84 (bs, 1H), 8.79 (bs, 1H), 8.65 (bs, 1H), 7.99 (d, 1H, J=7.2 Hz), 7.66 (m, 3H), 7.20 (m, 4H), 6.77 (m, 2H), 5.25 (m, 1H), 3.79 (m, 1H),1.67 (bs, 2H), 1.43 (m, 6H).

EXAMPLE 42

N-(Z-Ala-Ala-Ala-Ala)-N'-pentafluorobenzoyl-Rhodamine 110 (SEQ ID NO:77)

From Z-Ala-Ala (79 mg, 0.27 mmol), EDC (52 mg, 0.27 mmol), and N-(Ala-Ala)-N'-pentafluorobenzoyl-Rhodamine 110 (18 mg, 0.027 mmol) was obtained 16 mg (61%) of the title compound as a solid. $^1$H NMR (acetone-d$_6$): 10.42 (bs, 1H), 9.43 (bs, 1H), 8.10 (bs, 1H), 8.04 (dd, 1H, J=5.1, 1.8 Hz), 8.00 (d, 1H, J=4.8 Hz), 7.77 (m, 4 H), 7.50 (d, 1H, J=8.4 Hz), 7.46 (d, 1H, J=8.4 Hz), 7.35 (m, 5H), 6.88 (d, 1H, J=8.4 Hz), 6.78 (dd, 1H, J=8.7, 2.1 Hz), 5.08 (m, 2H), 4.50 (m, 2H), 4.21 (m, 2H), 1.39 (m, 12H).

EXAMPLE 43

N-(Z-Arg-Gly)-N'-pentafluorobenzoyl-Rhodamine 110

From Z-Arg (216 mg, 0.7 mmol), EDC (134 mg, 0.7 mmol), and N-Gly-N'-pentafluorobenzoyl-Rhodamine 110 (50 mg, 0.07 mmol) was obtained 18 mg (29%) of the title compound as a solid. $^1$H NMR (acetone-$d_6$): 10.35 (bs, 1H), 9.21 (bs, 1H), 8.85 (bs, 1H), 8.78 (bs, 1H), 7.98 (d, 1H, J=6.5 Hz) 7.63 (m, 3H), 7.28 (m, 5H), 7.19 (m, 4H), 6.62 (m, 2H), 5.08 (s, 2H), 4.71 (m, 1H), 4.26 (m, 1H), 1.37 (m, 6H).

EXAMPLE 44

N-(2,3,4,5-Tetrafluorobenzoyl)-Rhodamine 110

From Rhodamine 110 (500 mg, 1.36 mmol) N,N-diisopropylethylamine (264 mg, 2.04 mmol) and 2,3,4,5-tetrafluorobenzoyl chloride (433 mg, 2 mmol) was obtained 121 mg (18%) of title compound as colorless solid. $^1$H NMR (CDCl$_3$): 8.40 (d, J=12.9 Hz, 1H), 8.01 (d, J=7.5 Hz, 1H), 7.81 (d, 1H), 7.71–7.59 (m, 3H), 7.16 (d, J=7.2 Hz, 1H), 7.01 (dd, 1H, J1=9 Hz, J2=2.4 Hz, 1H), 6.76 (d, J=8.7 Hz, 1H), 6.50 (m, 1H), 6.34 (dd, m, 1H), 3.93 (bs, 2H).

EXAMPLE 45

N-[Ac-Asp(OBut)-Glu(OBut)-Val-Asp(OBut)]-N'-(2,3,4,5-tetrafluorobenzoyl)-Rhodamine 110 (SEQ ID NO:5)

From Ac-Asp(OBut)-Glu(OBut)-Val-Asp(OBut)(SEQ ID NO:5)(163 mg, 0.24 mmol), EDC (46 mg, 0.24 mmol) and N-(2,3,4,5-tetrafluorobenzoyl)-Rhodamine 110 (40 mg, 0.079 mmol) was obtained 25 mg (27%) of title compound as a solid. $^1$H NMR (CDCl$_3$): 9.80–9.06 (m, 1H), 8.82–8.42 (m, 2H), 8.03–6.64 (m, 10H), 5.00–3.90 (m, 4H), 3.22–2.42 (m, 6H), 2.30–2.00 (m, 2H), 2.06 (s, 3H), 1.49–1.35 (m, 27H), 1.11–1.00 (m, 6H).

EXAMPLE 46

N-(Ac-Asp-Glu-Val-Asp)-N'-(2,3,4,5-tetrafluorobenzoyl)-Rhodamine 110 (SEQ ID NO:5)

From N-[Ac-Asp(OBut)-Glu(OBut)-Val-Asp(OBut)]-N'-(2,3,4,5-tetrafluorobenzoyl) (SEQ ID NO:5) Rhodamine 110 (22 mg, 0.018 mmol), methylene chloride (1 ml) and trifluoroacetic acid (1 mL) was obtained 18 mg (99%) of the title compound. $^1$H NMR (CD$_3$OD) 8.40–7.40 (m, 9H), 6.92–6.72 (d, J=7.8 Hz, 2H), 4.87 (m, 2H), 4.30–4.15 (m, 1H), 3.94 (m, 1H), 3.15–2.70 (m, 6H), 2.58 (m, 2H), 2.32 (m, 2H), 2.17–2.14 (d, 3H), 1.05–0.97 (m, 6H).

EXAMPLE 47

N-[Ac-Asp(OEt)-Glu(OEt)-Val-Asp(OEt)]-N'-pentafluorobenzoyl-Rhodamine 110 (SEQ ID NO:5)

From Ac-Asp(OEt)-Glu(OEt)-Val-Asp(OEt) (SEQ ID NO:5) (138 mg, 0.23 mmol), EDC (44 mg, 0.23 mmol) and N-pentafluorobenzoyl-Rhodamine 110 (40 mg, 0.076 mmol) was obtained 38 mg (45%) of title compound as a solid. $^1$H NMR (CDCl$_3$): 9.40–9.06 (m, 1H), 8.82–8.42 (m, 1H), 8.10–6.64 (m, 10H), 5.10–3.90 (m, 10H), 3.22–2.42 (m, 6H), 2.30–2.00 (m, 2H), 2.06 (s, 3H), 1.32–1.08 (m, 12H), 1.05–0.95 (m, 6H).

EXAMPLE 48

N-[Ddz-Asp(OBut)-Glu(OBut)-Val-Asp(OBut)]-N'-pentafluorobenzoyl-Rhodamine 110 (SEQ ID NO:5)

From Ddz-Asp(OBut)-Glu(OBut)-Val-Asp(OBut) (SEQ ID NO:5) (278 mg, 0.32 mmol), EDC (61.3 mg, 0.32 mmol) and N-pentafluorobenzoyl-Rhodamine 110 (48 mg, 0.092 mmol) was obtained 27 mg (21%) of title compound as a solid. $^1$H NMR (CDCl$_3$): 9.10–8.40 (m, 3H), 8.10–7.10 (m, 12H), 6.02–5.90 (m, 1H), 4.86 (m, 1H), 4.40–3.90 (m, 4H), 3.73 (m, 6H), 3.00–2.00 (m, 6H), 2.06 (s, 3H), 1.49–1.35 (m, 33H), 1.11–1.00 (m, 6H).

EXAMPLE 49

N-[H$_2$N-Asp(OBut)-Glu(OBut)-Val-Asp(OBut)]-N'-pentafluorobenzoyl-Rhodamine 110 (SEQ ID NO:5)

To a cooled solution (0° C.) of N-[Ddz-Asp(OBut)-Glu(OBut)-Val-Asp(OBut)]-N'-pentafluorobenzoyl(SEQ ID NO:5) Rhodamine 110 (18 mg, 0.013 mmol) in methylene chloride (1 ml) was added trifluoroacetic acid (0.07 mL), the solution was stirred at room temperature for 10 min. It was neutralized with N-methylmorpholine (NMM), concentrated and purified by column chromatography, yielded 14 mg (78%) of the title compound. $^1$H NMR (CD$_3$OD) 10.36 (bs, 1H), 9.45 (s, 1H), 9.33 (s, 1H), 8.20–7.38 (m, 8H), 6.92–6.72 (m, 2H), 5.00–3.92 (m, 6H), 3.00 (m, 2H), 2.60–1.90 (m, 6H), 1.60–1.10 (m, 30H), 1.05–0.97 (m, 6H).

EXAMPLE 50

N-[Octanoyl-Asp(OBut)-Glu(OBut)-Val-Asp(OBut)]-N'-pentafluorobenzoyl-Rhodamine 110 (SEQ ID NO:5)

A mixture of N-[H$_2$N-Asp(OBut)-Glu(OBut)-Val-Asp(OBut)]-N'-pentafluorobenzoyl(SEQ ID NO:5) Rhodamine 110 (7 mg, 0.0058 mmol), N-succinimidyl caprylate (2.78 mg, 0.011 mmol) and 4-methyl morpholine (0.59 mg) in ethyl acetate (1.1 ml) was stirred at room temperature for 3 days. The solvent was removed and the residue was purified by column chromatography, gave 5 mg (64%) of the title compound. $^1$H NMR (CDCl$_3$) 9.83 (d, 1H), 9.10 (d, 1H), 8.79 (d, 1H), 8.41–7.00 (m, 8H), 6.80–6.40 (m, 2H), 5.05–3.72 (m, 4H), 3.30–1.95 (m, 8H), 1.60–0.90 (m, 47H).

EXAMPLE 51

N-(Octanoyl-Asp-Glu-Val-Asp)-N'-pentafluorobenzoyl-Rhodamine 110 (SEQ ID NO:5)

From N-[Octanoyl-Asp(OBut)-Glu(OBut)-Val-Asp(OBut)]-N'-pentafluorobenzoyl Rhodamine 110 (SEQ ID NO:5) (3.0 mg, 0.0024 mmol) and 50% trifluoroacetic acid in methylene chloride (0.4 mL) was obtained 2.6 mg (96%) of the title compound. $^1$H NMR (CD$_3$OD) 8.15–7.20 (m, 8H), 6.83–6.75 (m, 2H), 4.70–3.90 (m, 4H), 3.15–1.90 (m, 8H), 1.68–0.95 (m, 19H).

EXAMPLE 52

N-[Pentafluorobenzoyl-Asp(OBut)-Glu(OBut)-Val-Asp(OBut)]-N'-pentafluorobenzoyl-Rhodamine 110 (SEQ ID NO:5)

A mixture of N-[H$_2$N-Asp(OBut)-Glu(OBut)-Val-Asp(OBut)]-N'-pentafluorobenzoyl (SEQ ID NO:5) Rhodamine 110 (7 mg, 0.0058 mmol), N-succinimidyl pentafluorobenzoylate (5.2 mg, 0.017 mmol) and 4-methyl morpholine (1.18 mg, 0.0116 mmol) in ethyl acetate (2 ml) was stirred at room temperature for 3 days. The solvent was removed and the residue was purified by column chromatography, gave 3.1 mg (40%) of the title compound. $^1$H NMR (CDCl$_3$) 9.03–7.12(m, 11H), 6.86–6.70 (m, 2H), 5.05 (m, 1H), 4.93 (m, 1H), 4.54 (m, 1H), 4.05 (m, 1H), 3.15–2.00 (m, 6H), 1.47–1.24 (m, 28H), 0.89 (t, 6H).

EXAMPLE 53

N-(Pentafluorobenzoyl-Asp-Glu-Val-Asp)-N'-pentafluorobenzoyl-Rhodamine 110 (SEQ ID NO:5)

From N-[pentafluorobenzoyl -Asp(OBut)-Glu(OBut)-Val-Asp(OBut)]-N'-pentafluorobenzoyl (SEQ ID NO:5) Rhodamine 110 (3.0 mg, 0.0022 mmol) and 50% trifluoroacetic acid in methylene chloride (0.5 mL) was obtained 0.9 mg (35%) of the title compound. $^1$H NMR (CD$_3$OD) 8.20–6.80 (m, 10H), 4.60–3.40 (m, 4H), 3.15–1.90 (m, 6H), 1.68–0.95 (m, 7H).

EXAMPLE 54

Fluorescence of N-pentafluorobenzoyl-Rhodamine 110 (R110-PFB) compared to Rhodamine 110

A standard curve consisting of 7 concentrations of N-pentafluorobenzoyl-Rhodamine 110 (0.5 to 20 μM) in a volume of 100 μL was prepared. The fluorescence of each concentration was measured (in triplicate) using a BioTek fluorescent microplate reader, and the signal was plotted as a function of dye concentration. The N-pentafluorobenzoyl-Rhodamine 110 curve was compared to a standard curve of R110 fluorescence prepared in the same way. At each concentration tested, R110 showed a 20 to 50-fold higher fluorescence than N-pentafluorobenzoyl-Rhodamine 110 (FIG. 1). These data indicate that, under cell-free conditions, N-pentafluorobenzoyl-Rhodamine 110 is a weaker fluorescent dye compared to Rhodamine 110.

EXAMPLE 55

Staining of Cells with N-pentafluorobenzoyl-Rhodamine 110 and Rhodamine 110

Figure 2A:
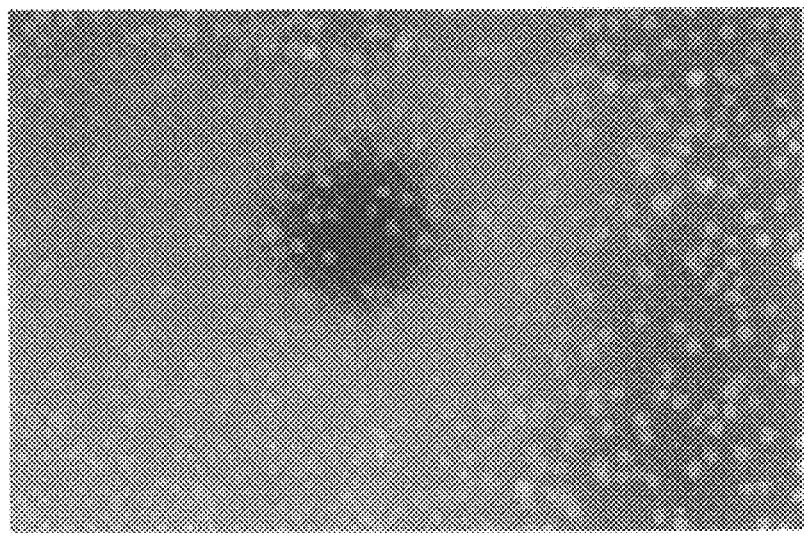
FIGS. 2A and 2B depict photographs showing the staining of cells with N-pentafluorobenzoyl-R110 (2B) compared to R110 (2A).
Figure 2B:
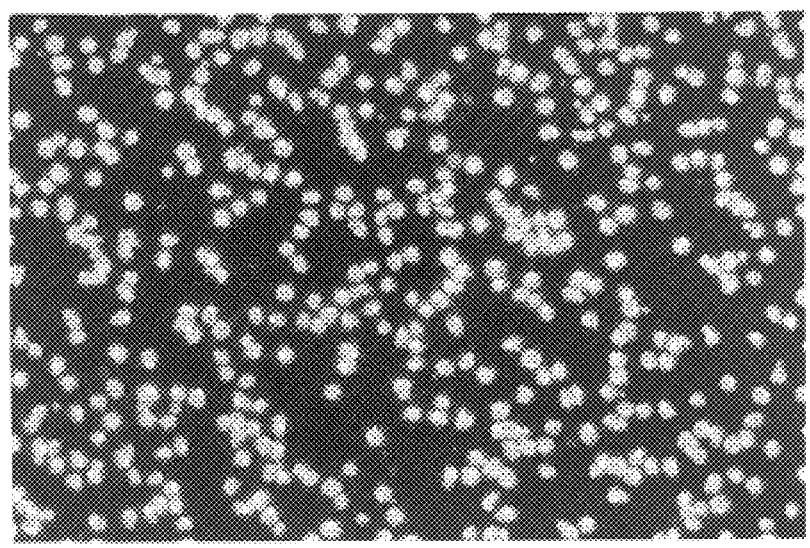

HL-60 cells (about 2×10$^6$) were placed in 50 μL of Iscove's medium, without serum or phenol-red, containing 10 μM N-pentafluorobenzoyl-Rhodamine 110. A parallel sample was placed in the same medium containing 10 μM Rhodamine 110. The cells were incubated for 2 hours at 37° C. in a CO$_2$ incubator, recovered by centrifugation, and resuspended in 50 μL of fresh medium without N-pentafluorobenzoyl-Rhodamine 110 or Rhodamine 110. Aliquots of each cell suspension were placed in microslides and viewed on a Nikon inverted microscope with epifluorescent illumination. Cells incubated with Rhodamine 110 initially emitted a strong yellowish-green fluorescent signal, but this signal rapidly faded with time as the dye leaked out of the cells into the surrounding medium. By contrast, cells incubated with N-pentafluorobenzoyl-Rhodamine 110 emitted a strong yellowish-green fluorescent signal, whose intensity remained constant during viewing periods of at least 15 minutes. The N-pentafluorobenzoyl-Rhodamine 110 was well retained by the cells, as shown by the lack of fluorescence in the surrounding medium (FIGS. 2A and 2B). This experiment demonstrates that N-pentafluorobenzoyl-Rhodamine 110 can stain cells as intensely as Rhodamine 110, but that, unlike Rhodamine 110, the N-pentafluorobenzoyl-Rhodamine 110 signal remains strong over time.

EXAMPLE 56

Cleavage of N-Gly-R110-PFB by HL-60 Lysates

Figure 3:
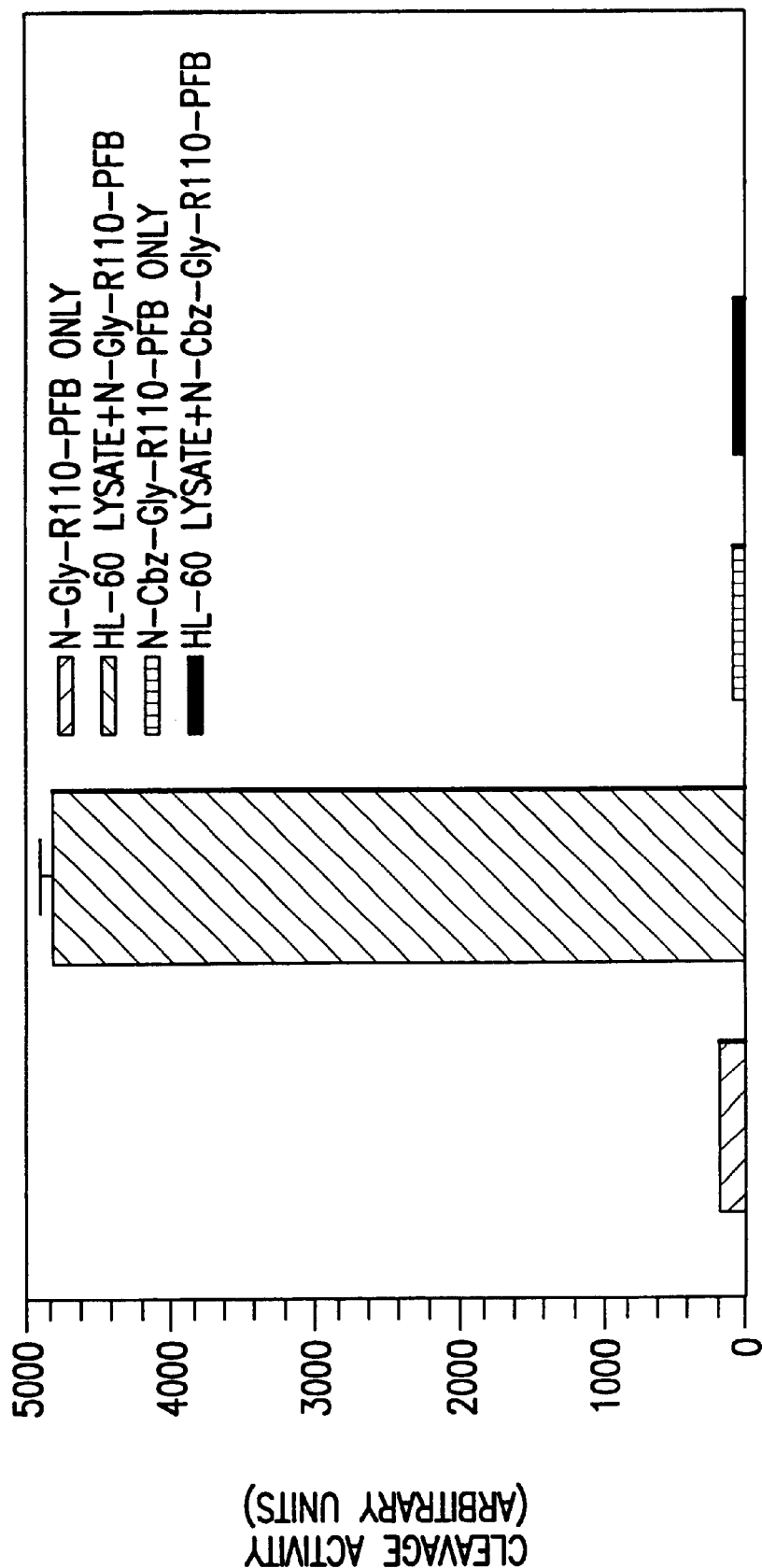
FIG. 3 depicts a bar graph showing the cleavage of N-Gly-R110-PFB and N-Cbz-Gly-R110-PFB by HL-60 Cell Lysates.

N-Gly-R110-PFB was incubated with a lysate made from HL-60 cells, and the amount of fluorescence was measured at various times after incubation at 37° C. Parallel samples were run using the control substrate, N-Cbz-Gly-R110-PFB. Samples incubated with N-Gly-R110-PFB together with cell lysate gave a strong fluorescent signal which was linear over the incubation times tested. The data for the 2 hour timepoint is shown in FIG. 3. Samples incubated with N-Gly-R110-PFB and buffer only (no lysate) gave a very weak fluorescent signal. N-Cbz-Gly-R110-PFB did not give a signal when incubated with cell lysate or buffer, indicating that this compound cannot be cleaved by aminopeptidases, as expected. These data show that N-Gly-R110-PFB is a suitable fluorogenic substrate for aminopeptidases. It has a low background in its uncleaved state and a strong fluorescent signal in its cleaved state.

EXAMPLE 57

Staining of Whole, Live HL-60 Cells with N-Gly-R110-PFB

Figure 4A:
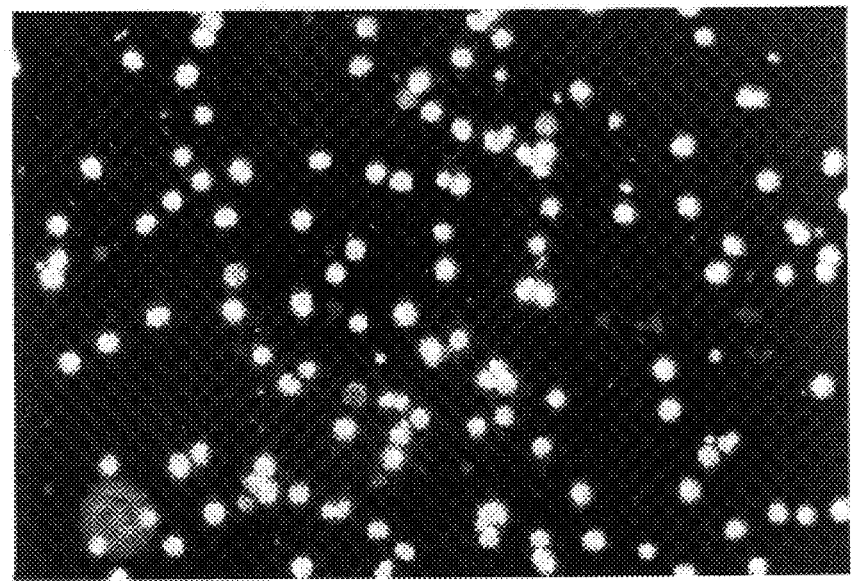
FIGS. 4A and 4B depict photographs showing the staining of HL-60 Cells with N-Gly-R110-PFB (4A) compared to N-Cbz-Gly-R110-PFB (4B).
Figure 4B:
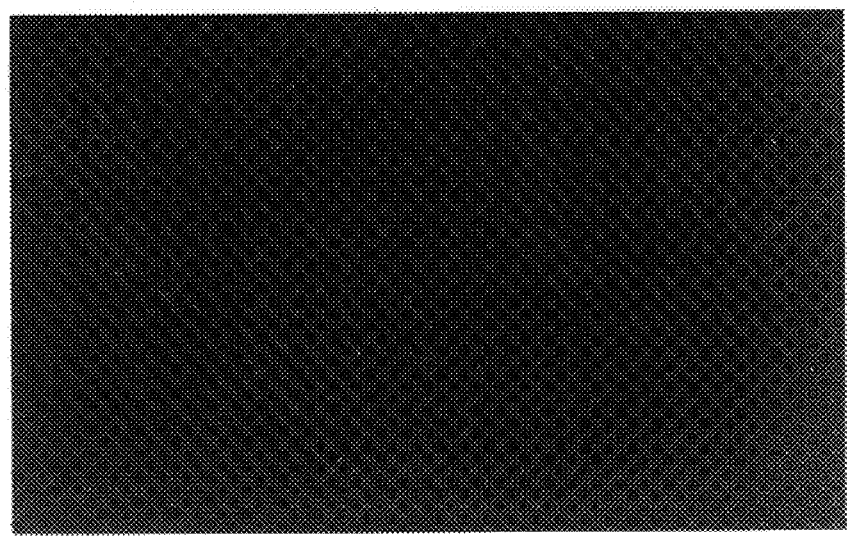

HL-60 cells (about 2×10$^6$) were incubated with 10 μM of N-Gly-R110-PFB for 2 hours at 37° C. in a CO$_2$ incubator. Parallel samples were similarly incubated with the amino terminal-blocked compound, N-Cbz-Gly-R110. At the end of the incubation, the cells were harvested by centrifugation and resuspended in 50 μL of fresh medium without substrate. Aliquots of each cell suspension were placed in microslides and viewed on a Nikon inverted microscope with epifluorescent illumination. Cells incubated with N-Gly-R110-PFB exhibited a strong, homogeneously distributed, yellowish-green fluorescence. Cells incubated with N-Cbz-Gly-R110 did not fluoresce above background levels (FIGS. 4A and 4B). This experiment shows that N-Gly-R110-PFB can be used to detect aminopeptidase activity in whole cells and that it gives an intense signal which is well-retained and not subject to quick fading or leaching.

EXAMPLE 58

Figure 5:
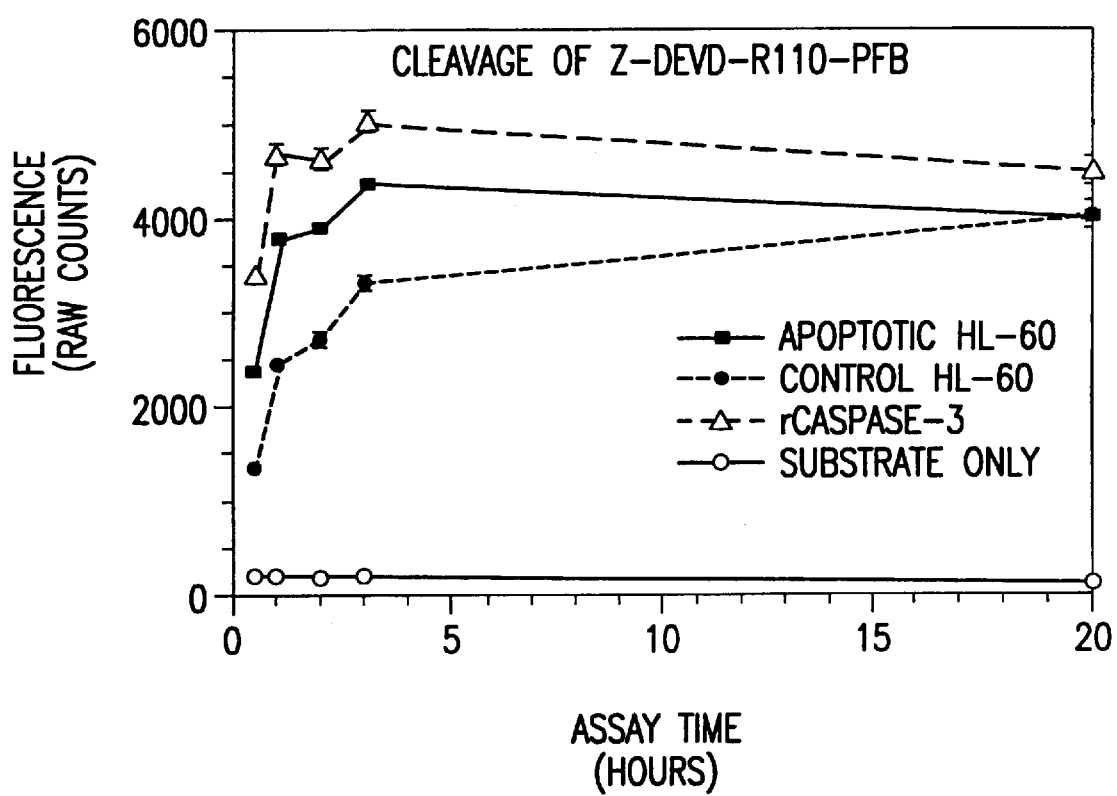
FIG. 5 depicts a graph showing the cleavage of N-Z-DEVD-R110-PFB (SEQ ID NO:5) by rCaspase-3 and HL-60 lysates.

Cleavage of Z-DEVD-R110-PFB (SEQ ID NO:5) by Recombinant Caspase-3 and by HL-60 Lysates Z-DEVD-R110-PFB (SEQ ID NO:5) was readily cleaved by recombinant caspase-3, resulting in a greater than 10-fold increase in fluorescence over the uncleaved substrate. A lysate from apoptotic HL-60 cells also readily cleaved Z-DEVD-R110-PFB (SEQ ID NO:5), as did lysate from control cells, although to a lesser extent (FIG. 5). These experiments show that Z-DEVD-R110-PFB (SEQ ID NO:5) is a suitable fluorogenic substrate for caspase-3, with a low background fluorescence and a strong fluorescent signal in the cleaved state.

EXAMPLE 59

Cleavage of-(Ac-DEVD)-N'-(2,3,4,5-tetrafluorobenzoyl)-R$_{110}$ (SEQ ID NO:5) by Recombinant Caspase-3

Figure 6:
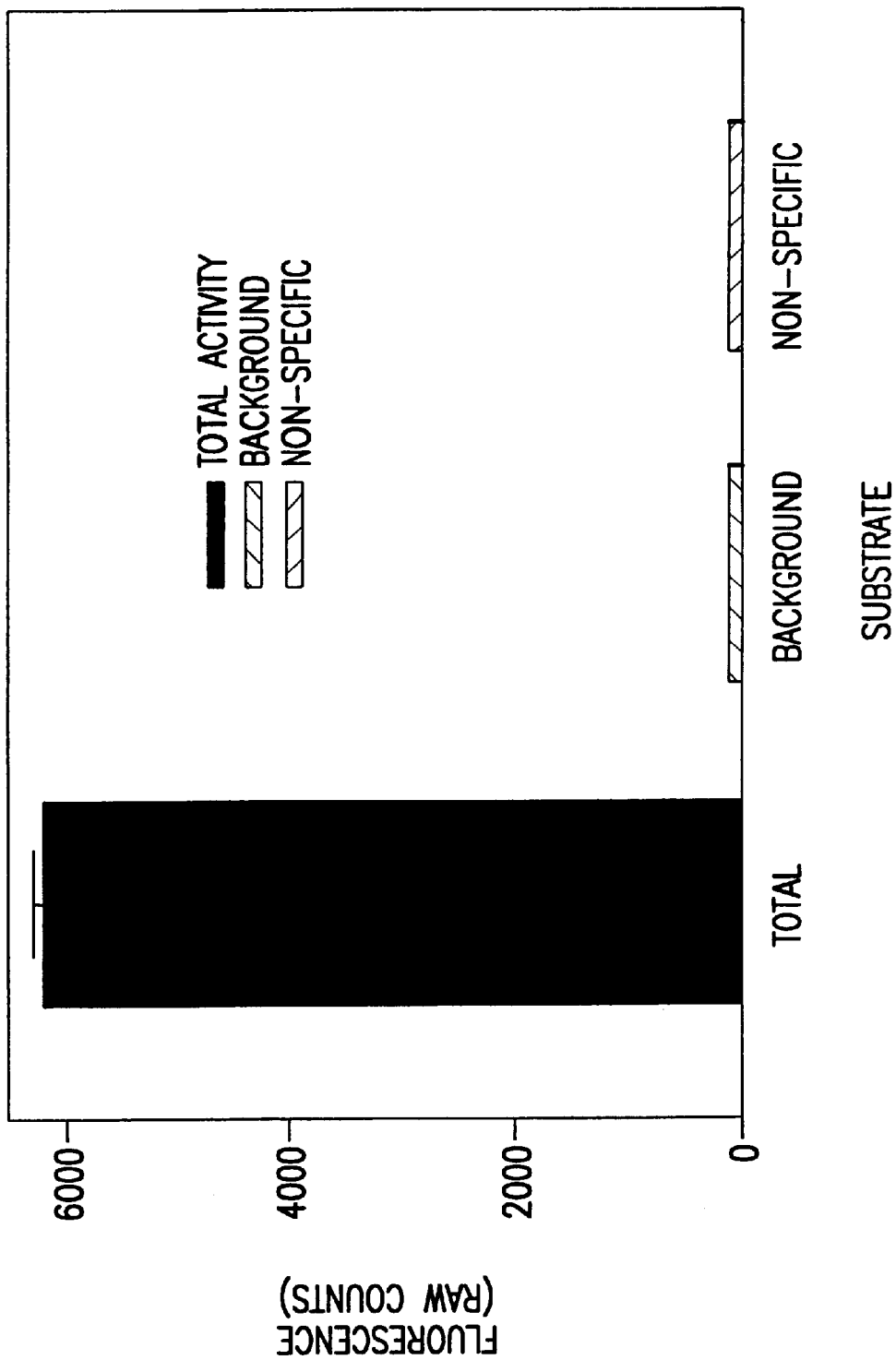
FIG. 6 depicts a bar graph with the results of a cleavage assay of Ac-DEVD-R110-TFB (SEQ ID NO:5) by recombinant caspase-3.

The cleavage of N-(Ac-DEVD)-N'-(2,3,4,5-tetrafluorobenzoyl)-R110 (SEQ ID NO:5) (Ac-DEVD-R110-TFB) (SEQ ID NO:5) by caspase-3 was tested in a cell-free assay using recombinant enzyme. 10 μM of substrate was incubated with recombinant caspase-3 for 3 hours at 37° C. Control reactions included one sample with no enzyme (Background value) and one sample incubated in the presence of the caspase inhibitor, Ac-DEVD-CHO (SEQ ID NO:5) (Non-specific value). As can be seen in FIG. 6, Ac-DEVD-R110-TFB (SEQ ID NO:5) was readily cleaved by recombinant caspase-3, resulting in a roughly 50-fold increase in fluorescence over background and non-specific values. These experiments show that Ac-DEVD-R110-TFB (SEQ ID NO:5) is a suitable fluorogenic substrate for caspase-3, with a low background fluorescence and a strong fluorescent signal in the cleaved state.

EXAMPLE 60

Figure 7:
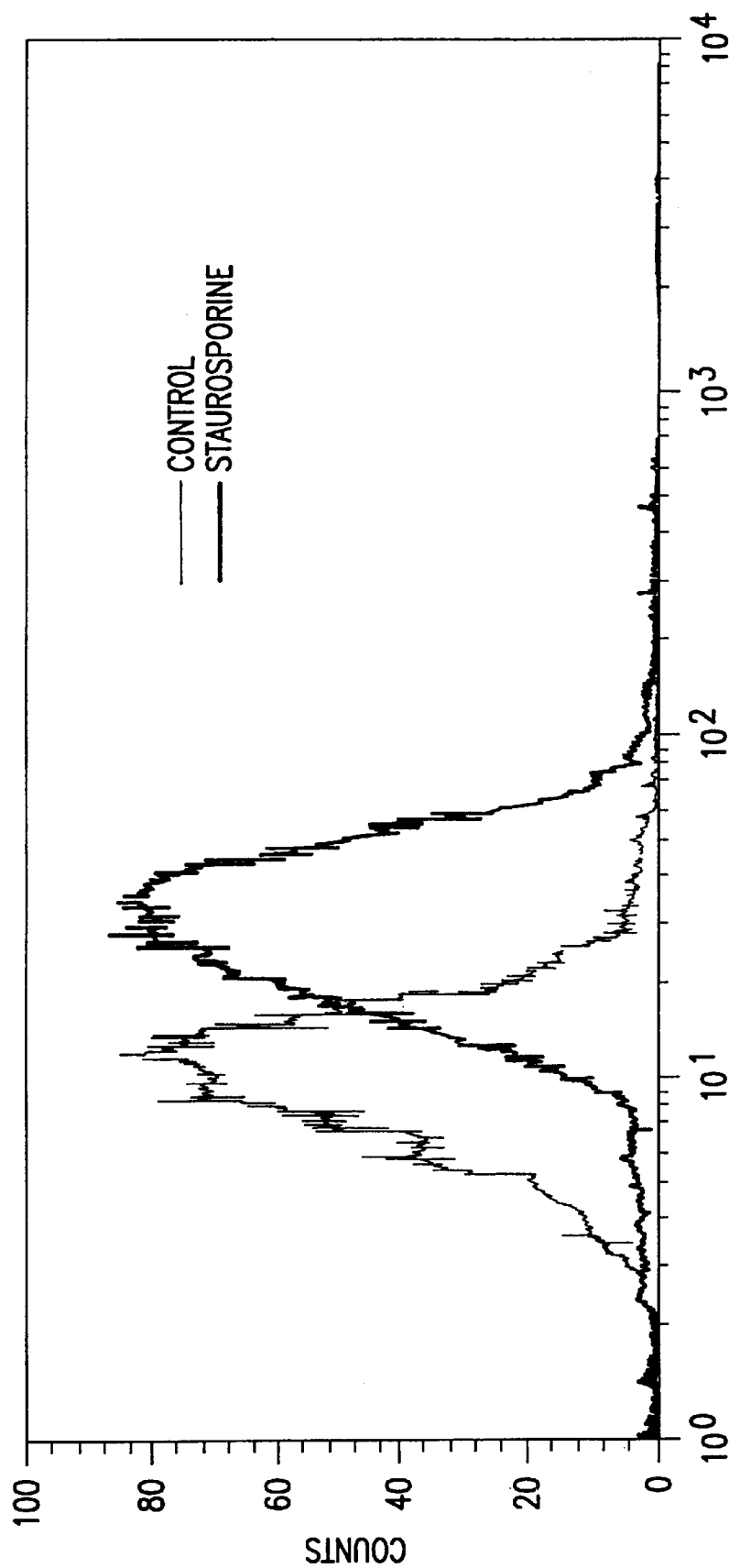
FIG. 7 depicts a graph showing the cleavage of Ac-DEVD-R110-TFB (SEQ ID NO:5) in staurosporine induced apoptotic cells.

Induction of Apoptosis with Staurosporine Leads to Cleavage of Z-DEVD-R110-TFB (SEQ ID NO:5) in a Whole Cell Assay Jurkat T leukemia cells were grown in RPMI 1640 media (Life Technologies, Inc.) +10% FCS (Sigma Chemical Company) in a 5% $CO_2$–95% humidity incubator at 37° C., and maintained at a cell density between 4 and $8 \times 10^5$ cells/ml. Cells were harvested at 200×g and resuspended at $1 \times 10^6$ cells/ml into RPMI 1640 media containing 10% FCS and 1 ml each were dispensed in 2-wells of a 6-well plate. The apoptosis inducer staurosporine was added at 0.5 µg/ml concentration and the plate was incubated for 2 hrs at 37° C. in a 5% $CO_2$–95% humidity incubator. Cells were pelleted and incubated with 50 µM of substrate Ac-DEVD-R110-TFB (SEQ ID NO:5) for 2 hrs at 37° C. in serum-free RPMI medium. 500 µl PBS was added and samples were analyzed by flow cytometry. All flow cytometry analyses were performed on a FACScalibur (Becton Dickinson) using CellQuest analysis software. FIG. 7 shows that induction of apoptosis in Jurkat cells by staurosporine leads to cleavage of the caspase-3 substrate Ac-DEVD-R110-TFB (SEQ ID NO:5) under whole cell assay conditions.

EXAMPLE 61

Figure 8:
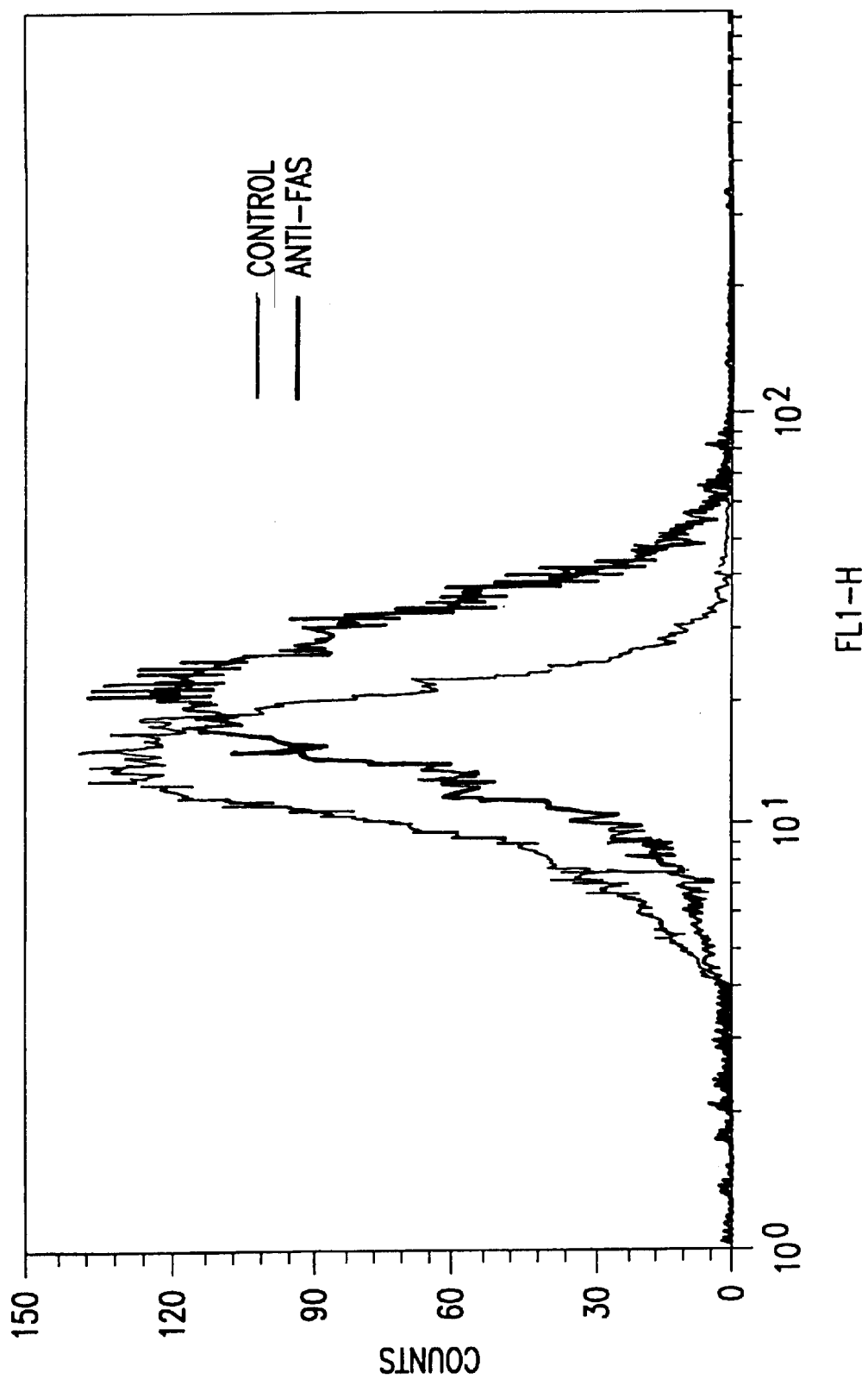
FIG. 8 depicts a graph showing the cleavage of Ac-DEVD-R110-TFB (SEQ ID NO:5) in Anti-Fas antibody induced apoptotic cells.

Induction of Apoptosis with Anti-Fas Antibody Leads to Cleavage of Ac-DEVD-R110-TFB in a Whole Cell Assay Jurkat T leukemia cells were grown and harvested in a way similar to Example 60. The apoptosis inducer anti-Fas antibody (CH-11; MBL) was added at 200 ng/ml concentration and the plate was incubated for 2 hrs at 37° C. in a 5% $CO_2$–95% humidity incubator. Cells were pelleted and incubated with 50 µM of substrate Ac-DEVD-R110-TFB (SEQ ID NO:5) for 2hrs at 37° C. in serum-free RPMI medium. 500 µl PBS was added and samples were analyzed by flow cytometry. FIG. 8 showed that induction of apoptosis in Jurkat cells by anti-Fas antibody leads to cleavage of the caspase-3 substrate Ac-DEVD-R110-TFB (SEQ ID NO:5) under a whole cell assay conditions.

EXAMPLE 62

Figure 9:
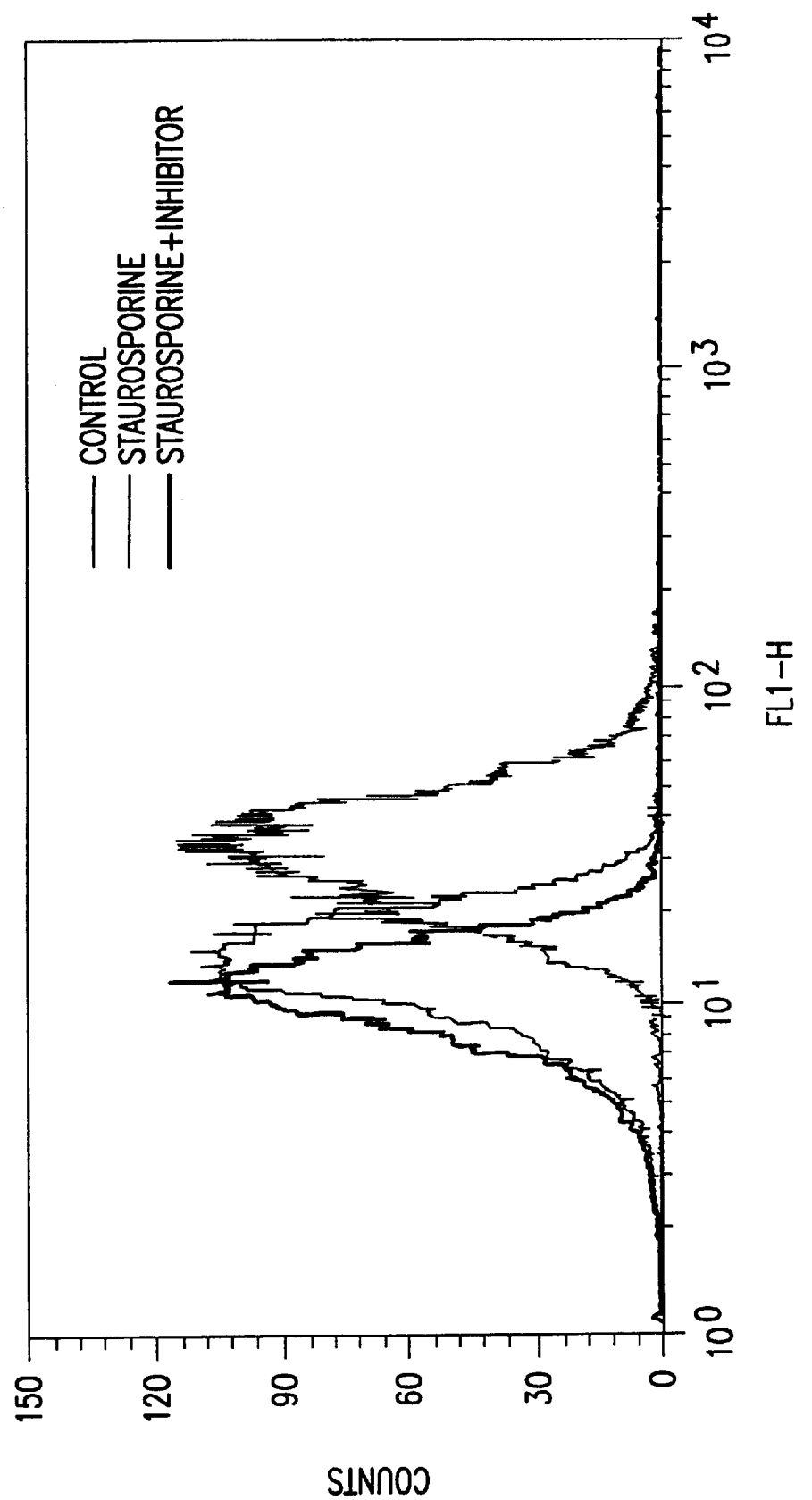
FIG. 9 depicts a graph showing the cleavage of Ac-DEVD-R110-TFB (SEQ ID NO:5) in staurosporine induced apoptotic cells and its inhibition by a pan-caspase inhibitor.

Cleavage of Z-DEVD-R110-TFB in Whole Cells Can be Inhibited by the Pan-caspase Inhibitor Jurkat T leukemia cells were grown and harvested in a way similar to Example 60. A pan-caspase inhibitor cbz-Val-Asp-fink(see WO99/18781) was added to one of the wells. The apoptosis inducer staurosporine was added with and without the caspase inhibitor at 0.5 µg/ml concentration and the plate was incubated for 2hrs at 37° C. in a 5% $CO_2$–95% humidity incubator. Cells were pelleted and incubated with 50 µM of substrate Ac-DEVD-R110-TFB (SEQ ID NO:5) for 2hr at 37° C. in serum-free RPMI medium. 500 µl PBS was added and samples were analyzed by flow cytometry. FIG. 9 showed that induction of apoptosis in Jurkat cells by staurosporine leads to cleavage of the caspase substrate Ac-DEVD-R110-TFB (SEQ ID NO:5) which can be inhibited by the pan-caspase inhibitor under a whole cell assay conditions.

EXAMPLE 63

Fluorescence Assay of CPP-32 in Jurkat Cells Stimulated by Fas Ligand

The cleavage of the enzyme poly(ADP)ribose polymerase (PARP) appears to occur in all cells in which the caspase proteolytic cascade is activated. For this reason, PARP cleavage is widely used as a biochemical marker for caspase-mediated apoptosis. The ability of a cytoprotective drug to block PARP cleavage is considered to be an indication of the drug's ability to inhibit the caspase proteolytic cascade and, in particular, CPP-32 (caspase-3), the main PARP protease. Measuring PARP cleavage is a slow and tedious process that is not suitable for HTCA assays and it is very inconvenient for drug screening and diagnostic procedures. The activity of CPP-32 inside cells may be assayed by the fluorescence assays described in herein by using, for example, the fluorogenic CPP-32 substrate Ac-DEVD-R110-TFB (SEQ ID NO:5), and incubating, for example, Jurkat cells, a human T-cell line, with substrate Ac-DEVD-R110-TFB (SEQ ID NO:5) during Fas-mediated apoptosis. This cell culture model of apoptosis is well-characterized and is known to involve activation of at least two caspases, caspase-3 (CPP32) and caspase-8 (FLICE/MACH).

For CPP-32 fluorescence assays, Jurkat cells may be seeded at a density of, for example, 10,000 cells per well in 96-well multidishes in RPMI 1640 medium containing 10% FBS, or another suitable medium. Dishes containing larger numbers of wells (e.g. 300–3,000 wells per ,ish) may also be used (with appropriately adjusted volume and number of cells). The cells may be pre-incubated with e.g. 0.01 nM–1M of Ac-DEVD-R110-TFB (SEQ ID NO:5) in the presence or absence of a test compound or compounds at a concentration of e.g. 0.01 nM–1M for 2 hours at 37° C. in a $CO_2$ incubator. Baseline fluorescence emission may be recorded with a suitable fluorescence recorder prior to, at the time of, or after adding Ac-DEVD-R110-TFB (SEQ ID NO:5) and test compound or compounds. A monoclonal antibody to Fas may then be added at a final concentration of 500 ng/ml. Incubation at 37° C. in a $CO_2$ incubator may be continued for an additional 4 hours. At the end of the incubation period, fluorescence may be recorded in the wells with a suitable plate reader or any other suitable instrument that can detect fluorescence. The increase in enzyme activity caused by stimulating the caspase cascade with Fas ligand may be calculated by subtracting the fluorescence measured at baseline from the fluorescence measured after stimulation of apoptosis enzyme with Fas ligand antibody. Specificity of the fluorescence emission as an indicator of caspase cascade activation may be determined by adding a known caspase inhibitor such as Z-DEVD-fmk (SEQ ID NO:5), Z-VAD-fmk (Hara et al., *Proc. Natl. Acad. Sci. USA* 94:2007–12 (1997)) or any other caspase cascade inhibitor to the incubation mixture. The preincubation time and the total incubation time may be varied as appropriate to be shorter or longer than is indicated in this example. The optimal incubation time may be determined experimentally in each cell, cell line line or tissue in which caspase activity is to be measured. Instead of Ac-DEVD-R110-TFB (SEQ ID NO:5) as fluorogenic substrate, any other fluorogenic or fluorescent substrate of this invention may used. Instead of Jurkat cells, any other cells or cell lines be they normal, diseased, infected or cancerous may be used. These cells or cell lines

EXAMPLE 64

Use of Fluorescence Assay in Screening for Drugs that Stimulate the Caspase Cascade Drugs that stimulate the caspase cascade in the absence of Fas ligand may be useful, for example, as anti-cancer chemotherapeutic agents. The assay described in Example 63 may be used to screen for drugs that stimulate the caspase cascade by carrying out the assay under similar conditions as in Example 63, except that a known or unknown compound with known or unknown anti-cancer or anti-tumor activity replaces the Fas ligand reagent.

EXAMPLE 65

Use of Fluorescence Assay in Screening for Drugs that Inhibit or Potentiate the Caspase Cascade Stimulated with Fas Ligand or Another Apoptosis Inducer Drugs that inhibit the caspase cascade may be useful in treating degenerative and other diseases caused by or associated with an inadequate activation of the caspase cascade. Drugs that potentiate the action of another caspase stimulator, such as e.g. Fas ligand or an anti-cancer drug or agent, may be suitable to treat cancers or tumors caused by or associated with an inappropriate function of the caspase cascade. The assays and reagents described in this invention may be used to screen for drugs that either inhibit or potentiate the caspase cascade in cells by performing the assay as described in Example 63, using Fas ligand or any other agent that stimulates the caspase cascade or other apoptosis pathway in the presence of a test substance that inhibits or potentiates or acts synergistically with the action of the first apoptosis or caspase cascade inducer.

EXAMPLE 66

Use of Fluorescence Assay in Testing Samples Cancer Cells from Patients for Chemosensitivity to Anti-cancer Drugs It is well known that the same cancer in different patients shows a great variability to treatment with anti-cancer drugs. Therefore it is very difficult to predict whether a cancer in a patient is treatable with a particular anti-cancer drug before treatment is begun. The fluorescence assays described in this invention permit chemosensitivity or drug resistance testing of cancer or tumor cells or tissue samples taken from individual cancer or tumor patients. To perform the chemosensitivity test, a fluorescence assay using a cancer cell or tissue sample taken from a patient may be conducted as described Example 65. Using this approach, different drugs with known or unknown chemotherapeutic activity can be tested for their capacity to stimulate the caspase cascade. The results from this assay provide information that can be used to design an optimal chemotherapeutic drug treatment regimen for the patient.

Having now fully described this invention, it will be understood by those of ordinary skill in the art that the same can be performed within a wide and equivalent range of conditions, formulations and other parameters without affecting the scope of the invention or any embodiment thereof. All patents, patent applications and publications cited herein are fully incorporated by reference herein in their entirety.

What is claimed is:

1. A compound having the following structural formula:

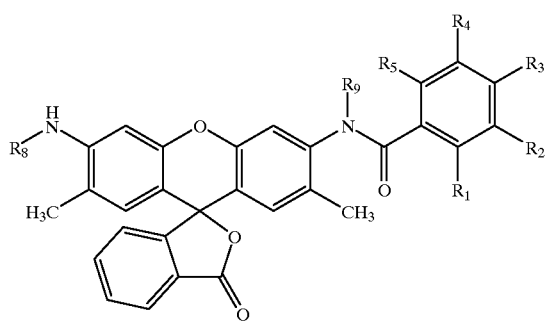

or a biologically acceptable salt thereof, wherein $R_8$ and $R_9$ are each independently selected from the group consisting of hydrogen, alkyl and aryl;

$R_1$–$R_5$ are each independently selected from the group consisting of fluoro, chloro, bromo, iodo, nitro and haloalkyl.

2. The compound of claim 1, wherein the haloalkyl group is selected from the group consisting of fluoromethyl, difluoromethyl, trifluoromethyl, pentafluoroethyl, 1,1-difluoroethyl, chloromethyl, chlorofluoromethyl and trichloromethyl.

3. The compound of claim 1, wherein $R_8$ and $R_9$ are hydrogen.

4. The compound of claim 1 which is N-pentafluorobenzoyl-Rhodamine 19.

5. The compound of claim 1 which is N-(2,3,4,5-tetrafluorobenzoyl)-Rhodamine 19.

6. The compound of claim 1 which is N-(2,4,6-trifluorobenzoyl)-Rhodamine 19.

7. A compound having the following structural formula:

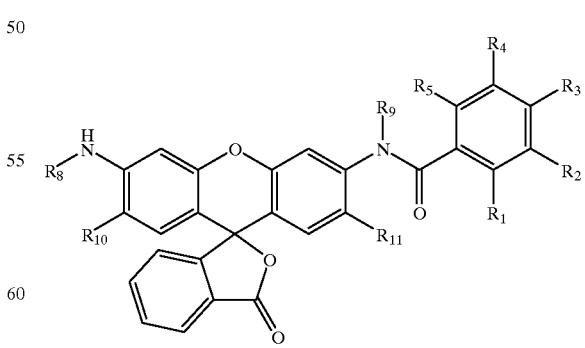

or a biologically acceptable salt thereof, wherein $R_8$ and $R_9$ are each independently selected from the group consisting of hydrogen, alkyl and aryl;

$R_{10}$ and $R_{11}$ are each independently selected from the group consisting of hydrogen and alkyl;

$R_1$–$R_5$ are each independently selected from the group consisting of fluoro, chloro, bromo, iodo, nitro and haloalkyl;

provided that at least one of $R_1$–$R_5$ is a haloalkyl group.

8. The compound of claim 7, wherein the haloalkyl group is selected from the group consisting of fluoromethyl, difluoromethyl, trifluoromethyl, pentafluoroethyl, 1,1-difluoroethyl, chloromethyl, chlorofluoromethyl and trichloromethyl.

9. The compound of claim 7, wherein the haloalkyl group is trifluoromethyl.

10. The compound of claim 9, which is N-(4-fluoro-3-trifluoromethyl-benzoyl)-Rhodamine 110.

* * * * *